US012746259B2

(12) United States Patent
Cheng et al.

(10) Patent No.: US 12,746,259 B2
(45) **Date of Patent: *Sep. 29, 2026**

(54) MAMMALIAN LUNG SPHEROIDS AND LUNG SPHEROID CELLS AND USES THEREOF

(71) Applicant: North Carolina State University, Raleigh, NC (US)

(72) Inventors: Ke Cheng, Raleigh, NC (US); Eric T. Henry, Raleigh, NC (US); Jhon Cores, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 60 days.

This patent is subject to a terminal disclaimer.

(21) Appl. No.: 18/647,995

(22) Filed: Apr. 26, 2024

(65) Prior Publication Data

US 2024/0350554 A1 Oct. 24, 2024

Related U.S. Application Data

(63) Continuation of application No. 17/071,303, filed on Oct. 15, 2020, now Pat. No. 11,998,570, which is a continuation of application No. 15/512,463, filed as application No. PCT/US2015/050835 on Sep. 18, 2015, now abandoned.

(60) Provisional application No. 62/052,220, filed on Sep. 18, 2014.

(51) Int. Cl.
*A61K 35/42* (2015.01)
*C12N 5/071* (2010.01)

(52) U.S. Cl.
CPC ............ *A61K 35/42* (2013.01); *C12N 5/0688* (2013.01); *C12N 2513/00* (2013.01); *C12N 2533/50* (2013.01); *C12N 2533/52* (2013.01)

(58) Field of Classification Search
CPC .............................. A61K 35/42; C12N 5/0688
See application file for complete search history.

(56) References Cited

U.S. PATENT DOCUMENTS

| | | | |
|---|---|---|---|
| 5,437,994 A | 8/1995 | Emerson et al. | |
| 5,665,350 A | 9/1997 | Quesenberry | |
| 5,674,722 A | 10/1997 | Mulligan et al. | |
| 6,020,380 A * | 2/2000 | Killian | A61K 31/192 514/570 |
| 6,251,383 B1 | 6/2001 | Upadhyay et al. | |
| 6,575,898 B2 | 6/2003 | Smith | |
| 7,682,828 B2 | 3/2010 | Jaenisch et al. | |
| 8,080,417 B2 | 12/2011 | Peled et al. | |
| 8,420,380 B2 | 4/2013 | Fishman et al. | |
| 8,703,121 B2 | 4/2014 | Harris et al. | |
| 8,741,642 B2 | 6/2014 | Manjili et al. | |
| 8,790,638 B2 | 7/2014 | Tankovich et al. | |
| 8,815,585 B2 | 8/2014 | Beardsley et al. | |
| 2008/0233610 A1 | 9/2008 | Thomson et al. | |
| 2009/0246875 A1 | 10/2009 | Yamanaka et al. | |
| 2009/0280469 A1 | 11/2009 | Jujiwara et al. | |
| 2010/0061966 A1 | 3/2010 | Marban et al. | |
| 2013/0058905 A1 | 3/2013 | Slukvin et al. | |
| 2014/0106432 A1 | 4/2014 | Fujiwara et al. | |
| 2014/0120573 A1 | 5/2014 | Tavana et al. | |
| 2015/0267174 A1 | 9/2015 | Hayashi et al. | |

FOREIGN PATENT DOCUMENTS

| | | |
|---|---|---|
| EP | 2907870 A1 | 8/2015 |
| EP | 1040185 B2 | 2/2018 |
| WO | WO 2009/006930 A1 | 1/2009 |
| WO | WO 2009/006997 A1 | 1/2009 |
| WO | WO 2009/007852 A2 | 1/2009 |
| WO | WO 2011/048350 A1 | 4/2011 |
| WO | WO 2012/047951 A2 | 4/2012 |
| WO | WO 2012/047951 A3 | 6/2012 |
| WO | WO 2012/131000 A1 | 10/2012 |

OTHER PUBLICATIONS

Amann et al. "Development of an Innovative 3D Cell Culture System to Study Tumour-Stroma Interactions in Non-Small Cell Lung Cancer Cells." PLoS One. 2014: e92511.
Anonymous. "Corning Ultra-Low Attachment Surface"; downloaded from: https://www.corning.com/worldwide/en/products/life-sciences/products/surfaces/ultra-low-attachment-surface.html on Nov. 5, 2019. (Year: 2019).
Barkauskas et al. "Type 2 alveolar cells are stem cells in adult lung." The Journal of Clinical Investigation 2013, 123:3025-36.
Celiz et al. "Materials for stem cell factories of the future." Nat Mater, 2014, 13 570-579.
Chapman et al."Integrin alpha6beta4 identifies an adult distal lung epithelial population with regenerative potential in mice." J Clin Investig. 2011, 121:2855-62.
Chimenti et al. "Relative Roles of Direct Regeneration Versus Paracrine Effects of Human Cardiosphere-Derived Cells Transplanted Into Infarcted Mice." Circulation Research, 2010, 106:971-80.
Chugh et al. "Administration of Cardiac Stem Cells in Patients with Ischemic Cardiomyopathy (the SCIPIO Trial): Surgical Aspects and Interim Analysis of Myocardial Function and Viability by Magnetic Resonance." Circulation 2012, 126 S54-S64.

(Continued)

*Primary Examiner* — Sharmila G Landau
*Assistant Examiner* — Paul C Martin
(74) *Attorney, Agent, or Firm* — Casimir Jones, S.C.; Peter J. Schlueter

(57) ABSTRACT

Using lung tissues as a source, mammalian lung progenitor cells lung spheroids and lung spheroid cells (LSCs) were prepared. In one embodiment mammalian LSCs were prepared by (i) culturing mammalian lung tissue explant cells under adherent culture conditions to form a first lung cell outgrowth culture; (ii) culturing the first lung cell outgrowth culture under low-adherence conditions to form lung spheroids; and (iii) culturing the lung spheroids under adherent culture conditions so as to form LSCs. The low-adherence conditions may be a cell culture or suspension. The lung spheroids or LSCs may be formulated into pharmaceutical compositions. Uses such as treatment of lung diseases or diagnostics are also provided. Lung spheroids and LSCs represent a simple and highly reproducible method to generate therapeutic lung cells.

21 Claims, 38 Drawing Sheets

(56) References Cited

OTHER PUBLICATIONS

Figure 1A:
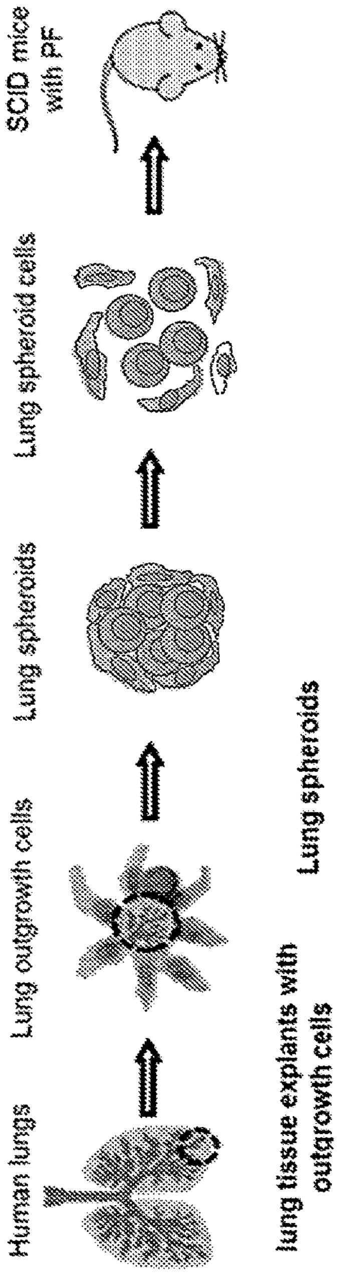

Cottin, "Interstitial lung disease." European Respiratory Review. 2013, 22:26-32.
Deleyrolle et al. "Isolation, Expansion, and Differentiation of Adult Mammalian Neural Stem and Progenitor Cells Using the Neurosphere Assay." In: Gordon D, Scolding NJ, editors. Neural Cell Transplantation: Humana Press. 2009, p. 91-101.
Desai et al. "Alveolar progenitor and stem cells in lung development, renewal and cancer." Nature. 2014, 507:190-4.
Dihn et al. "Derivation of therapeutic lung spheroid cells from minimally invasive transbronchial pulmonary biopsies" Respiratory Research, 2017, 18:132, 11 pages.
Ekert et al. "Three-Dimensional Lung Tumor Microenvironment Modulates Therapeutic Compound Responsiveness In Vitro-Implication for Drug Development"; PLOS One, 2014, vol. 9, No. 3, pp. 1-14.
Endo et al. "Spheroid Culture of Primary Lung Cancer Cells With Neuregulin 1/HER3 Pathway Activation" J Thorac Oncol. Feb. 2013; 8(2):131-9.
EP Communication pursuant to Article 94(3) issued in counterpart EP Application No. 15842095.0 dated Mar. 28, 2019.
EP Communication pursuant to Rules 70(2) and 70a(2) EPC issued in counterpart EP Application No. 15842095.0 dated Apr. 9, 2018 (one (1) page).
Extended European Search Report issued in counterpart EP Application No. 15842095.0 dated Mar. 20, 2018 (nine (9) pages).
Farini et al. "Clinical Application of Mesenchymal Stem Cells in Chronic Diseases." Stem Cells Int. 2014: 2014:306573.
Fennema et al. "Spheroid culture as a tool for creating 3D complex tissues." Trends in Biotechnology, 2013, 31:108-15.
Ferrini et al. "Persistency of Mesenchymal Stromal/Stem Cells in Lungs" Front Cell Dev Biol. Jul. 16, 2021:9:709225.
Fujino et al. "Isolation of alveolar epithelial type II progenitor cells from adult human lungs" Lab Invest. Mar. 2011; 91(3):363-78.
Goumans et al."A Straightforward guide to the basic science behind cardiovascular cell-based therapies." Heart, 2014, 100: 1153-1157.
Guannan et al. "Direct Conversion of Fibroblasts into Neutral Progenitor-Like Cells by Foreced Growth into 3D Spheres on Low Attachment Surfaces" Biomaterials. Aug. 2013; 34(24):5897-906.
Guannan Su et al. "The Effect of Forced Cells into 3D Spheres Using Low Attachment Surfaces on the Acquisition of Sternness Properties" Biomaterials. Apr. 2013;34(13):3215-22.
Henry et al. "Adult Lung Spheroid Cells Contain Progenitor Cells and Mediate Regeneration in Rodents With Bleomycin-Induced Pulmonary Fibrosis" Stem Cells Transl Med. Nov. 2015; 4(11):1265-74.
Hogan et al. 2014. "Repair and Regeneration of the Respiratory System: Complexity, Plasticity, and Mechanisms of Lung Stem Cell Function." Cell Stem Cell. 2014, 15:123-38.
International Search Report and Written Opinion dated Jan. 14, 2016 from related International Application No. PCT/US2015/050835.
Isobe et al. "iPSCs, aging and age-related diseases." New Biotechnology, 2014, 31(5) 411-421.
Kajstura et al. "Evidence for Human Lung Stem Cells." New England Journal of Medicine, 2011, 364:1795-806.
Kanate et al. "Allogeneic hematopoietic cell transplant for acute myeloid leukemia: Current state in 2013 and future directions." World J Stem Cell, 2014, 6(2) 69¬81.
Kim et al. "Identification of bronchioalveolar stem cells in normal lung and lung cancer." Cell 2005, 121:823-35.
Kotton et al. "Lung regeneration: mechanisms, applications and emerging stem cell populations" Nat Med. 2014, 20:822-32.
Kumar et al. "Distal Airway Stem Cells Yield Alveoli In Vitro and during Lung Regeneration following H1N1 Influenza Infection." Cell. 2011, 147:525-38.
Labarbera et al. "The multicellular tumor spheroid model for high-throughput cancer drug discovery." Expert Opinion on Drug Discovery, 2012, 7:819¬30.
Lau et al. "Stem cells and regenerative medicine in lung biology and diseases" Molecular Therapy, 2012, vol. 20, No. 6, pp. 1116-1130.
Li et al. "Cardiospheres Recapitulate a Niche-Like Microenvironment Rich in Sternness and Cell-Matrix Interactions, Rationalizing Their Enhanced Functional Potency for Myocardial Repair." Stem Cells. 2010, 28:2088-98.
Makkar et al. "Intracoronary cardiosphere-derived cells for heart regeneration after myocardial infarction (CADUCEUS): a prospective, randomised phase 1 trial." The Lancet, 2012, 379:895-904.
Malliaras et al. "Intracoronary Cardiosphere-Derived Clls Aller Myocardial Infarction: Evidence of Therapeutic Regeneration in the Final 1-Year Results of the CADUCEUS Trial." J Am Coll Card, 2014, 63 110-122.
Mancini et al. "Spheres derived from lung adenocarcinoma pleural effusions: molecular characterization and tumor engraftment" PLOS One, 2011, vol. 6, No. 7, pp. 1-12.
Marban E. "Breakthroughs in Cell Therapy for Heart Disease: Focus on Cardiosphere-Derived Cells." Mayo Clinic Proceedings. 2014, 89:850-8.
Mcqualter et al. "Evidence of an epithelial stem/progenitor cell hierarchy in the adult mouse lung" Proc Natl Acad Sci U S A. Jan. 26, 2010;107(4):1414-9.
Messina et al. "Isolation and Expansion of Adult Cardiac Stem Cells From Human and Murine Heart." Circ. Res. 95 911-921.
Moodley et al. "Human umbilical cord mesenchymal stem cells reduce fibrosis of bleomycin-induced lung injury." Am J Pathol. 2009, 175:303-13.
Ortiz et al. "Mesenchymal stem cell engraftment in lung is enhanced in response to bleomycin exposure and ameliorates its fibrotic effects." Proc Natl Acad Sci U SA. 2003, 100:8407-11.
Ortiz et al. "Interleukin 1 receptor antagonist ediates the antiinflammatory and antifibrotic effect of mesenchymal stem cells during lung injury." Proc Natl Acad Sci U S A. 2007, 104: 11002-7.
Rojas et al. "Bone marrow-derived mesenchymal stem cells in repair of the injured lung." Am J Respir Cell Mol Bioi. 2005, 33:145-52.
Smith et al. "Regenerative Potential of Cardiosphere-Derived Cells Expanded From Percutaneous Endomyocardial Biopsy Specimens." Circulation, 2007, 115: 896-908.
Su et al. "Direct conversion of fibroblasts into neural progenitor-like cells by forced growth into 3D spheres on low attachment surfaces." Biomaterials. 2013, 34:5897-906.
Su et al. "The effect of forced growth of cells into 3D spheres using ow attachment surfaces on the acquisition of sternness properties." Biomaterials, 2013, 34:3215-22.
Sveiven et al. "Lung-resident mesenchymal stromal cells are tissue-specific regulators of lung homeostasis" Am J Physiol Lung Cell Mol Physiol. May 13, 2020; 319(2):L197-L210.
Takahashi et al. "Induction of Pluripotent Stem Cells from Adult Human Fibroblasts by Defined Factors." Cell. 2007, 131:861-72.
Takahashi et al. "Induction of pluripotent stem cells from mouse embryonic and adult fibroblast cultures by defined factors." Cell. 2006, 126:663-76.
Tala et al. "Dedifferentiation of committed epithelial cells into stem cells in vivo." Nature. 2013, 503:218-23.
Tesei et al. "Isolation of stem/progenitor cells from normal lung tissue of adult humans" Cell Prolif. Jun. 2009;42(3):298-308.
Thomson et al. "Embryonic Stem Cell Lines Derived from Human Blastocysts." Science, 1998, 282:1145-7.
Tzouvelekis et al. "A prospective, non-randomized, no placebo-controlled, phase Ib clinical trial to study the safety of the adipose derived stromal cells-stromal vascular fraction in idiopathic pulmonary fibrosis." J Transl Med. 2013, 11:171.
Vinci et al., "Advances in establishment and analysis of three-dimensional tumor spheroid-based functional assays for target validation"; BMC Biology, 2012, vol. 10, No. 29, pp. 1-20.
Viswanathan et al. "Human pluripotent stem cells on artificial microenvironments: a high content perspective." Frontiers in Pharmacology, 2014, 5: 150.
Wansleeben et al. "Stem cells of the adult lung: their development and role in homeostasis, regeneration, and disease." Wiley Interdiscip Rev Dev Biol. Jan.-Feb. 2013;2(1):131-48.

(56) References Cited

OTHER PUBLICATIONS

Yaghi et al. "Primary human bronchial epithelial cells grown from explants" J Vis Exp. Mar. 26, 2010:(37):1789.
Yang et al. "Cell-based therapy in lung regenerative medicine." Regenerative Medicine Research. 2:7. Available online Apr. 11, 2014.
Bahmad H.F., et al., "Sphere-Formation Assay: Three-Dimensional In Vitro Culturing of Prostate Cancer Stem/Progenitor Sphere-Forming Cells," Frontiers in Oncology, Aug. 28, 2018, vol. 8, Article. 347, pp. 1-14.

* cited by examiner

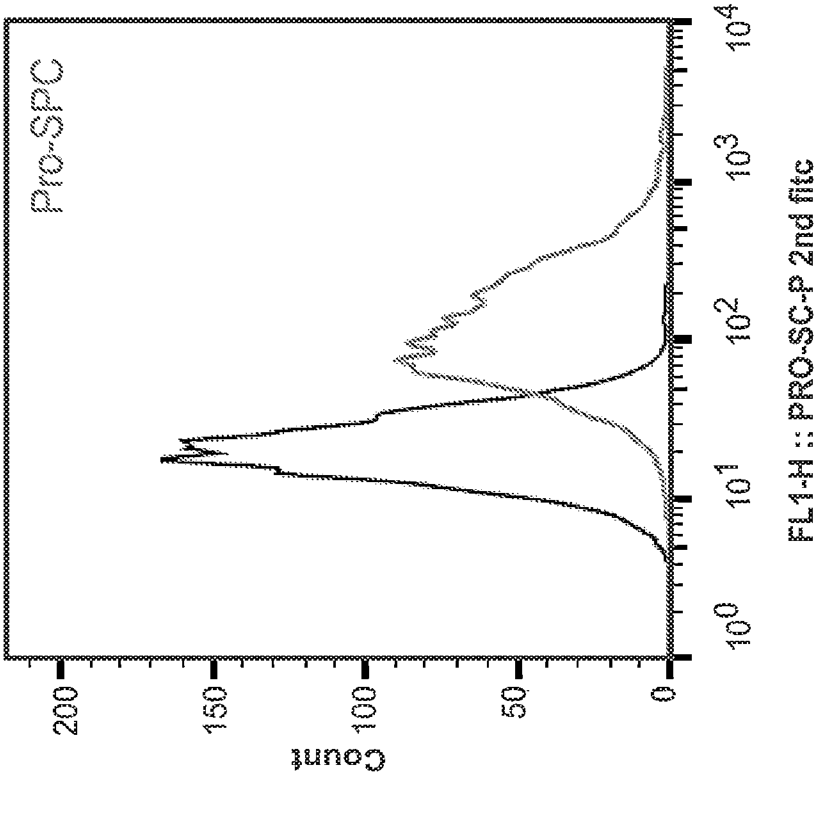
FIG. 2A(1)
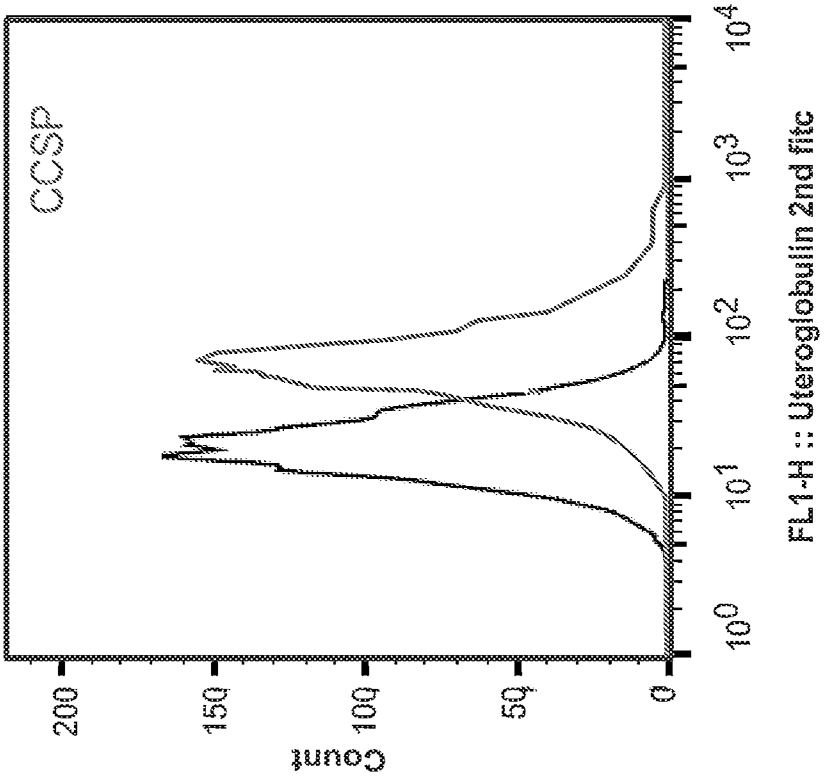
FIG. 2A(2)

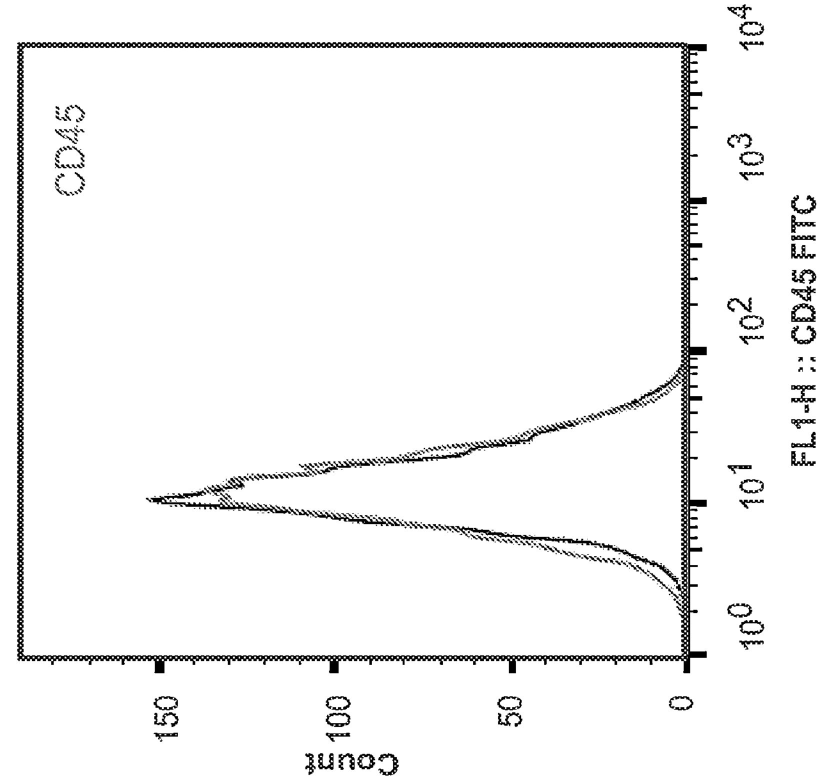
FIG. 2A(3)
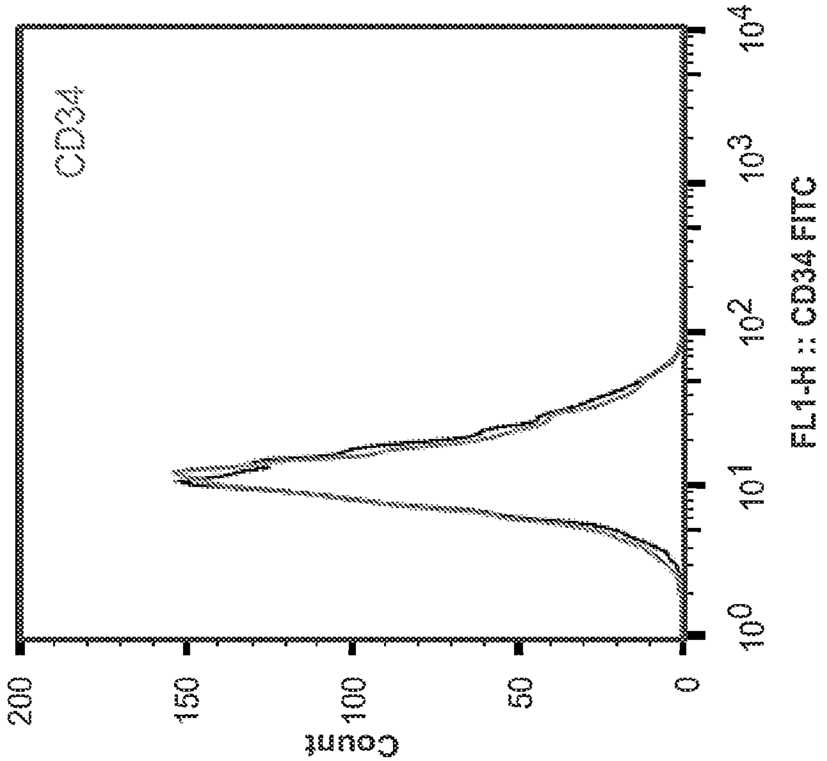
FIG. 2A(4)

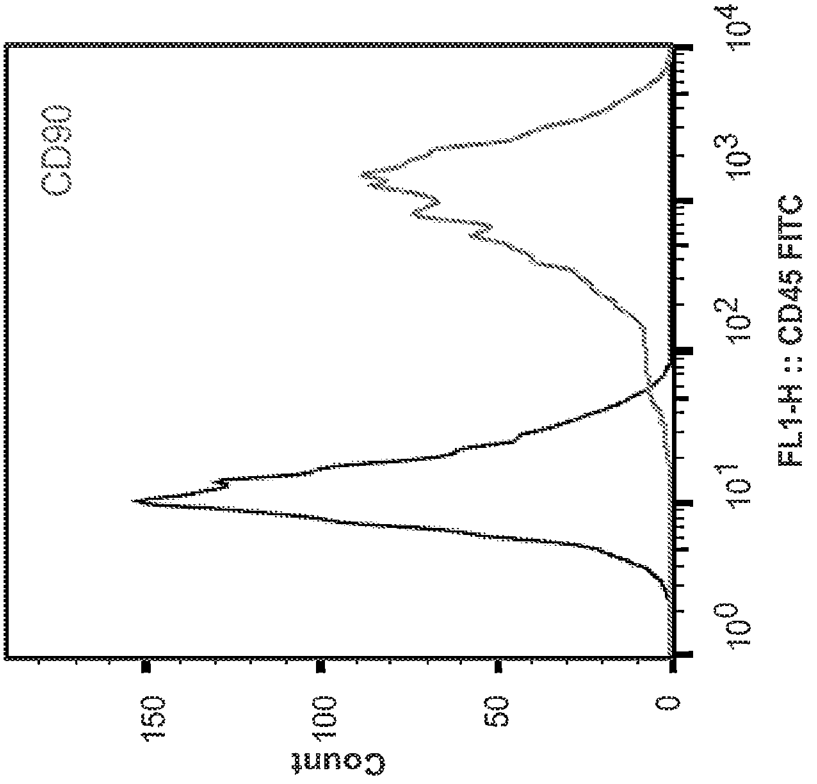
FIG. 2A(5)
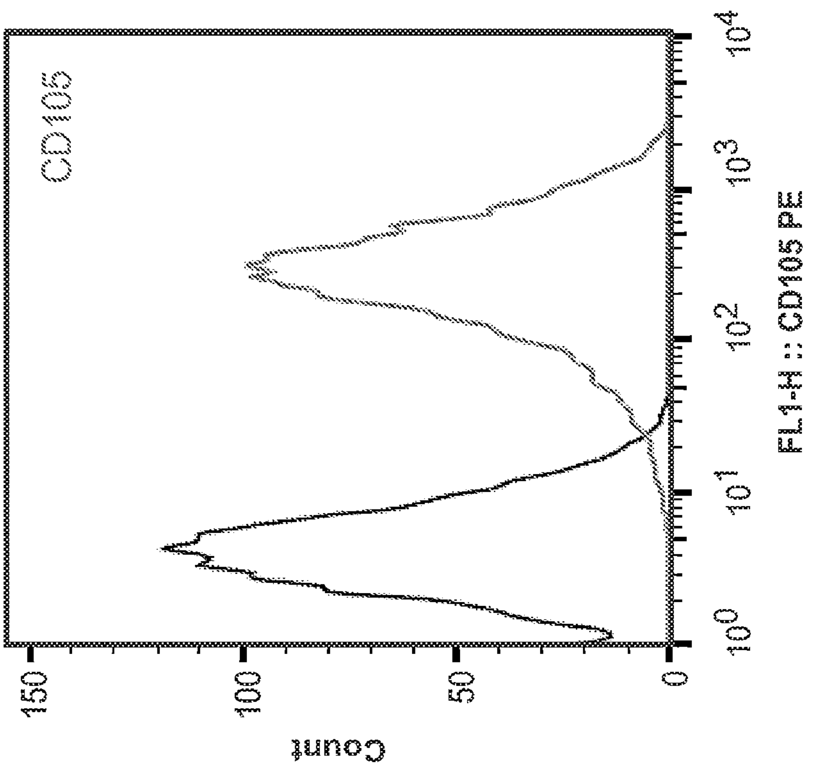
FIG. 2A(6)

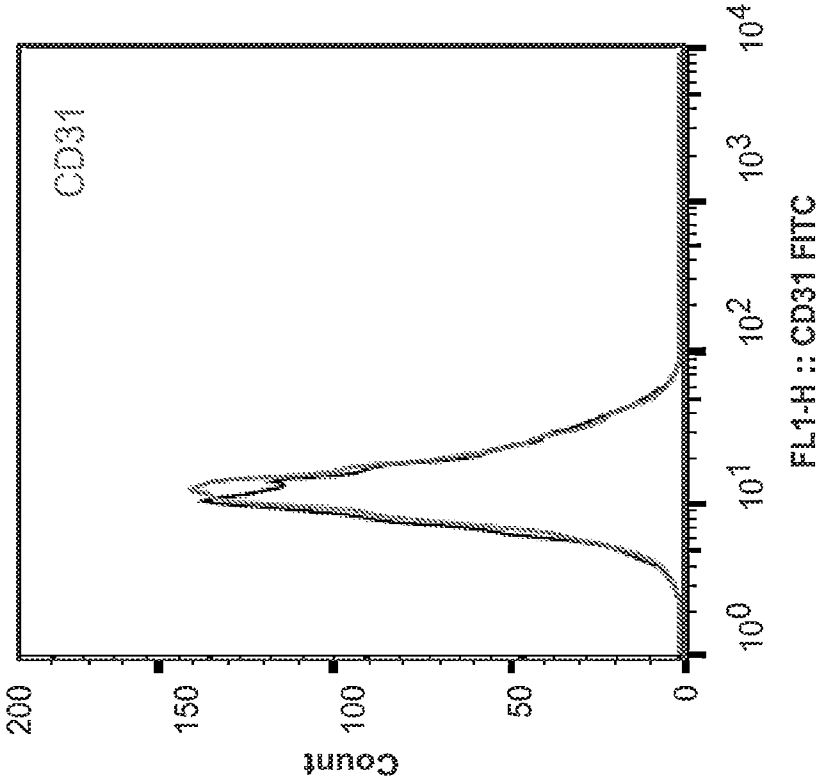
FIG. 2A(7)
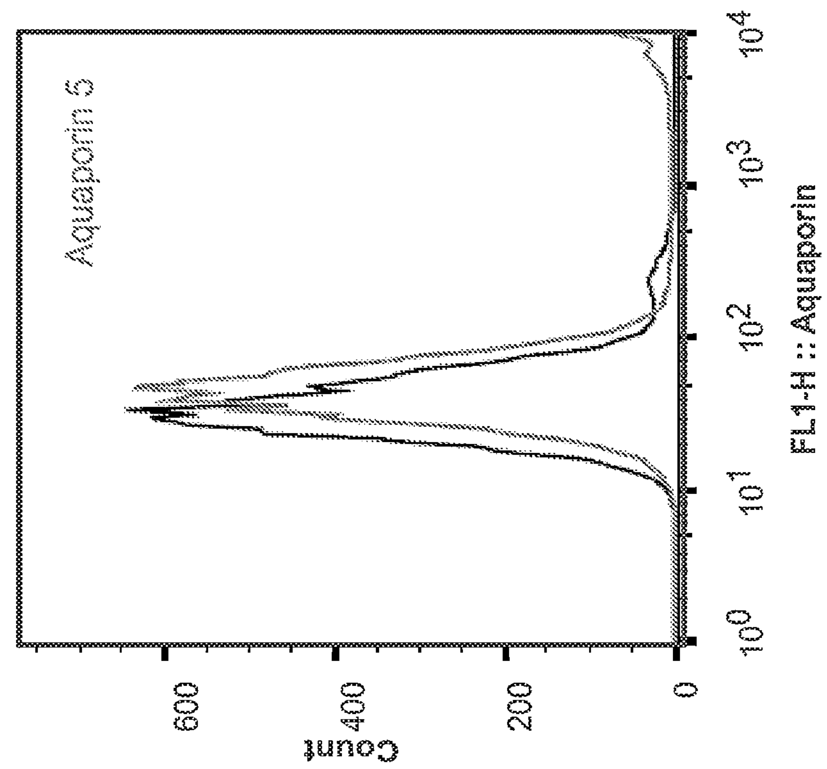
FIG. 2A(8)

FIG. 3C(1)

FIG. 3D(1)

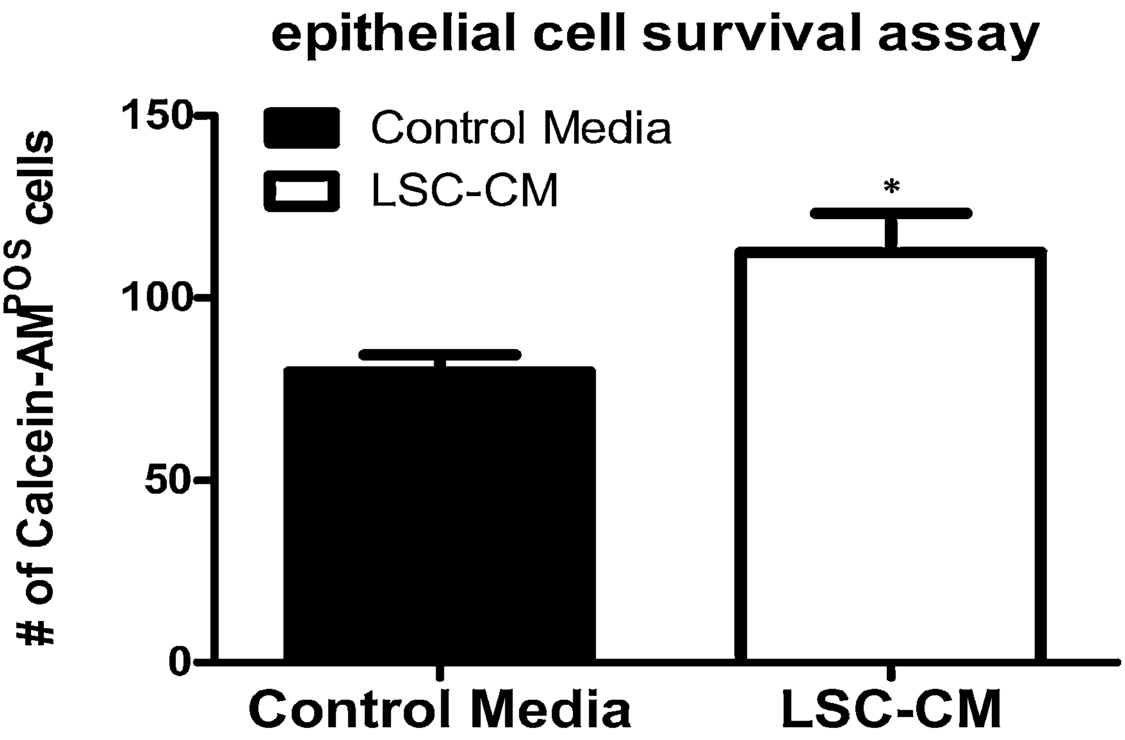
FIG. 3C(2)
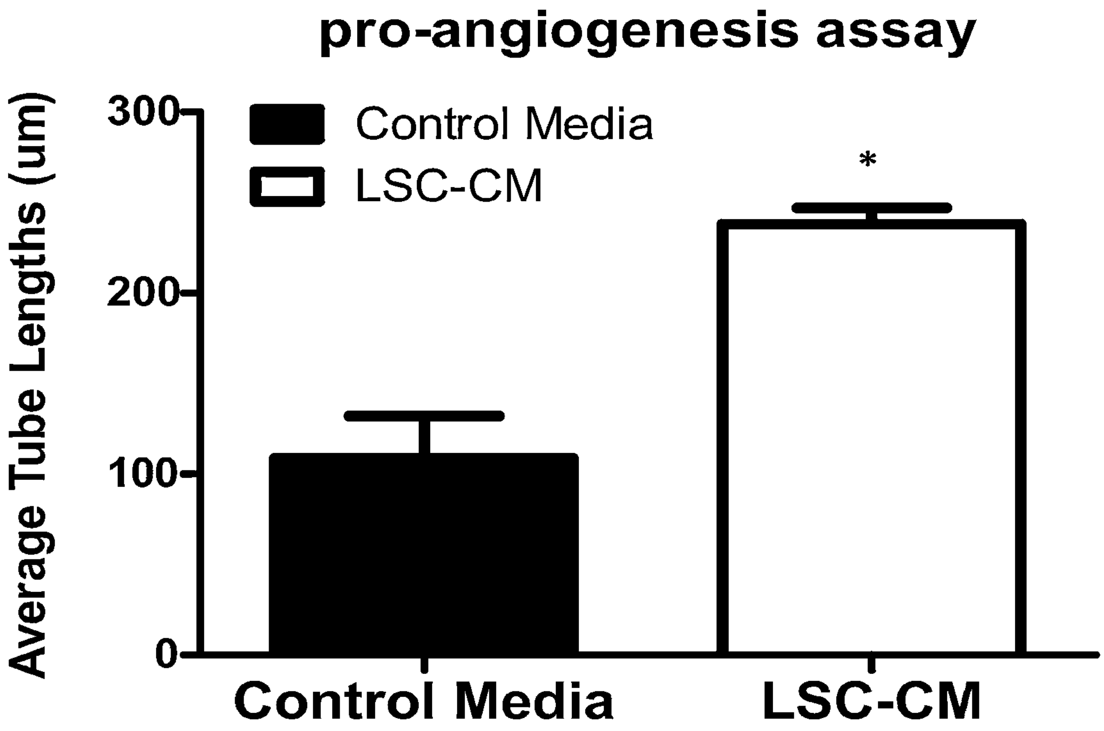
FIG. 3D(2)

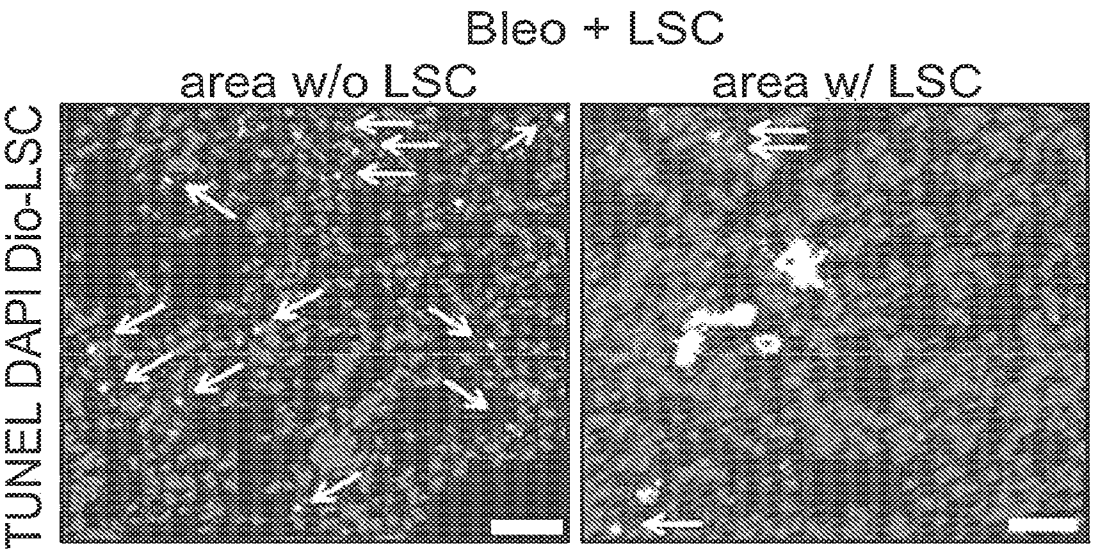
FIG. 5A(1)
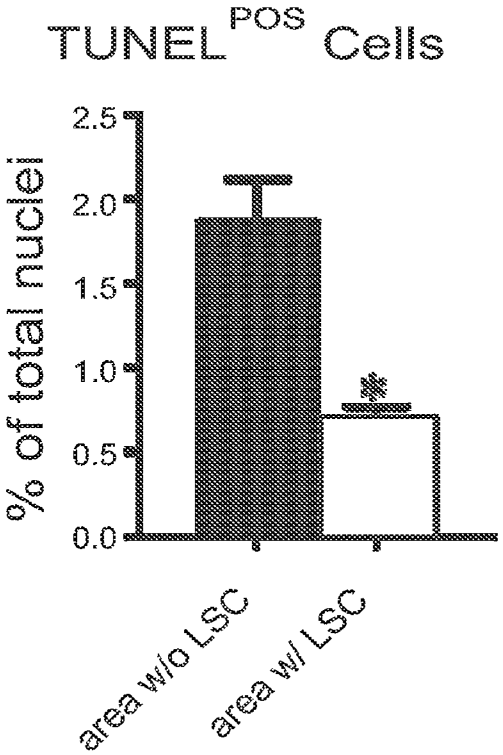
FIG. 5A(2)
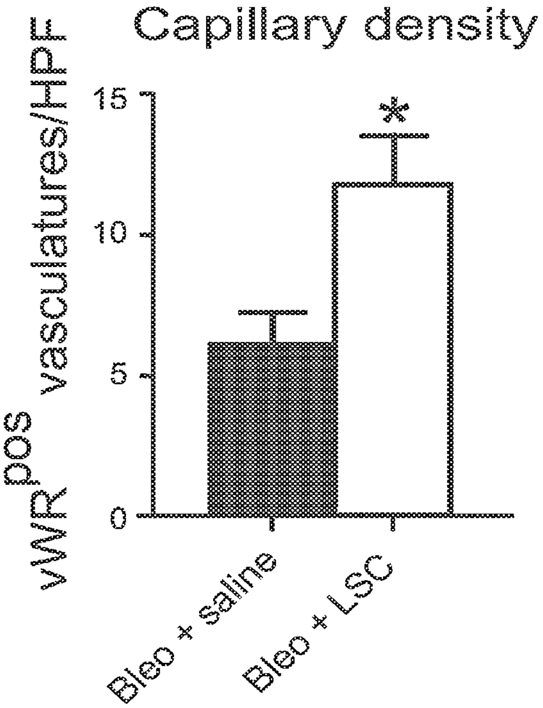
FIG. 5B

Bleo + LSC (EGFP)

LSC
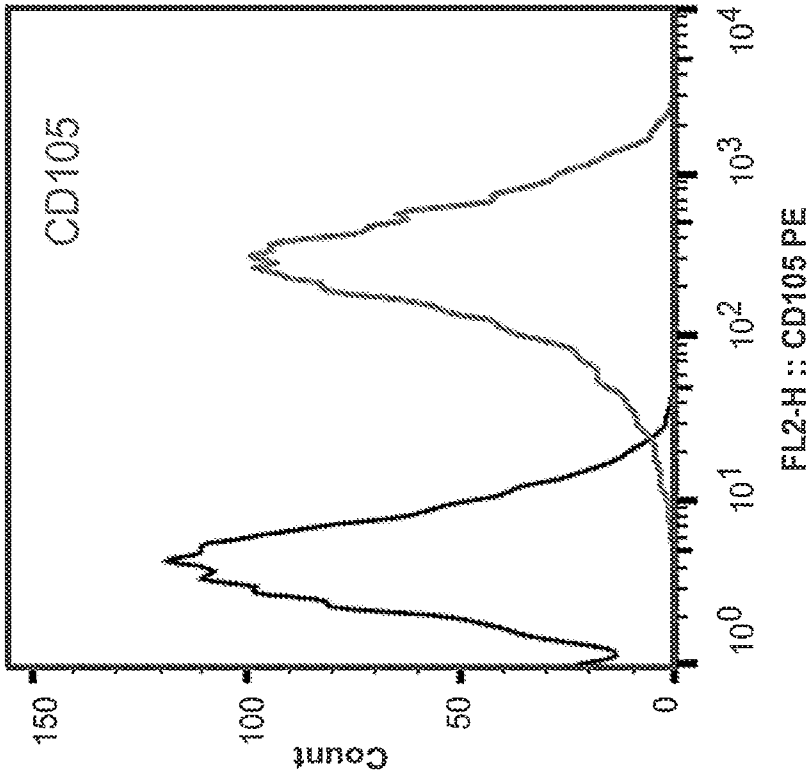
FIG. 7A(1)
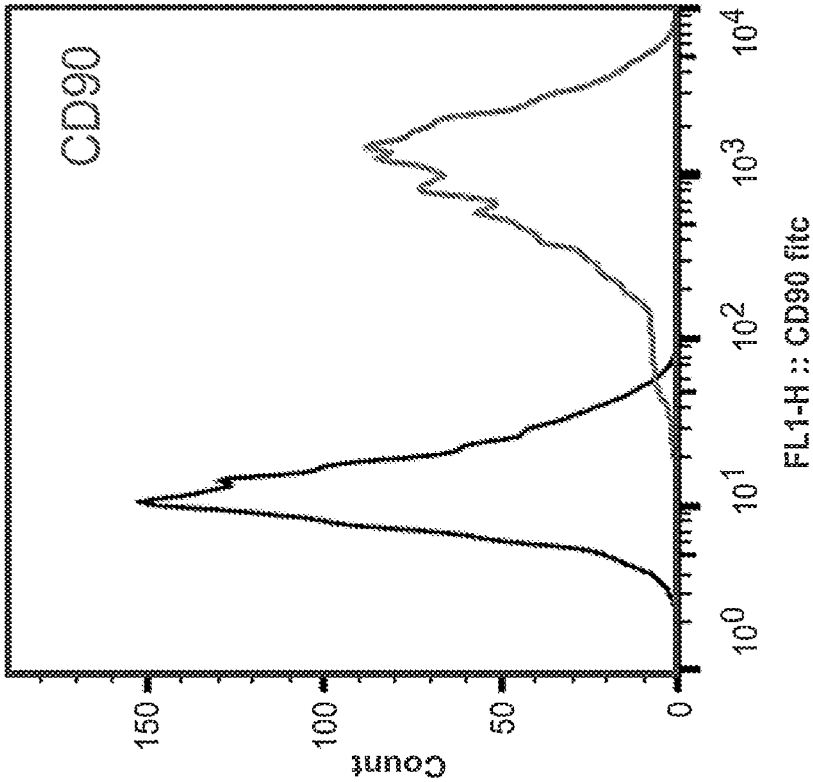
FIG. 7A(2)

LSC
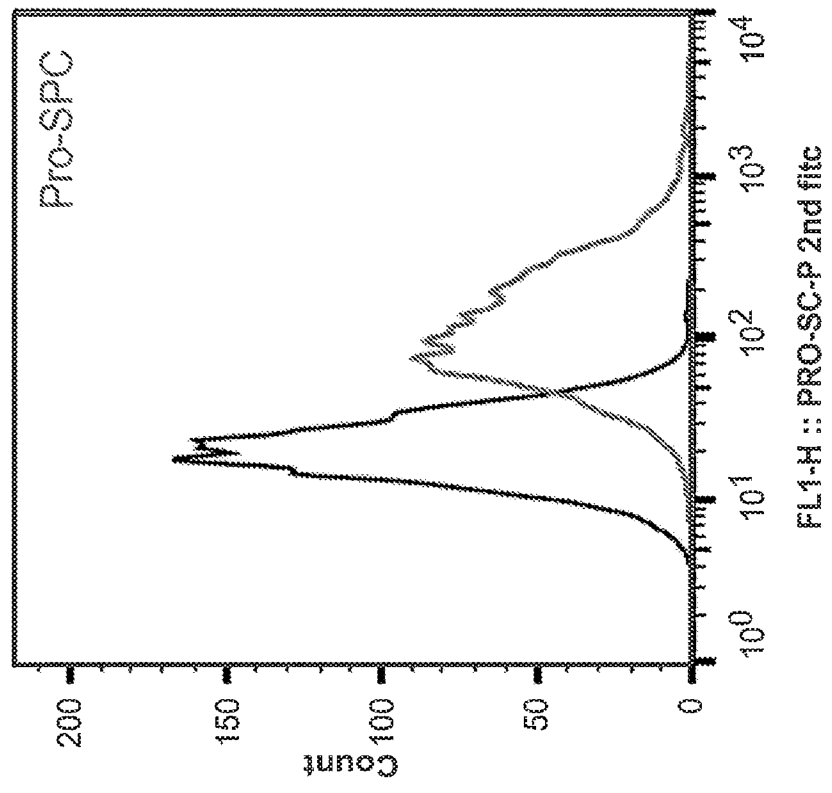
FIG. 7A(3)
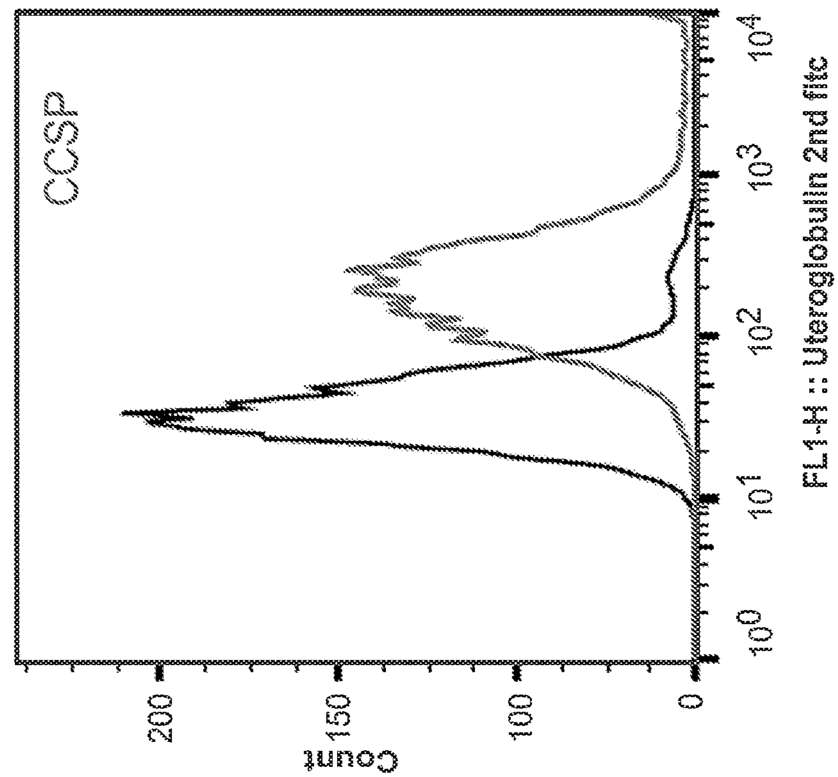
FIG. 7A(4)

BM-MSC
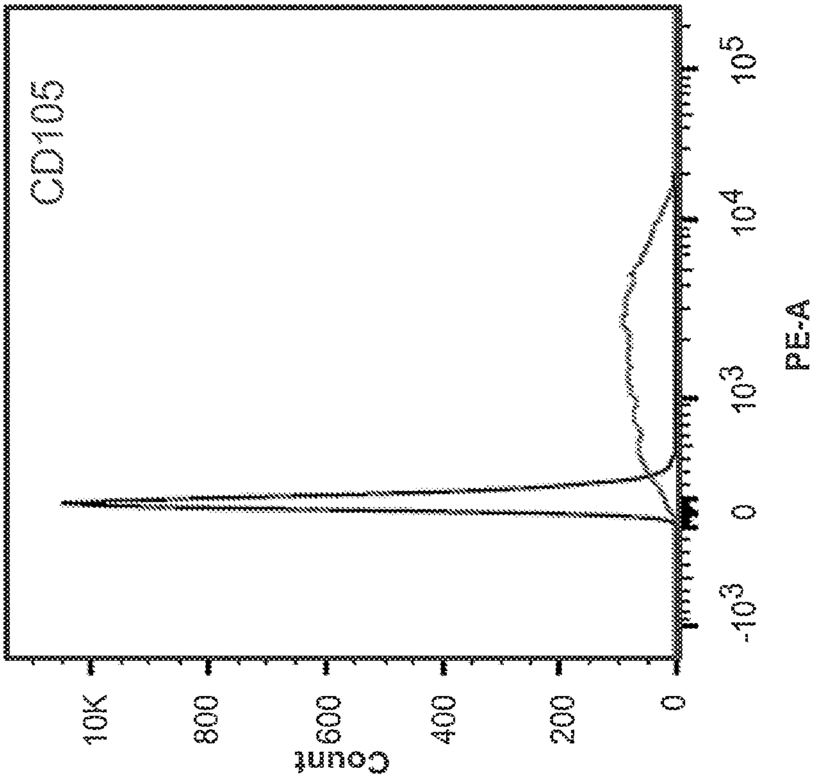
FIG. 7B(1)
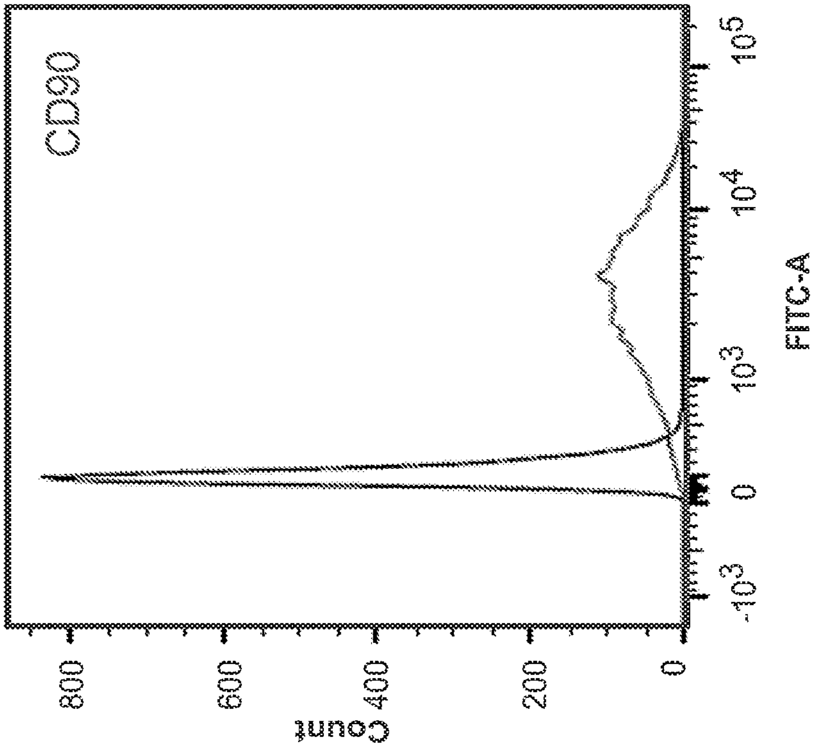
FIG. 7B(2)

BM-MSC
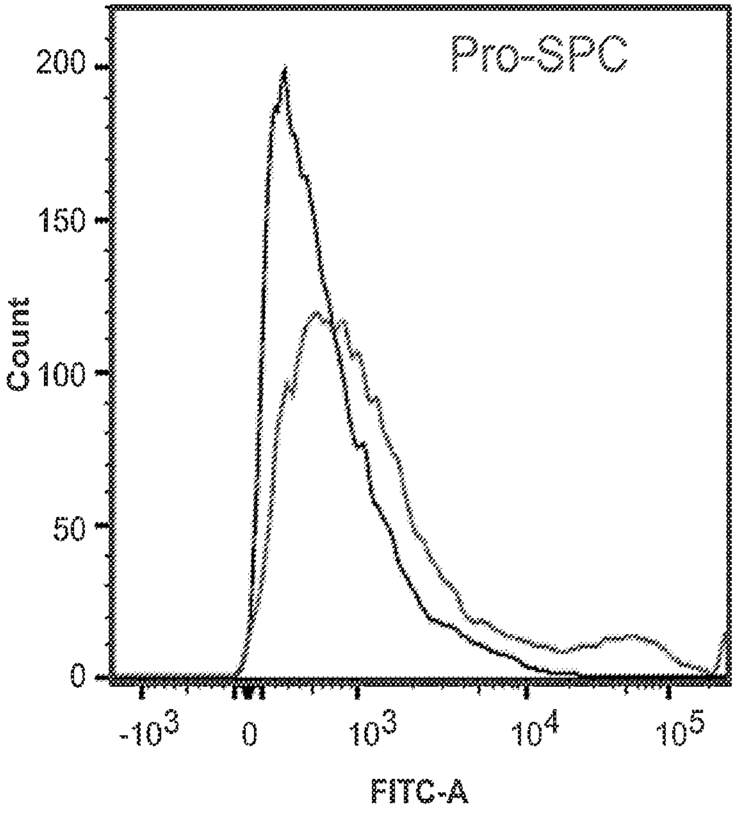
FIG. 7B(3)
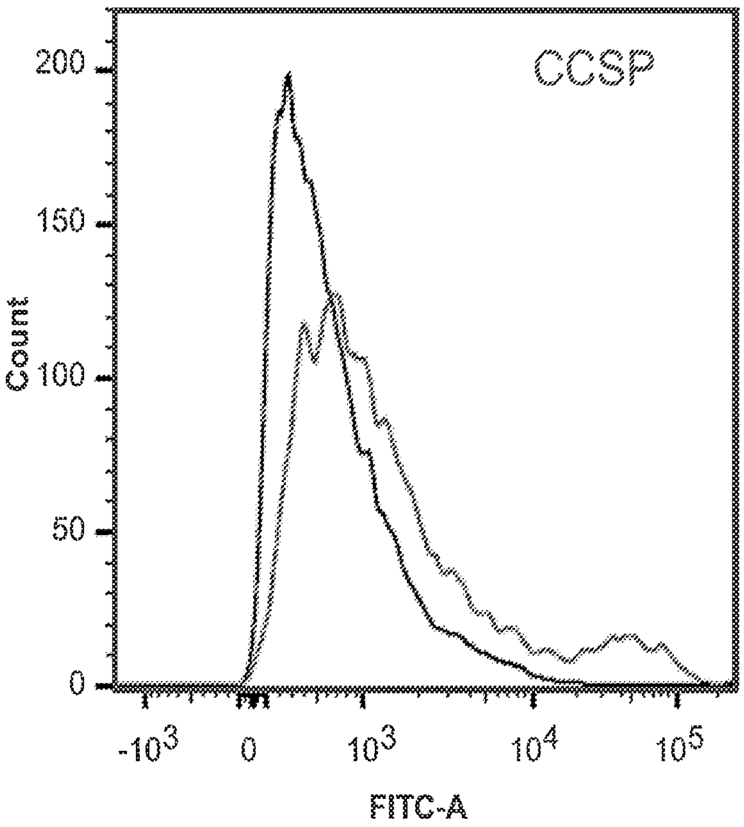
FIG. 7B(4)

EGF
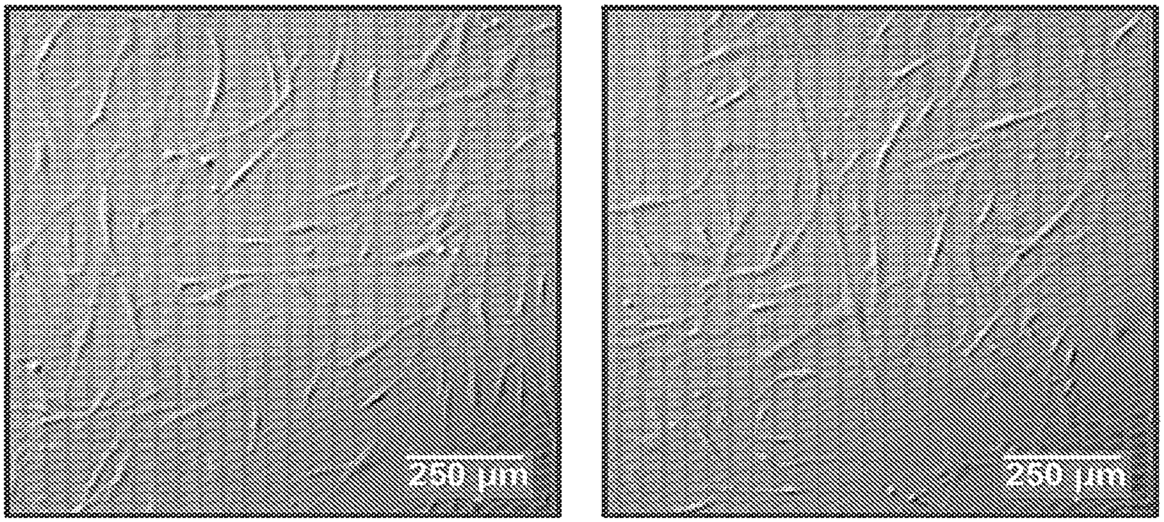
20% FBS
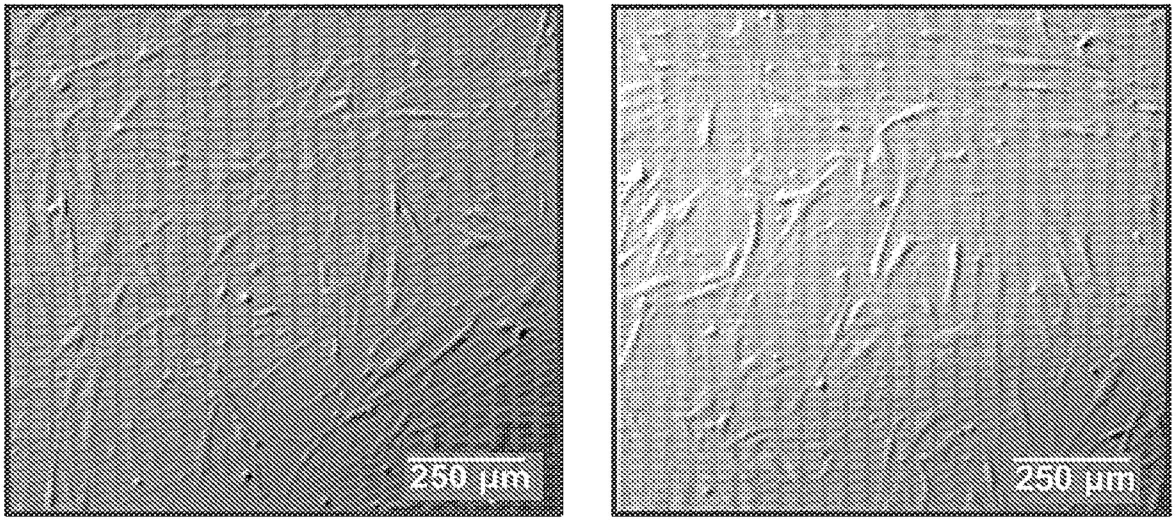
FIG. 15

MAMMALIAN LUNG SPHEROIDS AND LUNG SPHEROID CELLS AND USES THEREOF

CROSS REFERENCE TO RELATED APPLICATIONS

This application is a continuation of U.S. application Ser. No. 17/071,303 filed Oct. 15, 2020, which is a continuation of abandoned U.S. application Ser. No. 15/512,463 filed Mar. 17, 2017, which is a § 371 U.S. National Stage of International Application PCT/US2015/050835 filed Sep. 18, 2015, which claims benefit of 62/052,220 filed Sep. 18, 2014, which are hereby incorporated by reference in their entireties.

1. FIELD OF THE INVENTION

This invention relates generally to the discovery of novel mammalian lung spheroids and lung spheroid cells (LSCs) and uses thereof.

2. BACKGROUND OF THE INVENTION

2.1. Introduction

Lung diseases, such as chronic obstructive pulmonary disease (COPD) and idiopathic pulmonary fibrosis (IPF), are devastating conditions and according to the World Health Organization (WHO), in the top five causes of mortality worldwide [1]. Stem cell therapy is a promising approach to lung regenerative medicine [2]. Current preclinical and clinical efforts are focusing on the infusions of stromal cells isolated from human bone marrow, adipose tissue, placental tissue or cord blood (referred to either as mesenchymal stem cells or as marrow stromal cells) to treat patients with COPD, bronchopulmonary dysplasia, bronchiolitis obliterans, asthma or acute lung injury [3-5, 6, 7]}. Pluripotent cells such as embryonic stem cells or induced pluripotent stem cells hold great differentiation and proliferation potential but clinical translation is hampered by potential teratogenic risk in human trials [8-10]. On the other hand, a variety of resident lung stem cell types have been identified [11-16]. Compared to mesenchymal stem cells, isolation and expansion of these resident lung stem cells for clinical usage remain a challenge. Antigenic sorting and purification are normally required. Furthermore, it is yet to be determined which surface marker(s) identify the best cell sources of lung stem cells for regenerative therapies.

PCT Publication No. WO2012/047951 (Anversa et al.) report the discovery of lung stem cells that are c-kit positive and their uses for treating a lung disease or disorder.

Others have reported methods for isolated either stem cells or clusters of other cells such as cardiovascular cells. For example, U.S. Pat. No. 8,815,585 (Beardsley et al.) discloses an automated culture system for embryonic stem cells (ESCs) and their uses in therapy. US Patent Pub. No. 2010/0061966 (Marban et al.), Smith et al. 2007 Circulation 115 896-908, and Messina et al. 2004 Circ. Res. 95 911-921 disclose a method of making cardiospheres and cultures of cells derived from the cardiosphere cells. These cardiospheres are self-assembled aggregates of cells with some of the traits of cardiomyocytes, e.g., the ability to beat in vitro. They disclose the use of these cardiospheres for the treatment of a damaged and diseased organs such as the heart. The cardiospheres were prepared by culturing with media containing added growth factors, specifically basic fibroblast growth factor (bFGF), cardiotrophin-1, and epidermal growth factor (EGF).

3. SUMMARY OF THE INVENTION

Lung diseases are devastating conditions and ranked as one of the top five causes of mortality worldwide according to the World Health Organization. Stem cell therapy is a promising strategy for lung regeneration. Previous animal and clinical studies have been focused on the use of mesenchymal stem cells (from other parts of the body) for lung regeneration. This disclosure is directed to a rapid and robust method to generate therapeutic resident lung progenitors from adult lung tissues. Outgrowth cells from adult human lung tissues form self-aggregated into three-dimensional lung spheroids in a suspension culture. Without antigenic sorting/purification, lung spheroids recapitulate stem cell niche in vitro and contain a useful novel mixture of lung stem cells and supporting cells. In vitro, lung spheroid cells can be expanded to a large quantity and display potential to differentiate into alveolar structures and acquire mature lung epithelial phenotypes. In severe combined immunodeficiency mice with bleomycin-induced pulmonary fibrosis, intravenously-injected human lung spheroid cells inhibit apoptosis, fibrosis, and infiltration, but promote angiogenesis. In a syngeneic rat model of pulmonary fibrosis, lung spheroid cells (LSCs) outperform adipose-derived mesenchymal stem cells (MSCs) in reducing fibrotic thickening and infiltration. Our data suggest lung spheroid as a simple method to generate regenerative lung cells for lung diseases.

In particular non-limiting embodiments, the present invention provides a method for preparing therapeutically useful mammalian lung spheroids which comprises (i) culturing human lung tissue explant cells under adherent culture conditions to form a first lung cell outgrowth culture; (ii) culturing the first lung cell outgrowth culture under low-adherence conditions to form lung spheroid clusters; and (iii) recovering the therapeutically useful mammalian lung spheroids.

The invention also provides a method for preparing therapeutically useful mammalian lung spheroid cells which comprises (i) culturing human lung tissue explant cells under adherent culture conditions to form a first lung cell outgrowth culture; (ii) culturing the first lung cell outgrowth culture under low-adherence conditions to form lung spheroids; and (iii) culturing the lung spheroids under adherent culture conditions so as to form the therapeutically useful mammalian lung spheroid cells.

The invention provides methods for treatment. For example, it provides a method for the treatment of a lung disease in a mammalian patient which comprises providing to the patient a therapeutically effective amount of mammalian lung spheroids wherein the lung spheroids were prepared by (i) culturing a mammalian lung tissue explant under adherent culture conditions to for a first lung cell outgrowth culture; and (ii) culturing the first lung cell outgrowth culture under low-adherence conditions to form lung spheroids.

A method for the treatment of a lung disease in a mammalian patient which comprises providing to the patient a therapeutically effective amount of mammalian lung spheroid cells wherein the lung spheroid cells were prepared by (i) culturing a mammalian lung tissue explant under adherent culture conditions to for a first lung cell outgrowth culture; (ii) culturing the first lung cell outgrowth culture under low-adherence conditions to form lung spheroids; and (iii) culturing the lung spheroid clusters under adherent culture conditions so as to form the therapeutically useful mammalian lung spheroid cells.

A pharmaceutical composition comprising mammalian lung spheroids prepared from mammalian lung tissue wherein (a) the lung spheroids have a diameter of about 25 μM to about 500 μM; (b) (i) are negative or slightly positive for c-Kit; (ii) negative for at least one hematopoietic marker; and (iii) at least one cardiosphere marker; and (c) a pharmaceutically acceptable carrier.

A pharmaceutical composition comprising mammalian lung spheroid cells prepared from mammalian lung tissue wherein (a) are slightly positive or negative for (i) c-Kit; (ii) negative for at least one hematopoietic marker; and (iii) negative for at least one cardiosphere marker; and (b) a pharmaceutically acceptable carrier.

In the methods or compositions above, the mammalian lung spheroids or lung spheroid cells may be human lung spheroids or human lung spheroid cells. The adherent culture conditions in step (i) may be a glycoprotein-coated, a protein-coated, or a proteoglycan-coated surface such as a collagen-coated surface, a fibronectin-coated surface, a laminin-coated surface or an uncoated plastic surface. The low-adherence conditions comprise a bioreactor or a neutrally-charged hydrogel-coated surface or any surface resistant to cell attachment.

In one embodiment, the mammalian lung spheroids or lung spheroid cells may be (i) positive for antibodies to CCSP, CD105, CD90, and Pro-SPC; and (ii) negative for antibodies to hematopoietic markers.

In one embodiment, the LSCs are positive by FACs for the following markers in the following percentages: CD105: 50-100%; CD90: 0-100%; Pro-SPC: 5-100%; CCSP: 5-100%. In another embodiment, the LSCs are CD105: 50-75%; CD90: 0-50%; Pro-SPC: 5-50%; CCSP: 5-50%. In yet another embodiment, the LSCs are CD105: 75-100%; CD90: 50-100%; Pro-SPC: 50-100%; CCSP: 50-100%.

In one embodiment, the culturing conditions may comprise a media that consists essentially of Iscove's Modified Dulbecco's Media (IMDM) and fetal bovine serum (FBS).

The invention also provides a pharmaceutical composition comprising the lung spheroids or lung spheroid cells obtained according to the method as defined i herein, at a concentration comprised between $90\text{-}250\times10^3$ cells/ml, preferably $100\text{-}120\times10^3$ cells/ml, as active principle, together with pharmacologically acceptable adjuvants and/or excipients, said composition being formulated for intravenous injection.

In the treatment methods, the mammalian patient may be a human patient or a veterinary patient. The treatment may be an allogeneic treatment, an autologous treatment or a xenogeneic treatment.

The lung disease may be a chronic lung disease or an acute lung disease. Non-limiting examples of chronic lung diseases include asthma, chronic obstructive pulmonary disease (COPD), cystic fibrosis, emphysema, lung cancer and pulmonary fibrosis. Non-limiting examples of acute lung diseases include a bacterial pneumonia, a bronchiolitis obliterans organizing pneumonia (BOOP), a chemical pneumonia, a viral pneumonia, or a mixture thereof.

In the methods above, the mammalian lung spheroids or lung spheroid cells may be delivered by aerosol, direct injection into the lung, intranasally, intraperitoneally, or intravenously. The mammalian lung spheroids or lung spheroid cells may be delivered together with biomaterials or other carriers that can help the cells to engraft in the lung.

The invention also provides method of identifying a compound that prevents or treats a lung disorder, the method comprising the steps of: (a) contacting a compound with a sample comprising a lung spheroid or lung spheroid cells; (b) measuring a level of a gene, a protein or a metabolite associated with the lung disorder; and (c) determining a functional effect of the compound on the level of the gene, the protein, or the metabolite; thereby identifying a compound that prevents or treats the lung disorder.

4. BRIEF DESCRIPTION OF THE FIGURES

Figure 1B:
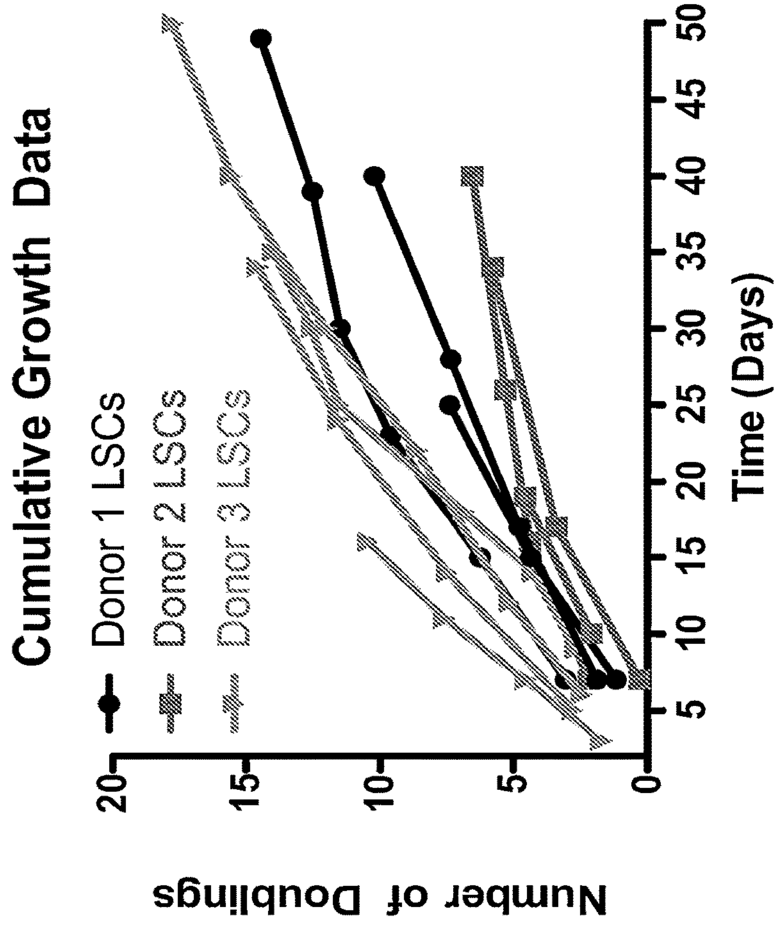
Figure 1C:
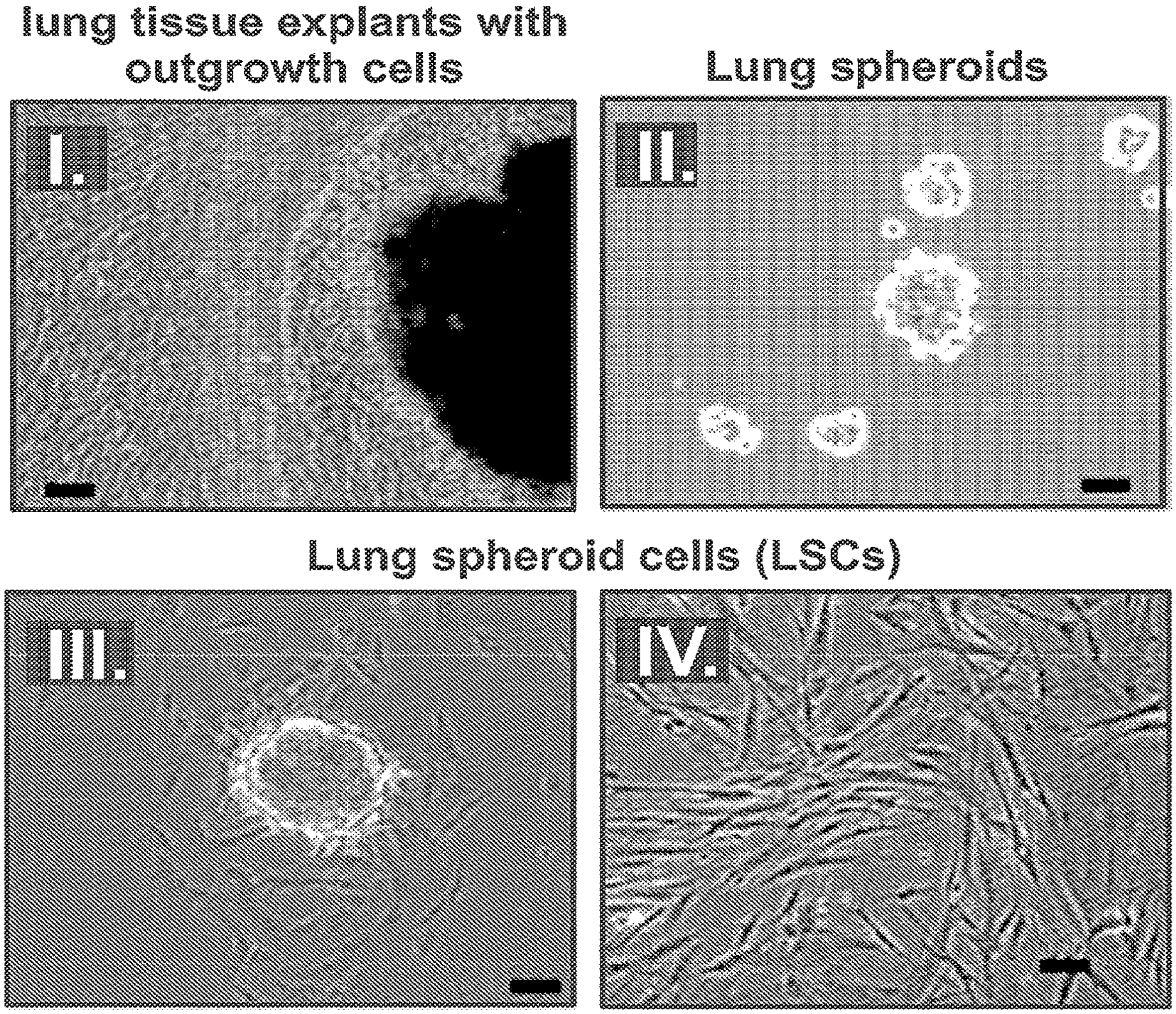
Figure 1D:
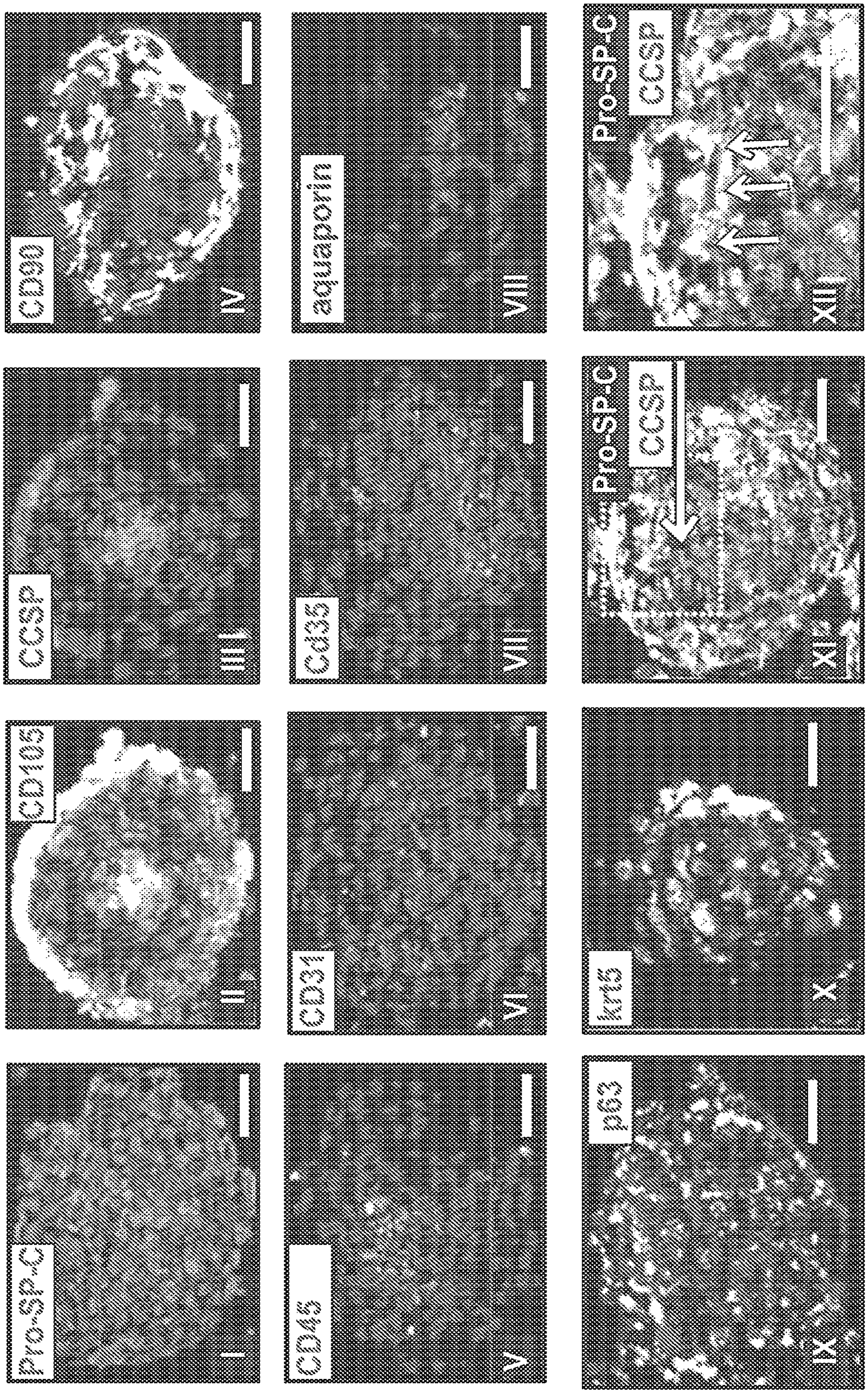

FIGS. 1A-1D. Generation and characterization of lung spheroids and lung spheroid cells. FIG. 1A. Schematic showing the protocol to grow lung spheroids and lung spheroid cells. FIG. 1B. Cumulative doublings for LSCs from three different donors. FIG. 1C Panel I. Edge of lung tissue explants with outgrowth cells becoming confluent and ready to harvest. FIG. 1C Panel II. Lung spheroids formed from outgrowth cells in suspension culture. FIG. 1C Panel III. Plated lung spheroids onto fibronectin-coated surfaces to generate lung spheroid cells (LSCs). FIG. 1C Panel IV. Expansion of LSCs in suspension cultures. FIG. 1D. Immunocytochemistry on lung spheroids. The arrows in FIG. 1D, panels XI and XII, indicate CCSP positive cells. Scale bars=50 μm.

Figure 2B:
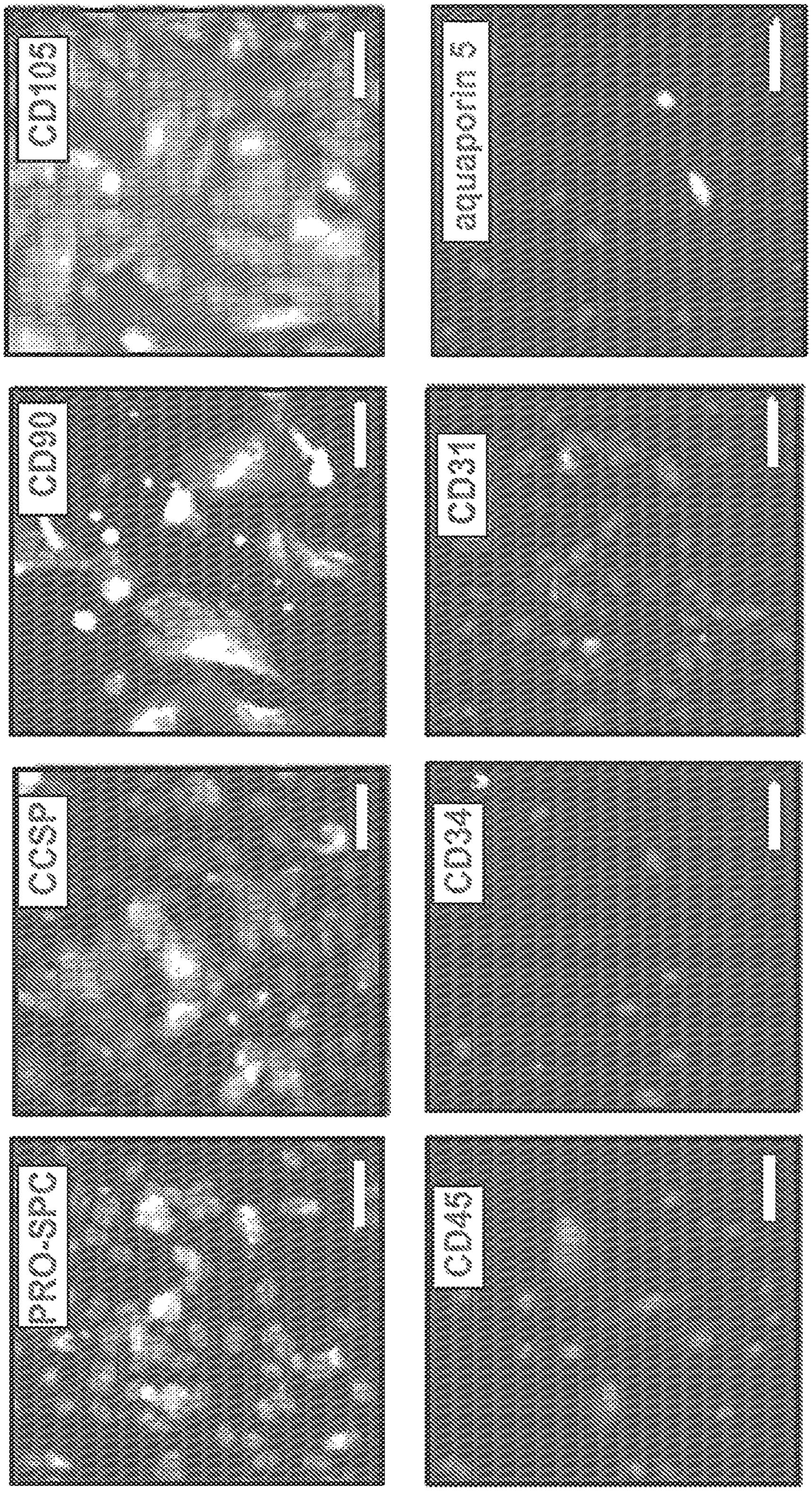
Figure 2C:
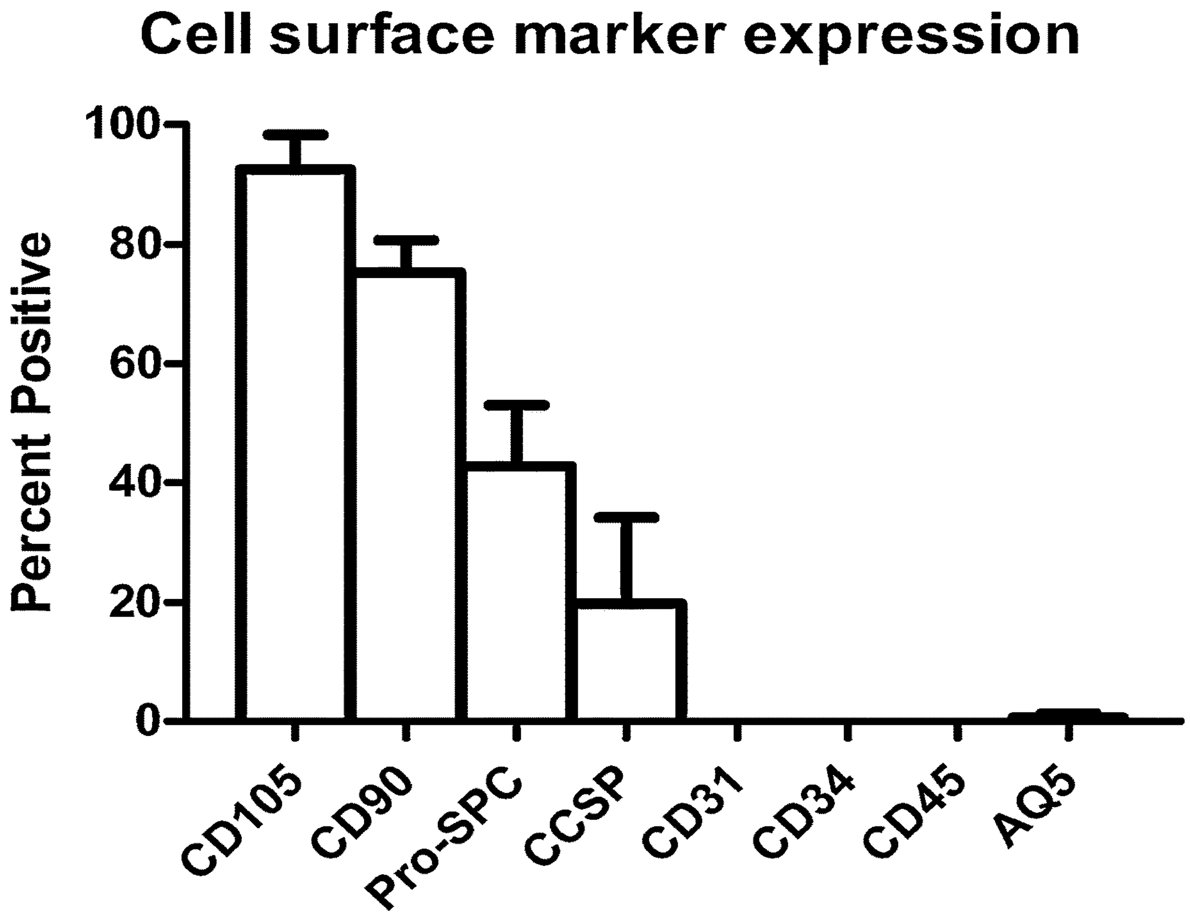
Figure 2D:
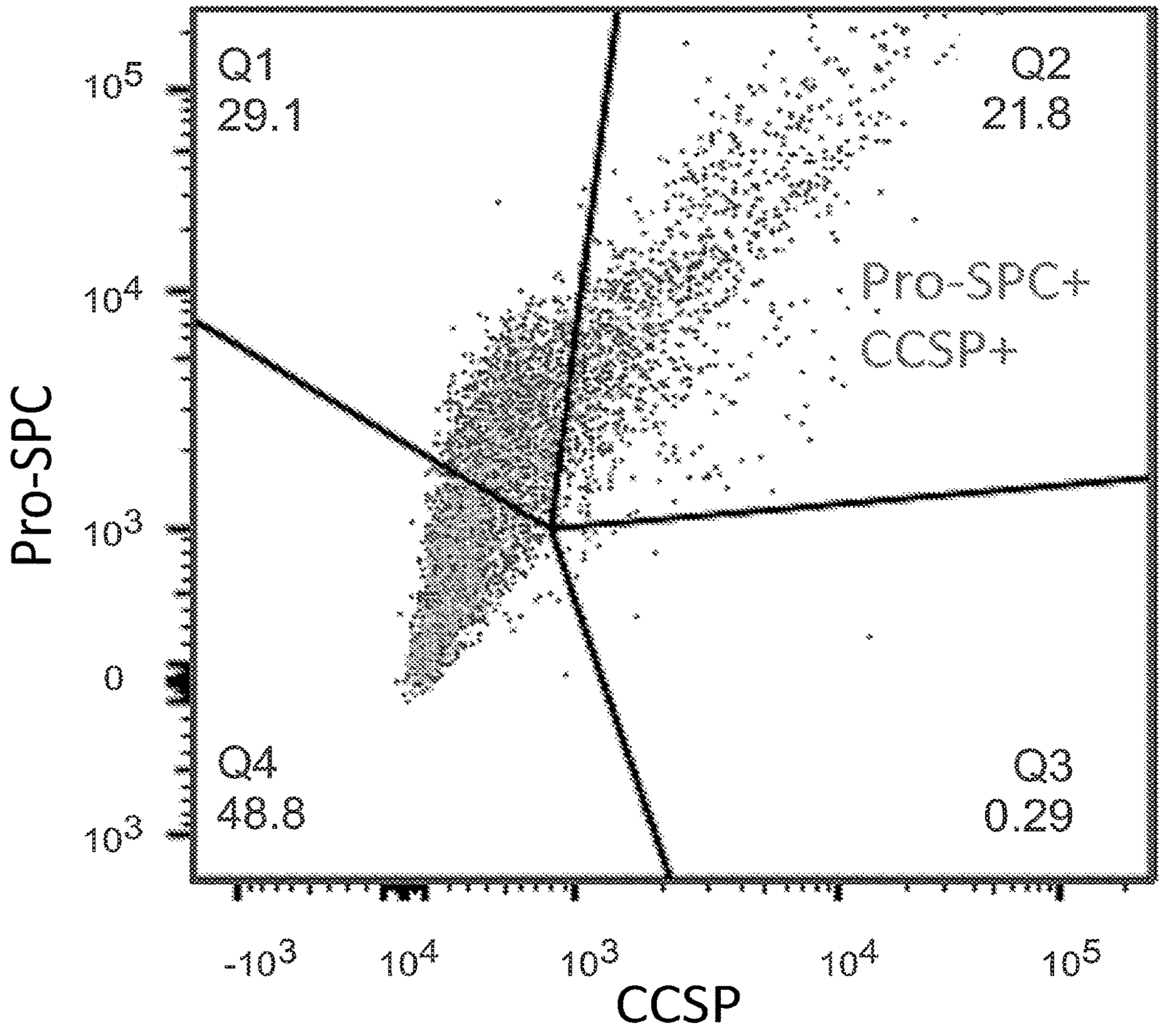

FIGS. 2A-2D. Lung spheroid cells contain lung progenitor cells. FIGS. 2A(1)-2A(8), Representative flow cytometry plots of LSCs for expression of CD31, CD34, CD45, CD90, CD105, CCSP, Pro-SPC, and aquaporin 5. Black lines: isotype controls. Gray lines: antibodies. FIG. 2B. Immunocytochemistry staining of LSCs for the aforementioned markers. FIG. 2C. Pooled data for the expressions of aforementioned markers (n=3 lung donors). FIG. 2D. Double staining of Pro-SPC and CSSP in LSCs.

Figures 3A, 3B:
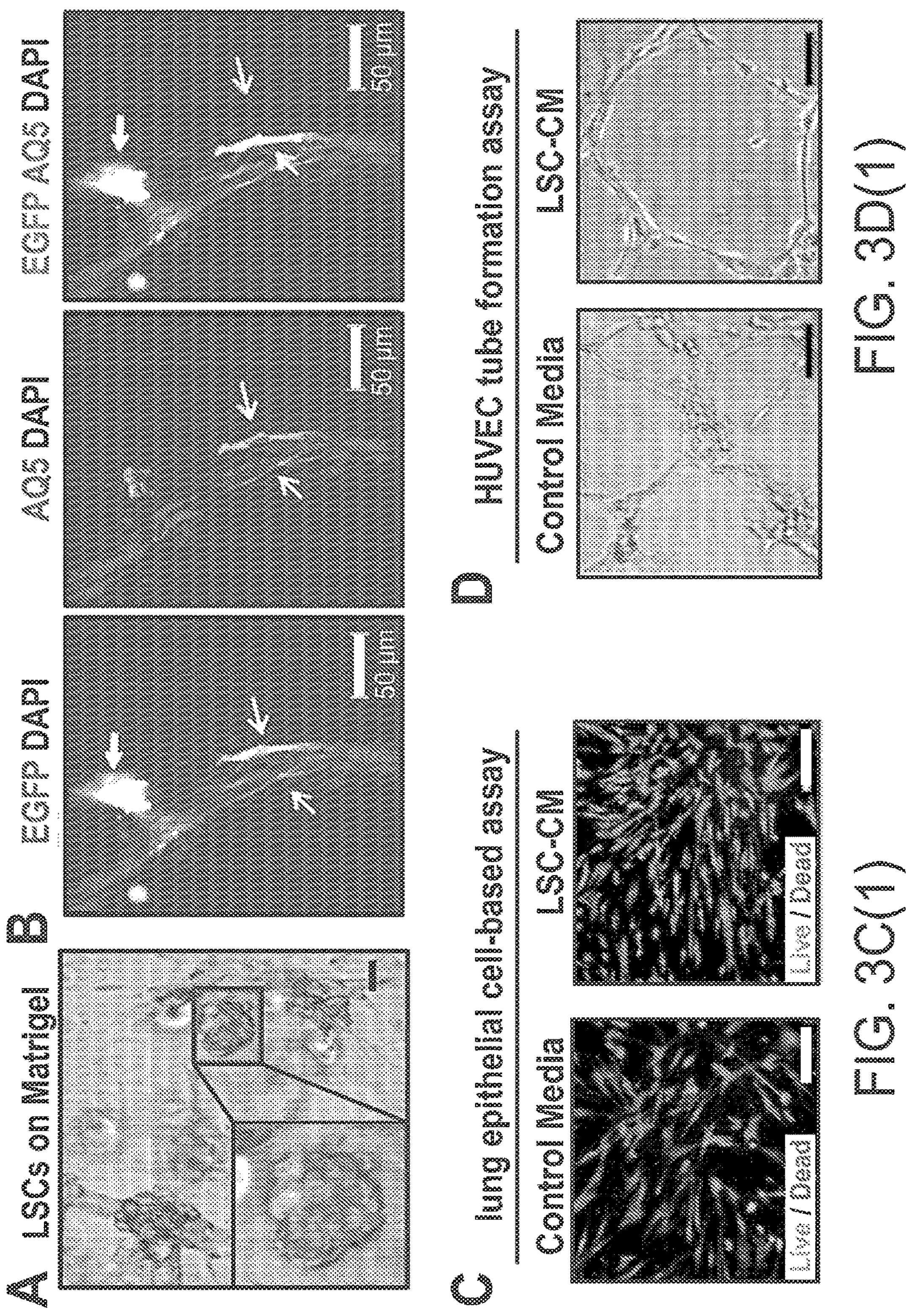
Figure 3E:
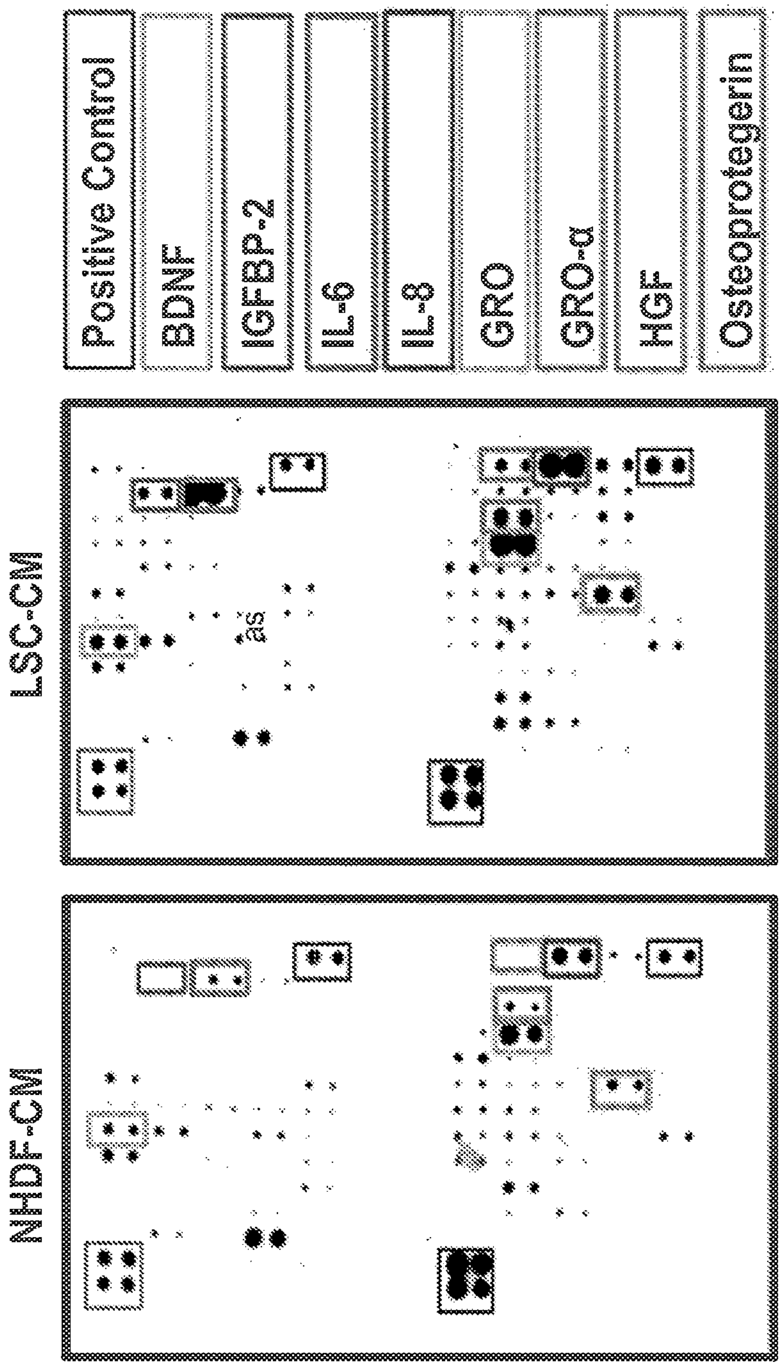

FIGS. 3A-3E. In vitro differentiation and paracrine assays of lung spheroid cells. FIG. 3A. LSCs grown on Matrigel™ and displaying alveoli-like structures (inset). FIG. 3B. LSCs grown on Matrigel™ expressed aquaporin 5 (white). FIG. 3C. Human lung epithelial cells cultured in Control media and LSC-conditioned media (CM) and stained for live/dead assay. FIG. 3D. Human umbilical vein endothelial cells (HUVEC) tube formation assay on Matrigel surface, in control media or conditioned medial from LSCs. Data are presented as Mean±S.D. All experiments are run in triplicates unless noted otherwise. Scale bars=50 μm. * indicates $p<0.05$ when compared to the "Control Media" group. FIG. 3E. Representative antibody array images showing the proteins presenting in the CMs from LSCs and NHDF cells.

Figure 4A:
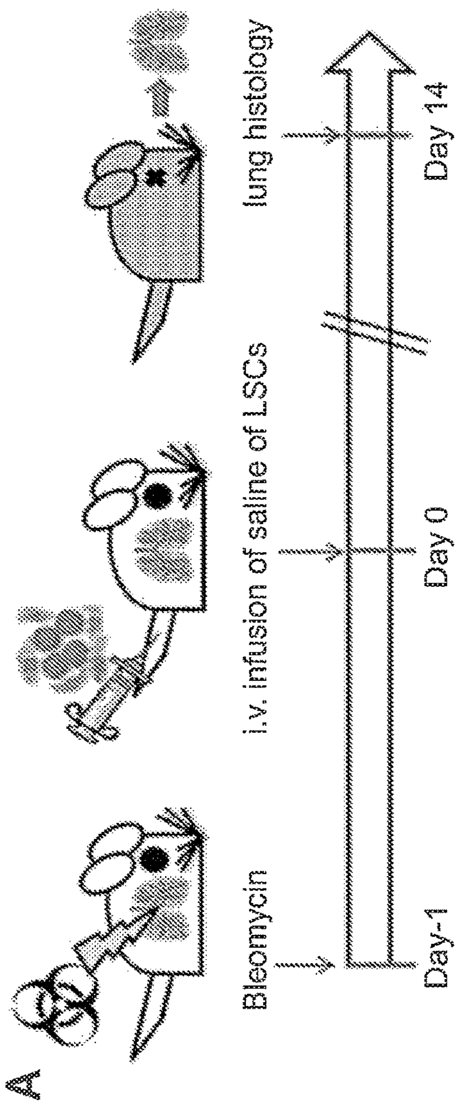
Figure 4B:
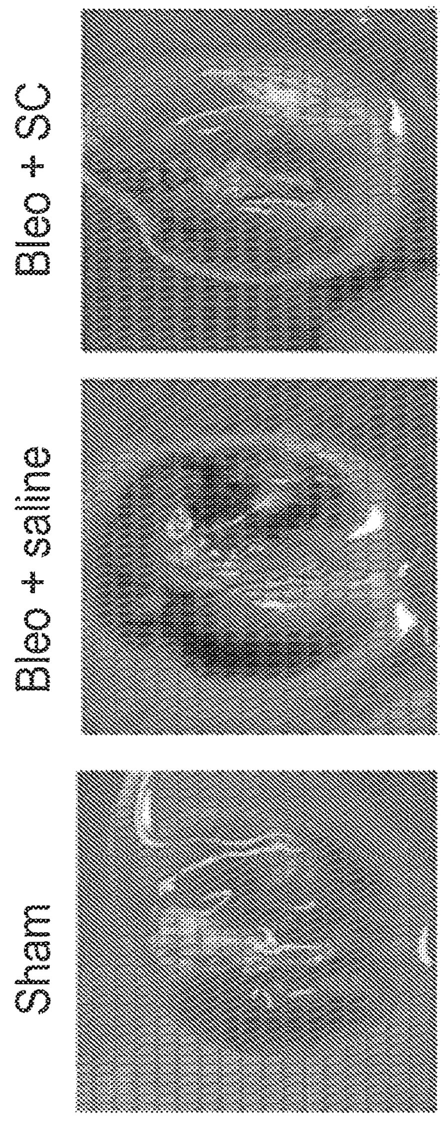
Figure 4C:
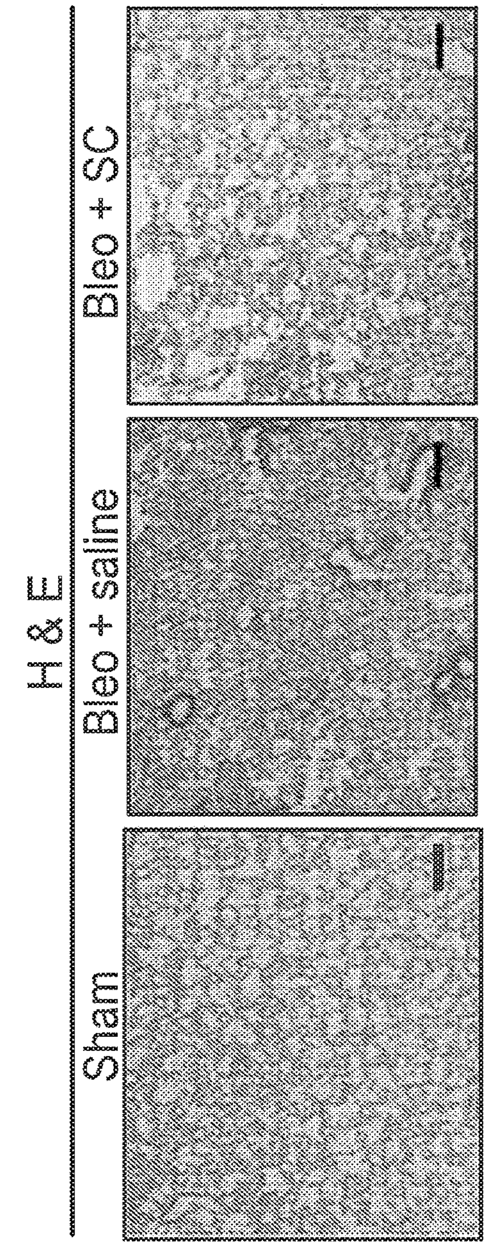
Figure 4D:
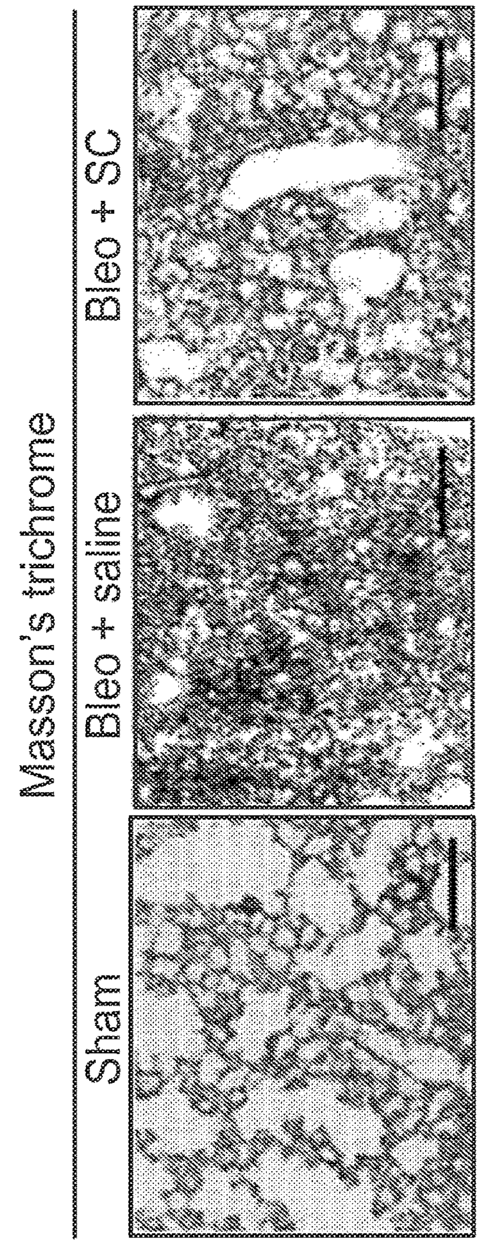
Figure 4E:
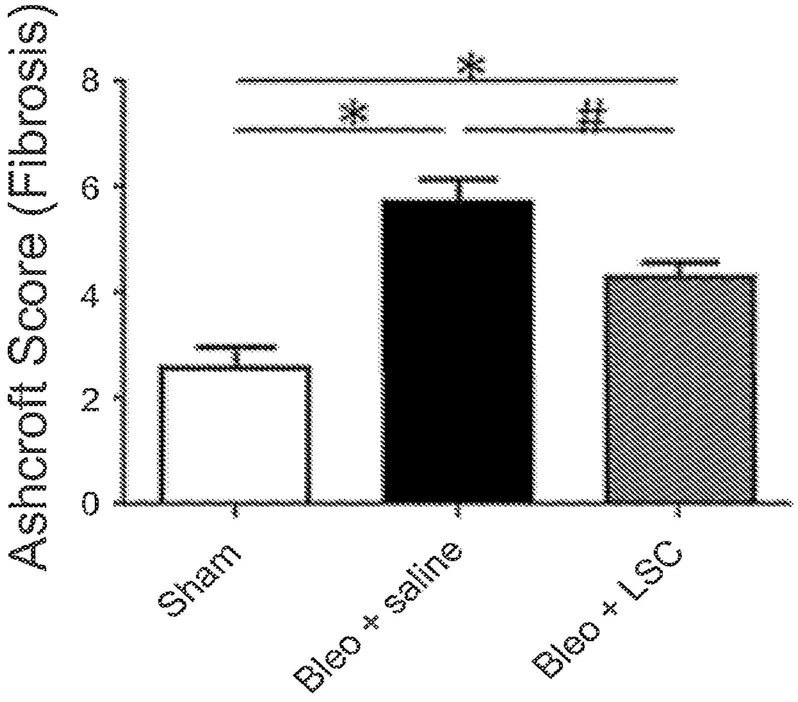
Figure 4F:
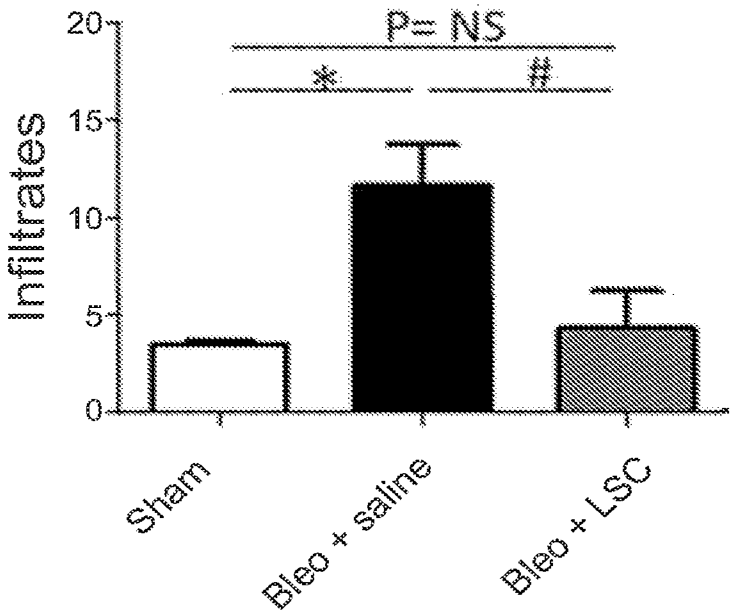

FIGS. 4A-4F. Therapeutic benefits of human LSCs in mice with bleomycin-induced pulmonary fibrosis. FIG. 4A. A schematic showing the design of mouse studies. FIG. 4B. Macroscopic views of explanted lungs 14 days after LSC or saline treatment. Hematoxylin & eosin staining (FIG. 4C) and Masson's trichrome staining (FIG. 4D) are performed on the lungs. FIG. 4E. Quantitation of fibrous thickening by Ashcroft score from the H&E staining images (n=6-7 animals per group). FIG. 4F. Quantitation of tissue infiltrates from the H&E staining images (n=6-7 animals per group). Data are presented as Mean±S.D. Scale bars=100 μm. * indicates $p<0.05$ when compared to the "Sham" group; # indicates $p<0.05$ when compared to the "Bleo+saline" group.

Figure 5C:
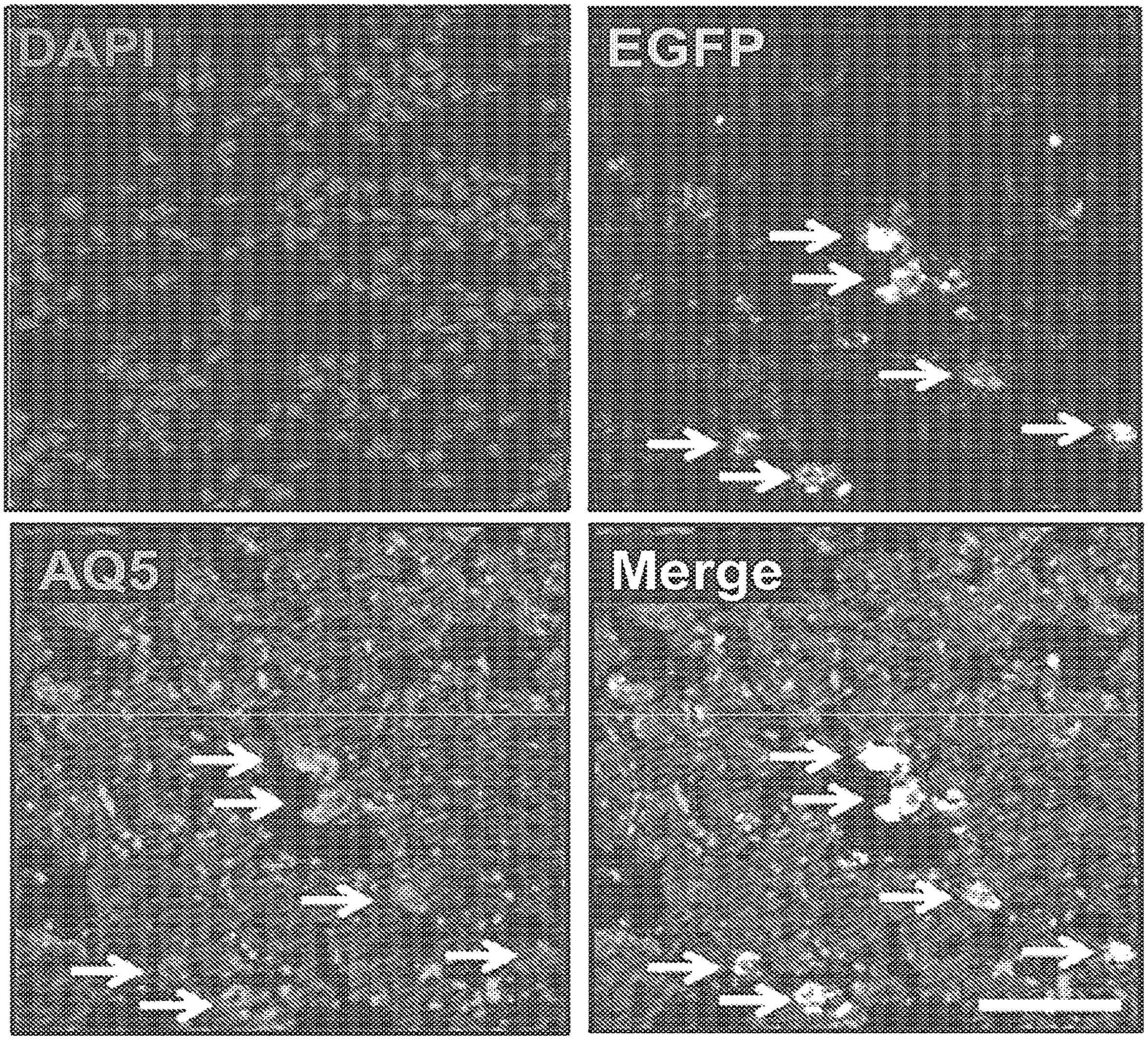
Figure 5D:
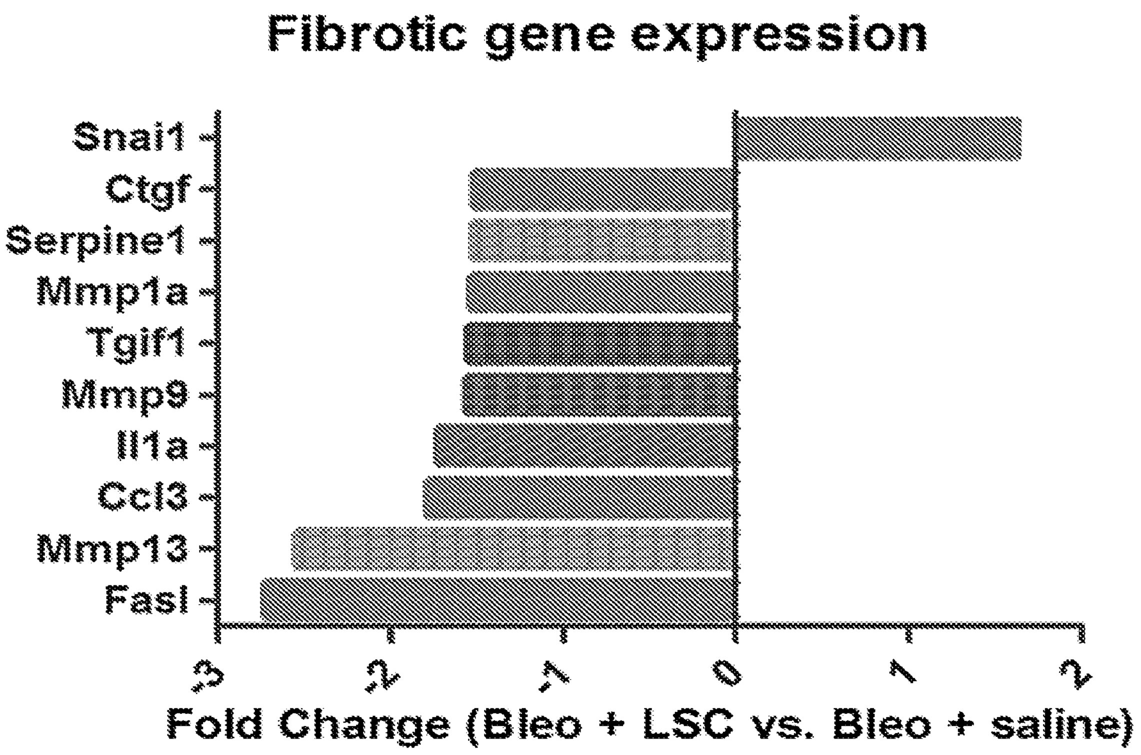
Figure 5E:
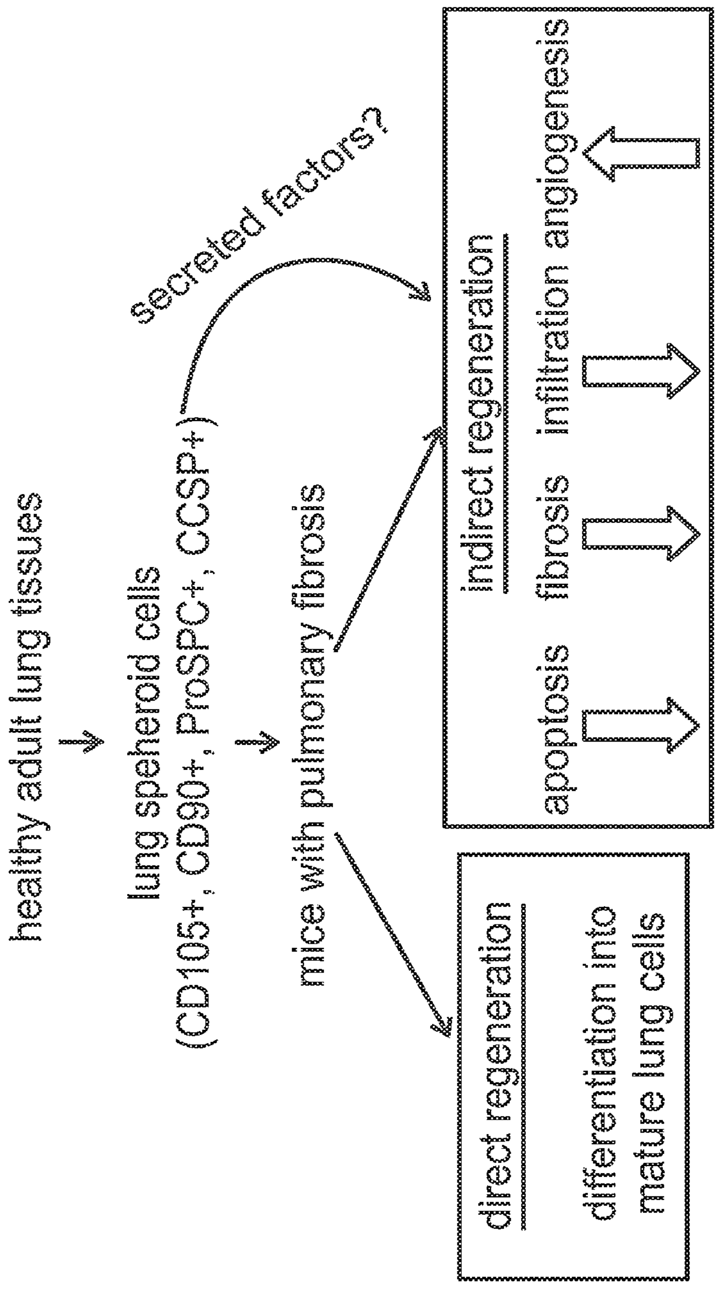

FIGS. 5A-5E. Mechanisms underlying the therapeutic effects of LSCs in pulmonary fibrosis. FIG. 5A(1). Representative confocal images showing the numbers of apoptotic cells (white nuclei, arrows) in area with and without LSC engraftment and quantitation FIG. 5A(2) (n=4 animals per group). FIG. 5B. Representative data showing increased angiogenesis in bleomycin-treated lungs (more vWF-positive vasculatures were detected in the LSC-treated lungs (Bleo+saline vs. Bleo+LSC: 6.0±2.3 vs. 11.8±3.3 per HPF; n=4 animals per group). FIG. 5C. Representative confocal images showing engrafted EGFP-positive (white arrows) LSCs co-express mature lung epithelial cell markers aquaporin 5 (white arrows). FIG. 5D. qPCR expression levels of fibrosis-related genes in lungs treated with saline or LSCs. FIG. 5E. Proposed mechanisms and markers for LSC-mediated lung repair in pulmonary fibrosis. Data are presented as Mean±S.D. Scale bars=20 μm. * indicates $p<0.05$ using unpaired Student's t tests.

Figure 6A:
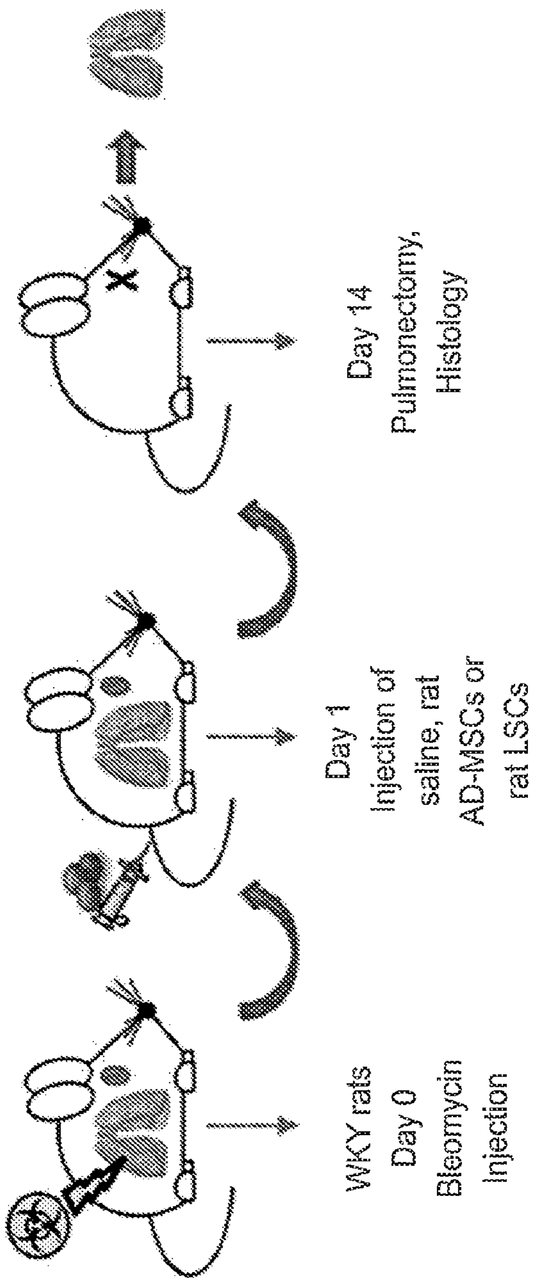
Figure 6B:
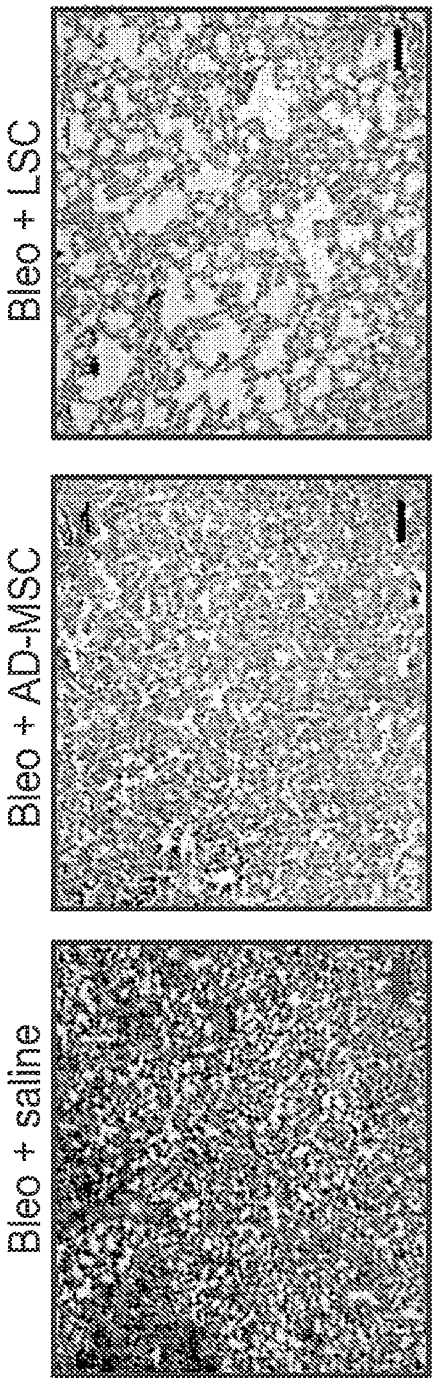
Figure 6C:
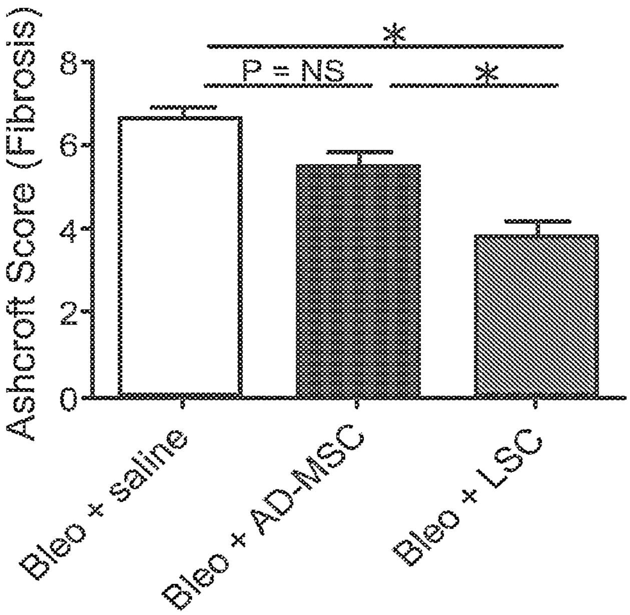
Figure 6D:
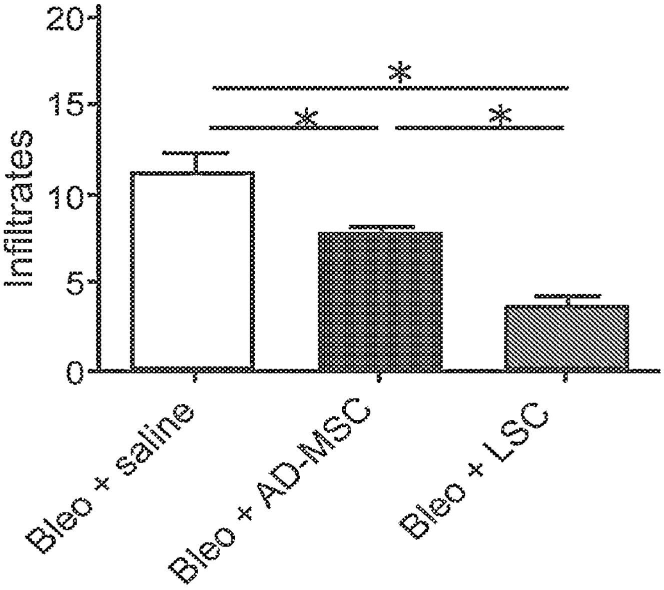

FIGS. 6A-6D. Therapeutic superiority of LSCs over AD-MSCs. FIG. 6A. A schematic showing the design of rat studies. FIG. 6B. Hematoxylin & eosin staining of rat lung sections 14 days after treatment with saline, AD-MSCs, or LSCs. FIG. 6C. Quantitation of fibrous thickening by Ashcroft score from the H&E staining images (n=5 animals per group). FIG. 6D. Quantitation of tissue infiltrates from the H&E staining images (n=5 animals per group). Data are presented as Mean±S.D. Scale bars=100 μm. * indicates $p<0.05$ in comparison.

FIGS. 7A(1)-7B(4). Distinction between human LSCs (FIGS. 7A(1)-7A(4)) and BM-MSCs (FIGS. 7B(1)-7B(4)) in surface marker expression. While expressing CD105 and CD90, MSCs do not express pro-SPC and CCSP.

Figure 8A:
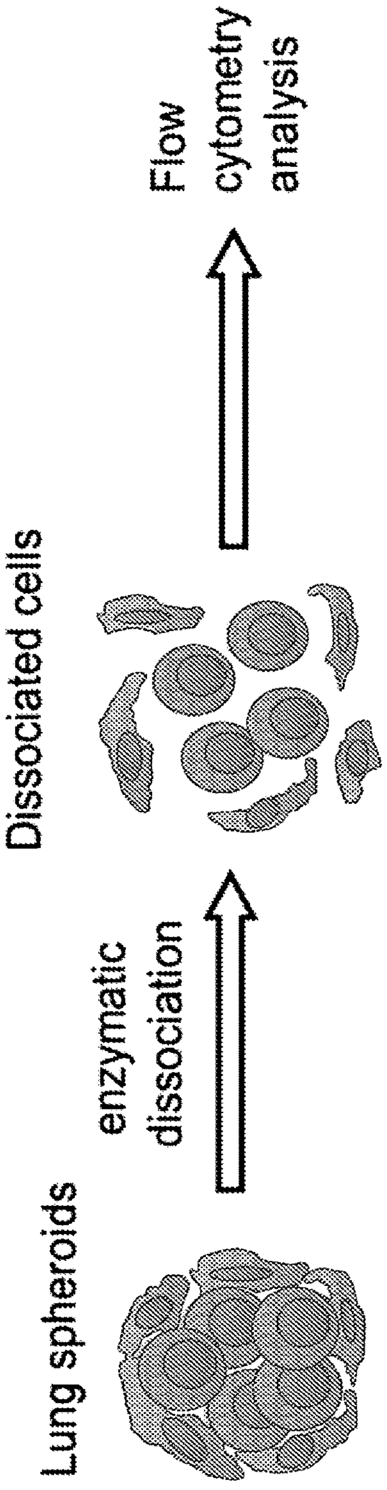
Figure 8B:
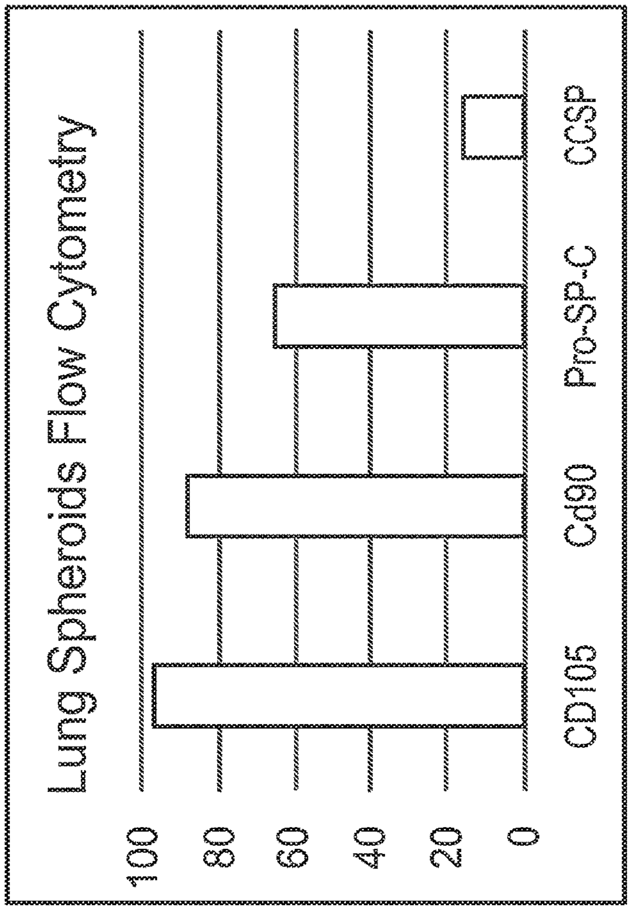
Figure 8C:
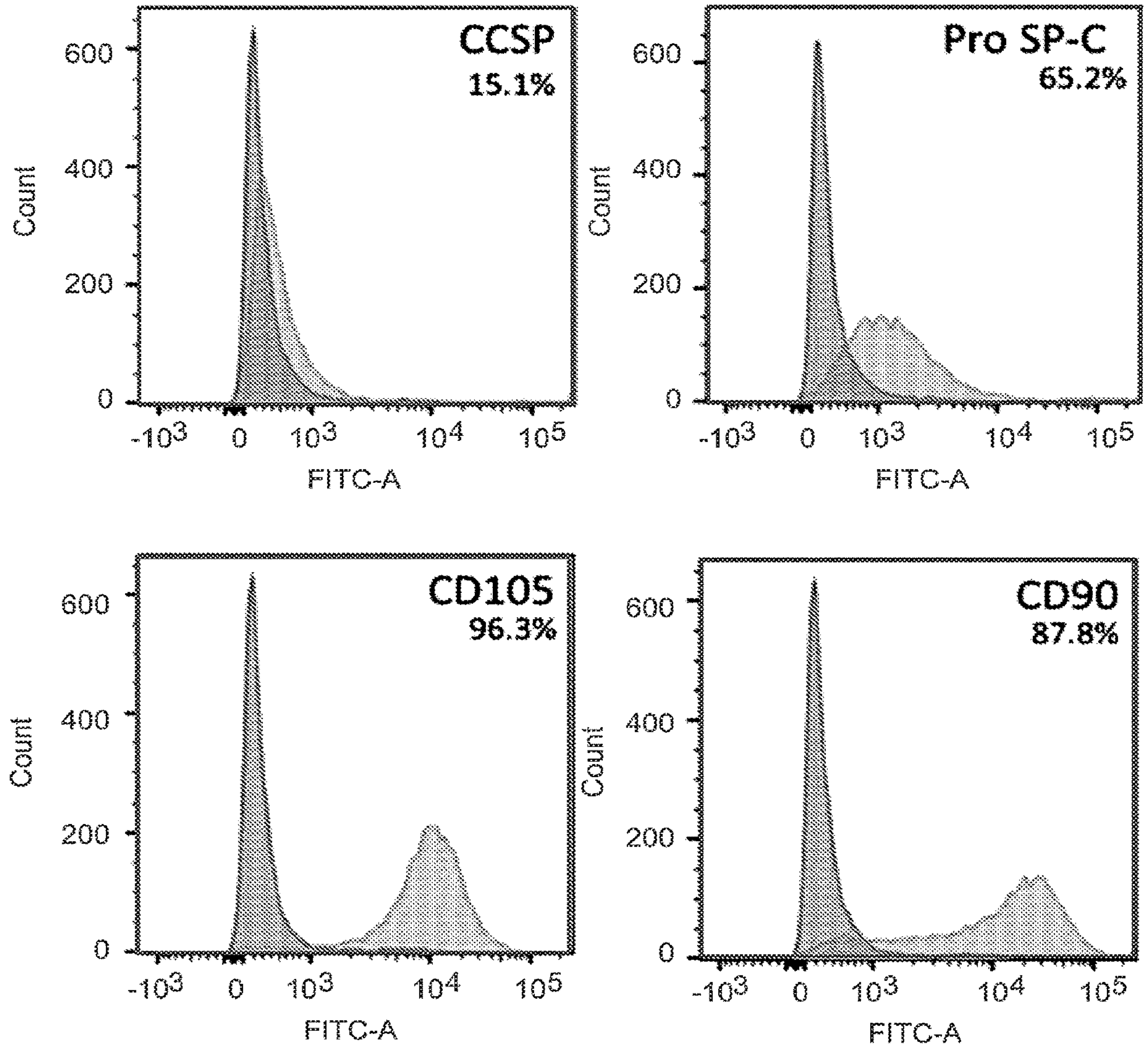

FIGS. 8A-8C. Flow cytometry analysis of cell phenotypes in lung spheroids. FIG. 8A. Flow cytometry schematic. FIG. 8B. Flow cytometry of the dissociated cells for different markers. FIG. 8C. Bar chart showing the relative expression of CD105, CD90, Pro-SPC and CCSP. Lung spheroids were dissociated into single cells by 30 min of incubation in TryPEL Select™ and then analyzed for expression of CD105, CD90, Pro-SPC and CCSP.

Figure 9:
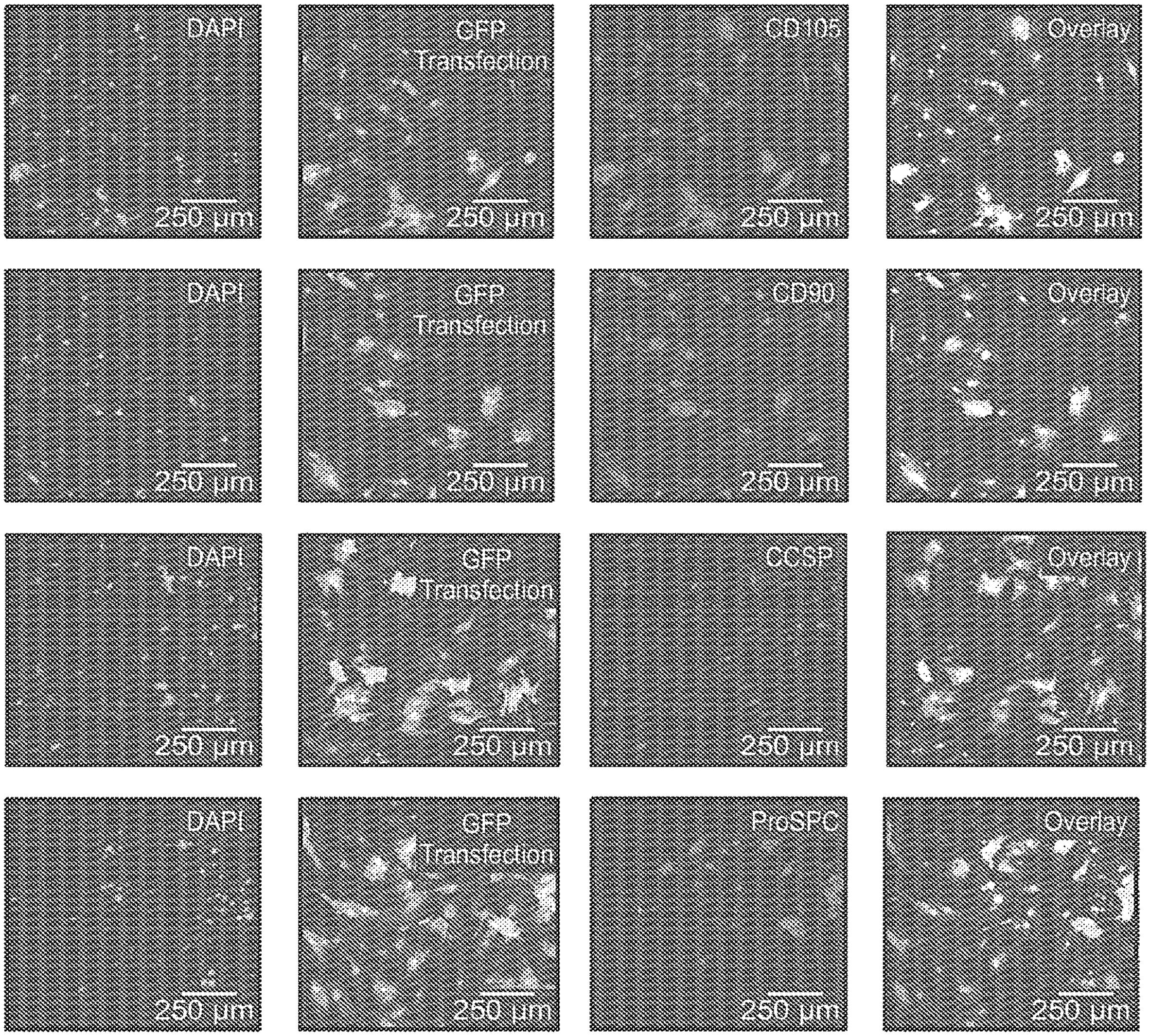

FIG. 9. Expression of CD105, CD90, Pro-SPC, and CCSP in LSCs transduced with EGFP viral particles.

Figure 10:
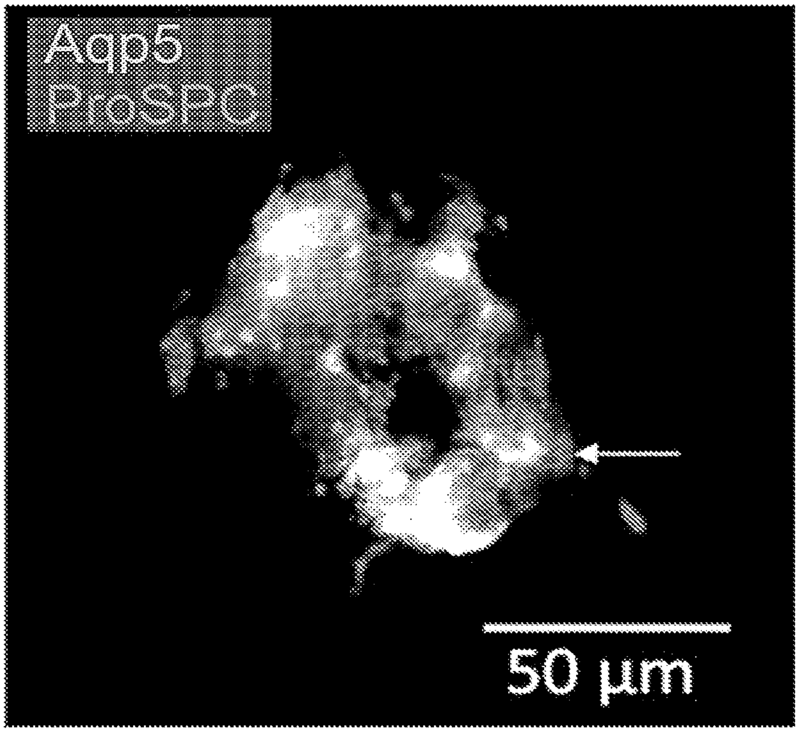

FIG. 10. Expression of Aquaporin 5 and Pro-SPC in LSCs cultured on Matrigel.

Figure 11:
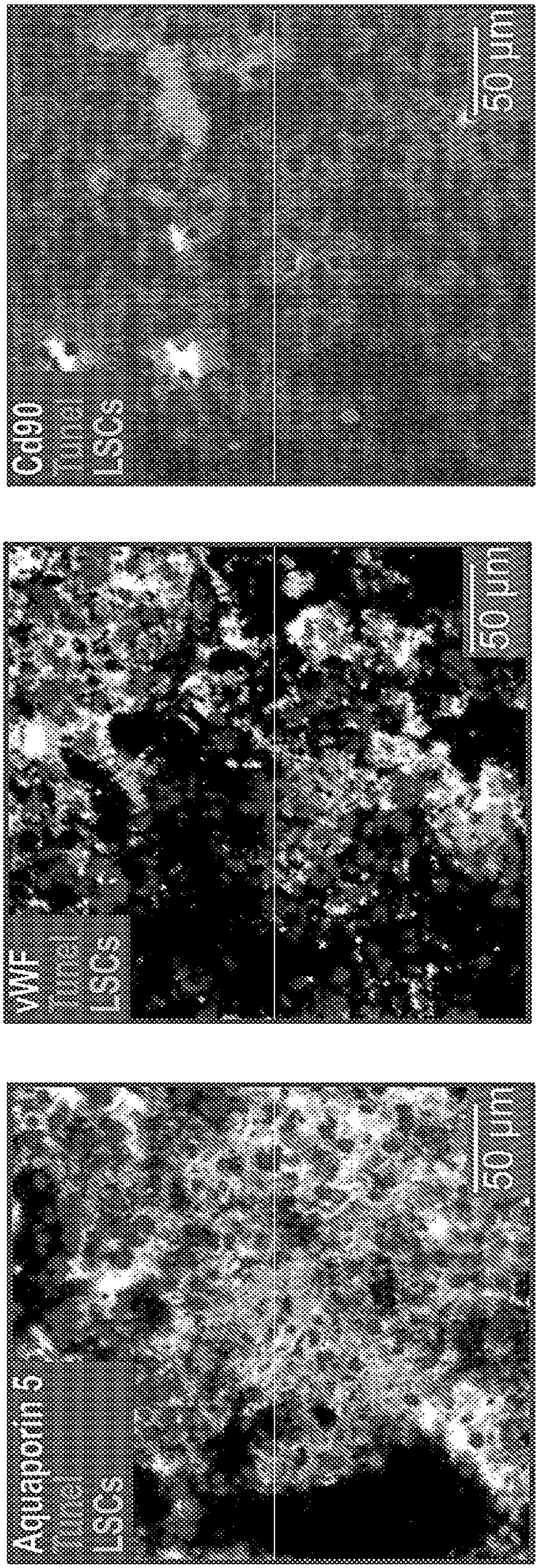

FIG. 11. Co-expression of TUNEL with Aquaporin 5, vWF, or CD90 in mice treated with DiO-labeled LSCs.

Figure 12:
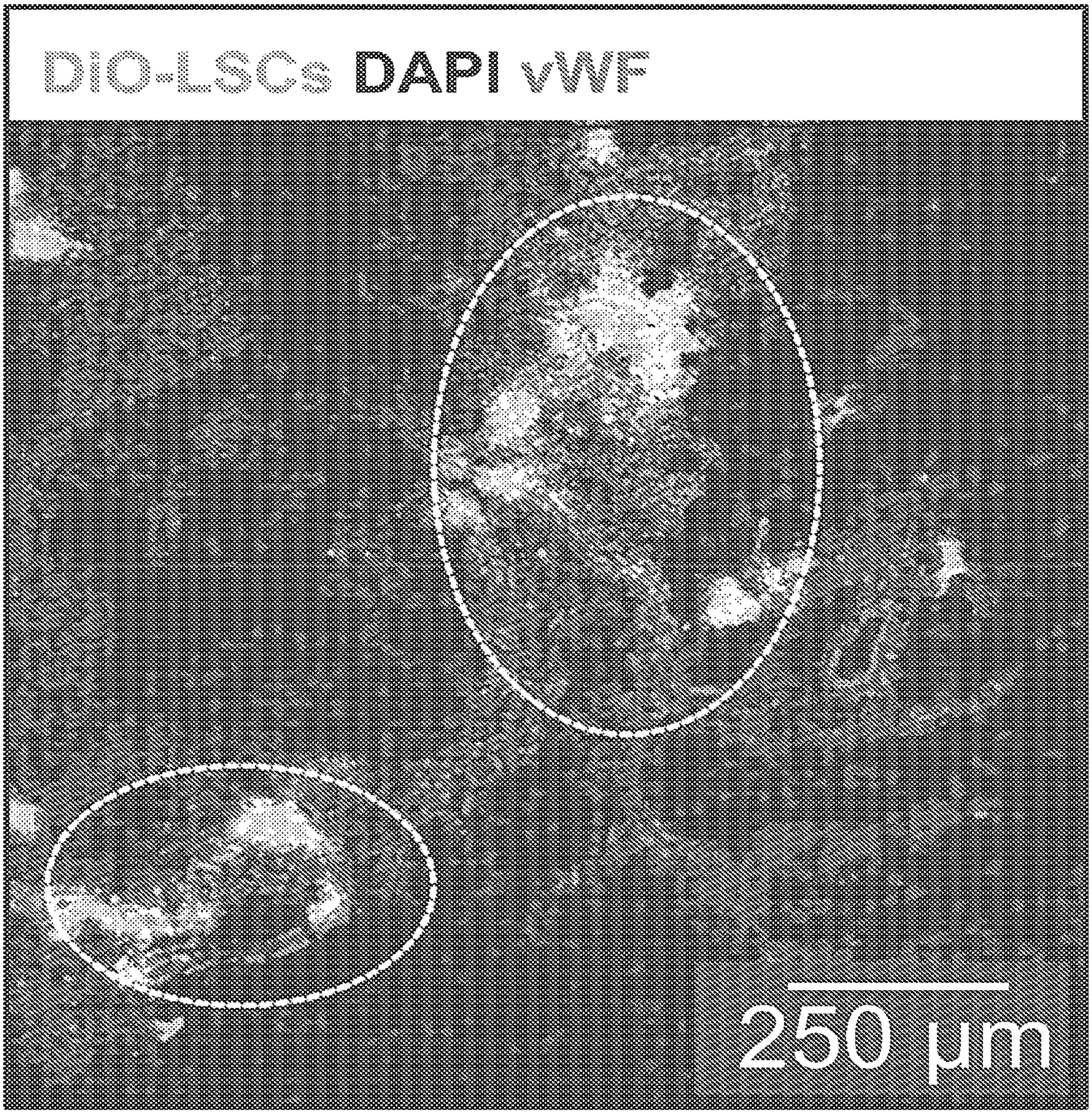

FIG. 12. LSCs promote angiogenesis in mouse lungs with PF.

Figure 13:
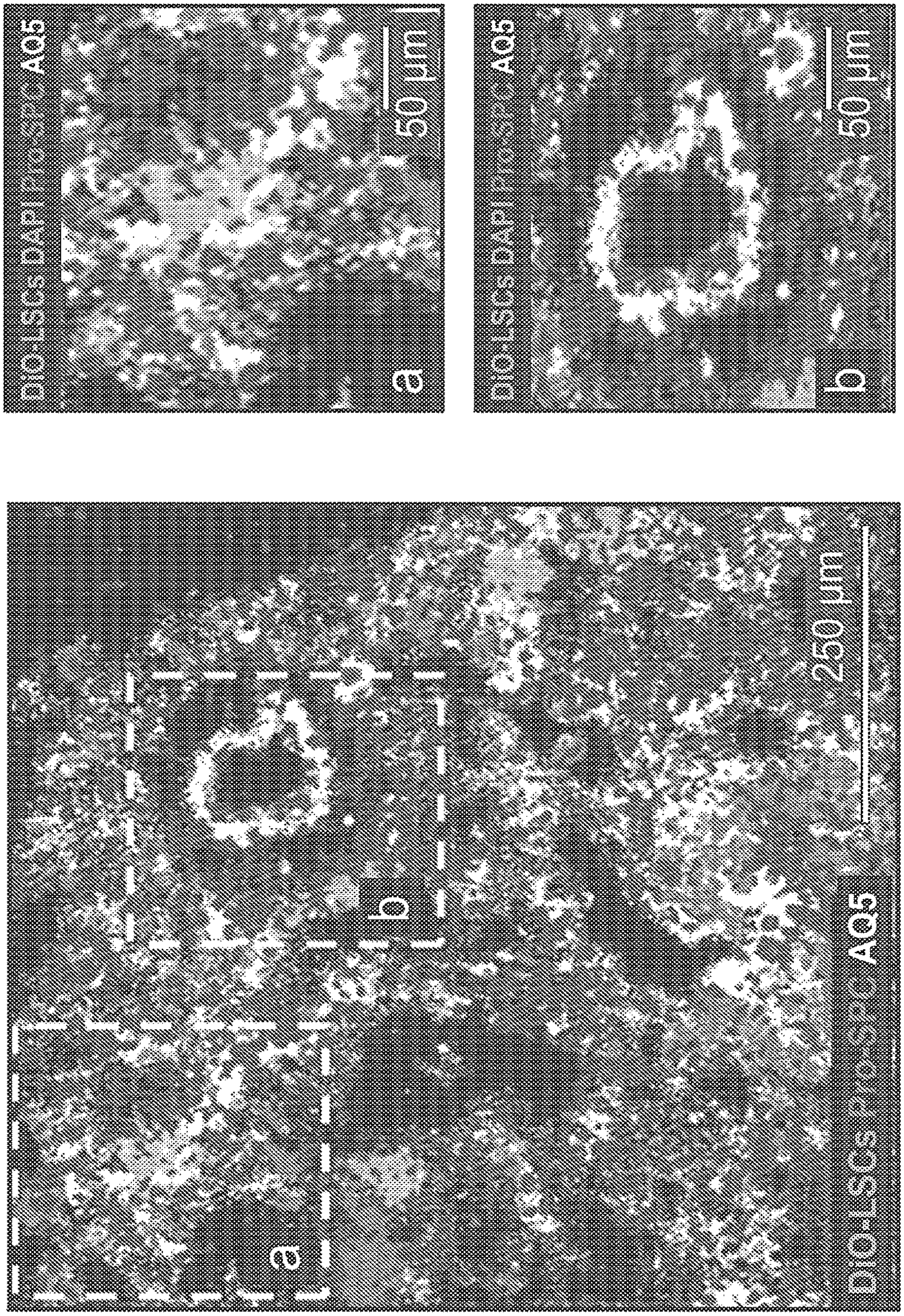

FIG. 13. Expression of Pro-SPC or Aquaporin 5 in LSCs engrafted in the mouse lungs.

Figure 14:
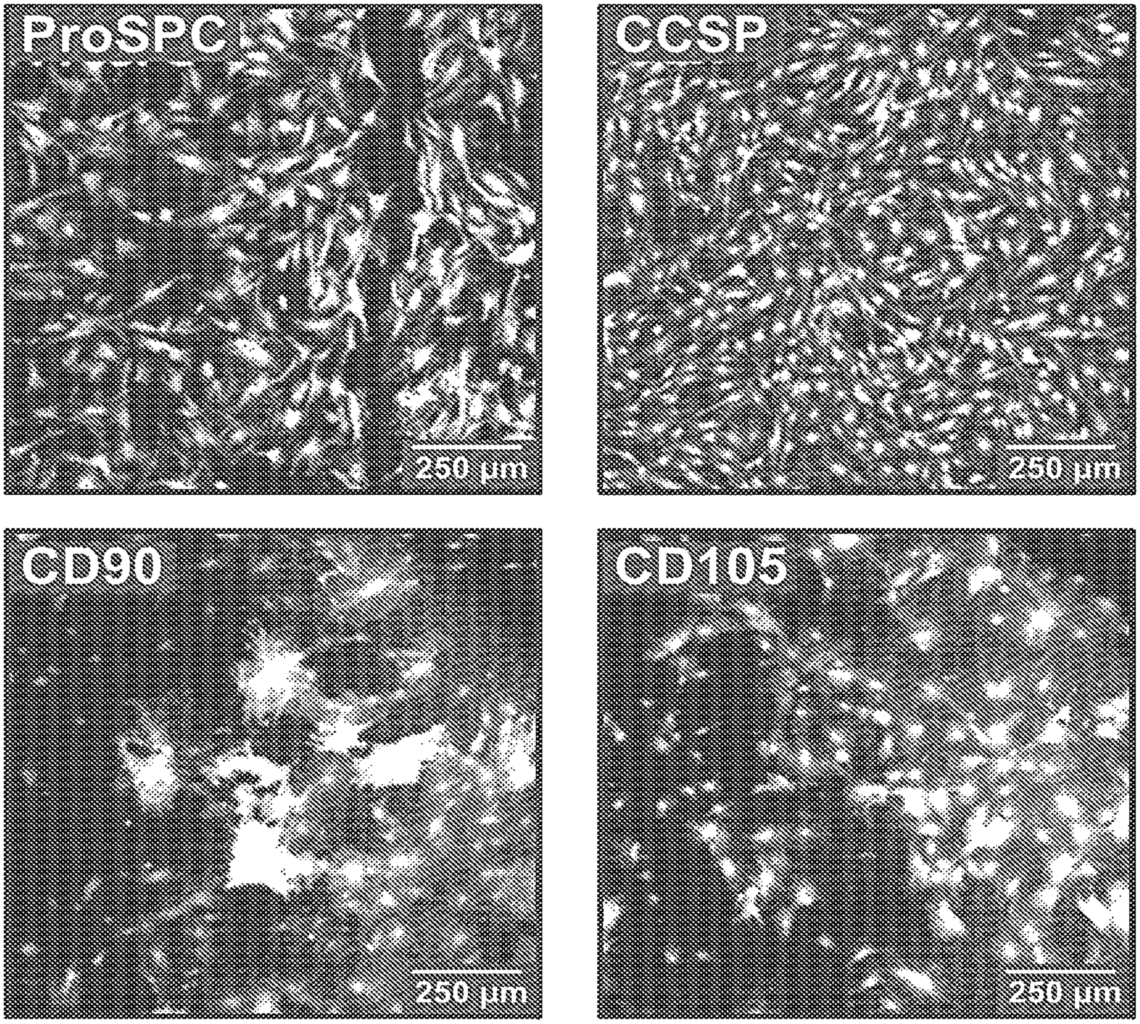

FIG. 14. Expression of Pro-SPC, CCSP, CD90, and CD105 in rat LSCs.

FIG. 15. LSCs cultured in media containing 25 ng/mL EGF and no FBS or in media containing 20% FBS and no EGF.

Figure 16A:
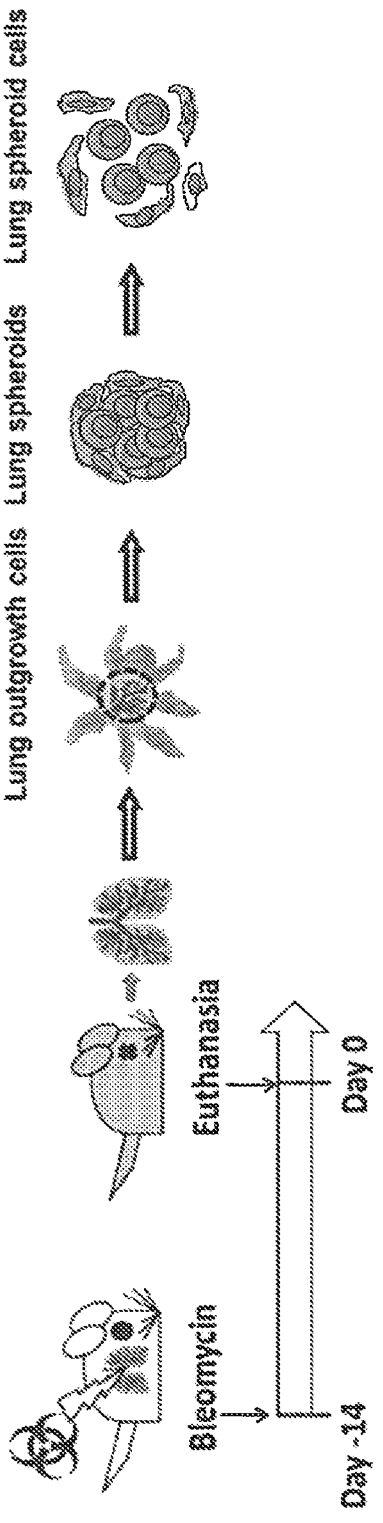
Figure 16B:
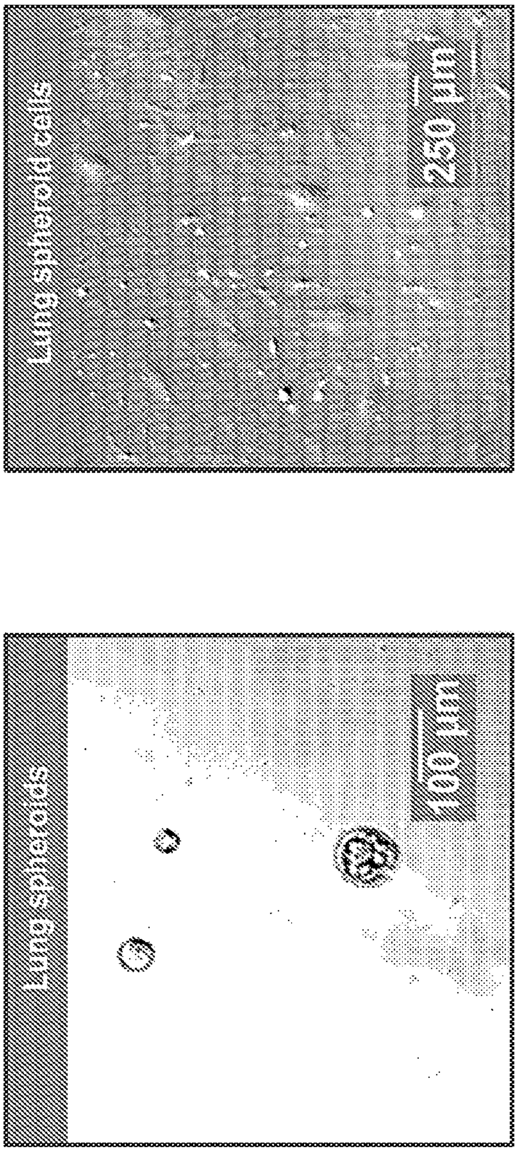

FIGS. 16A-16B. Successful derivation of LSCs from mouse lungs with PF.

Figure 17:
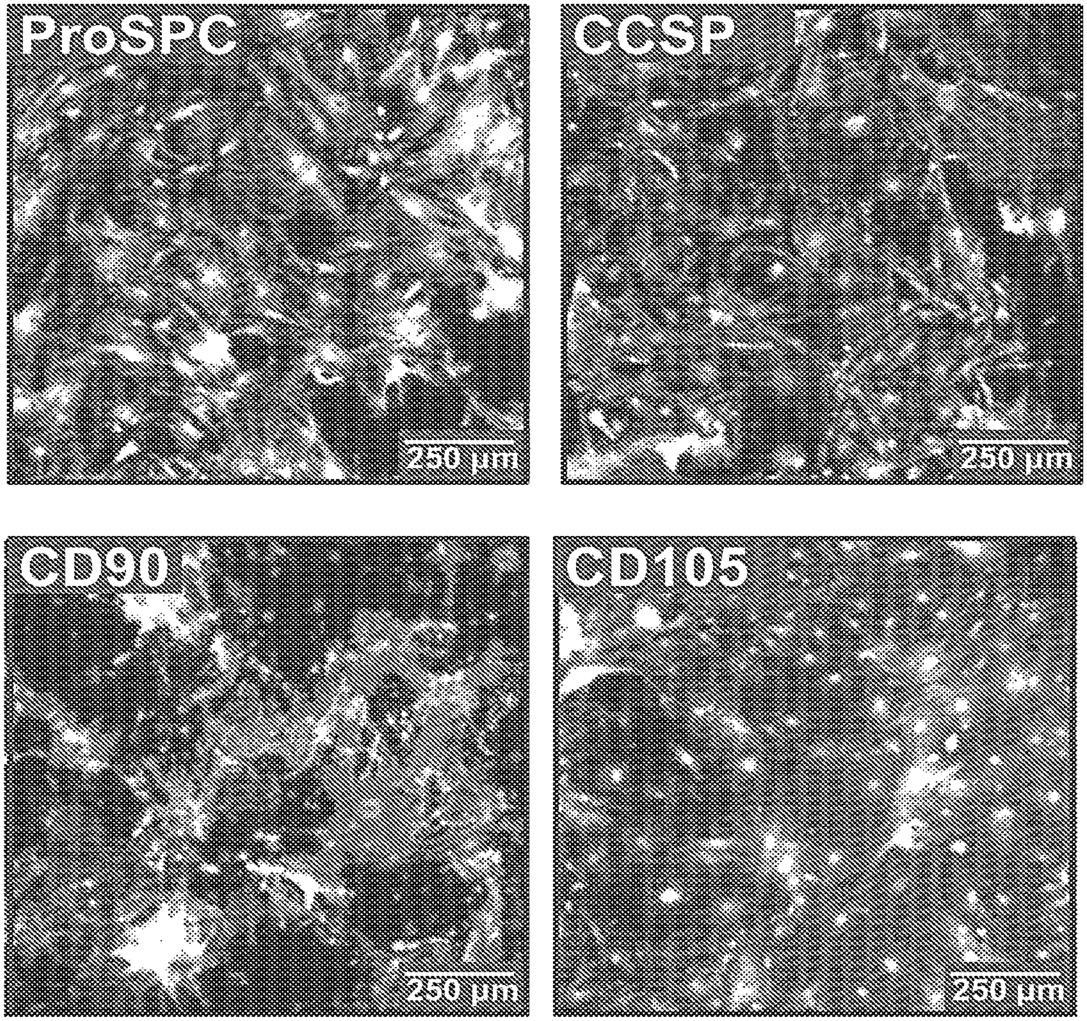

FIG. 17. Expression of Pro-SPC, CCSP, CD90, and CD105 in LSCs from mouse lungs with PF.

Figure 18:
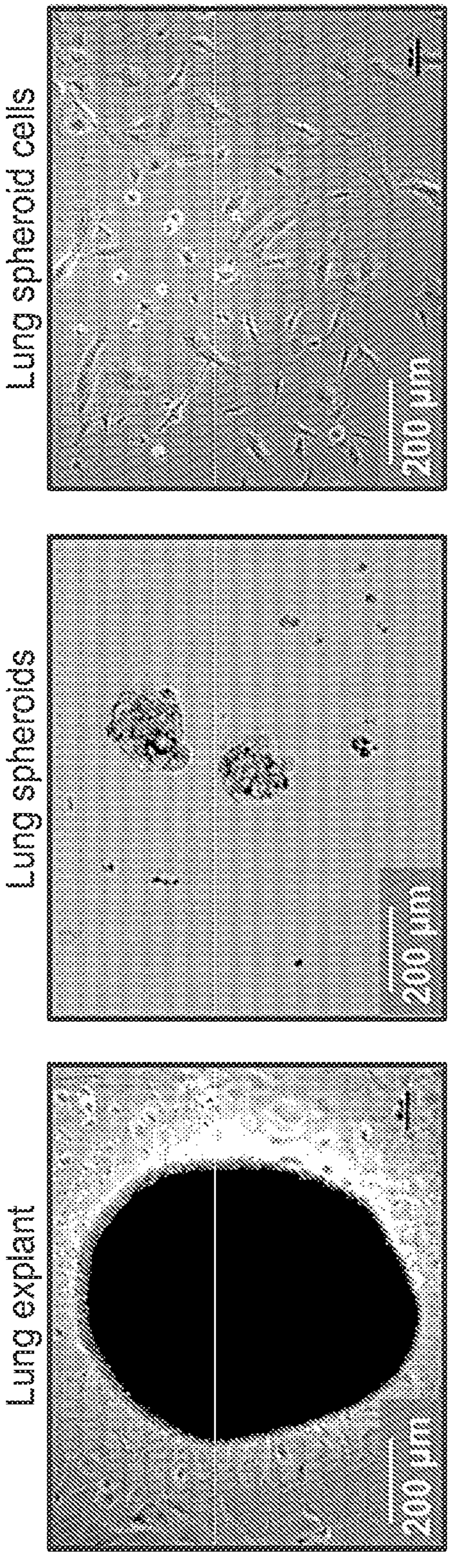

FIG. 18. Successful derivation of LSCs from human IPF lungs.

5. DETAILED DESCRIPTION OF THE INVENTION

5.1. Definitions

As used herein a lung disorder may be acute lung injury (ALI), acute respiratory distress syndrome (ARDS), asthma, autoimmune disease, bacterial pneumonia, bronchiolitis obliterans organizing pneumonia (BOOP), chemical pneumonia, chronic bronchitis, chronic obstructive pulmonary diseases (COPD), cystic fibrosis, emphysema, interstitial lung diseases including sarcoidosis, idiopathic pulmonary fibrosis (IPF), lung cancer, pneumoconiosis, pneumonia, pulmonary edema, pulmonary hypertension, tuberculosis, or viral pneumonia. For a review of BOOP see Barker et al. 2014 NEJM 370 1820-1828.

The lung disorders may be acute lung disorders such as ALI, ARDS, or pneumonia. Alternatively the lung disorder may be a chronic condition such as asthma, COPD, cystic fibrosis, or IPF.

As used herein, a "patient" may be a human or animal (most likely a mammal). Animals that may benefit from the technology disclosed herein may be domestic animals, e.g., pets (cats or dogs); working or show animals (camels, horses, llamas); livestock animals (cows, goats, sheep, swine).

The mammalian lung spheroids may have a (diameter) ranging from about 25 μM to about 500 μM; about 50 μM to about 400 μM; about 75 μM to about 300 μM; about 100 μM to about 200 μM. They may contain about 20 to about $10^5$; or 50 to about $10^4$; or about 100 to about $10^3$; about 150 to about 500 single cells. The number of cells in the mammalian lung spheroids may be controlled by the plating density on the low-adherence surface. The size of the spheroids may depend on the therapeutic indication. Smaller spheroids will be better able to be delivered intravenously for example. Larger spheroids may be directly injected or placed in a particular site.

The lung tissues for preparing the spheroids may be lung biopsies or entire donor lungs. It can be healthy or diseased lungs. The lung tissues can be minced or cut into small pieces before plating.

In one embodiment, the lung spheroids or lung spheroid cells are (i) positive for antibodies to CCSP, CD105, CD90, and Pro-SPC, (ii) slightly positive for EpCAM, CD49f, p75 NGF, c-Kit, and (iii) negative for antibodies to CD31, CD34, CD45, pan cytokeritin.

The culturing conditions may include reagents such as any suitable cell culturing media. It may be IMDM, or other media types too (e.g. DMEM). The medium may also include FBS, or other such as calf serum, sheep serum, human serum or serum replacement chemicals, etc. The media may also include other supplements, growth factors, and chemicals that are beneficial to cell growth and differentiation.

5.2. Cell-Based Therapies

The lung spheroids or lung spheroid cells described herein may be used for a variety of therapeutic uses. Other cell-based therapies provide examples of methods to expand or deliver these lung cells such as the techniques developed for embryonic stem cells (ESCs), pluripotent stem cells (PSCs), or induced pluripotent stem cells (iPSCs). Culturing techniques have been reviewed in Celiz et al. 2014 Nat Mater 13 570-579 and Visnathan et al. 2014 Frontiers in Pharmacology 5 No. 15 pub Jul. 2, 2014. Therapeutic techniques and the clinical needs for iPSCs also have been reviewed. See Isobe et al. 2014 New Biotechnology 31 (5) 411-421. To use the lung spheroids described herein, one may use clinical methods similar to those developed for cardiosphere-derived cells. See the review in Goumans et al. 2014 Heart 100 1153-1157; clinical trials described in Malliaras et al. 2014 J Am Coll Card 63 110-122 and Chugh et al. 2012 Circulation 126 S54-S64. Clinical techniques for mesenchymal stem cells for chronic disorders were recently reviewed. See Farini et al. 2014 Stem Cell Int'l ID no. 306573 published Apr. 30, 2014. For allogeneic transplants of lung spheroids or lung spheroid cells techniques such as HLA matching or other techniques may be used to monitor or reduce the risk of graft versus host disease (GVHD). These methods may be similar to those developed for hematopoetic transplants. See for example, Kanate et al. 2014 World J Stem Cell 6 (2) 69-81.

Cell-based techniques also are described in the patent literature. Examples include, but are not limited to, U.S. Pat. No. 7,682,828 (Jaenisch and Hochedlinger); method of making iPSCs in PCT published applications WO2009/006930, WO2009/006997, WO2009/007852 (Sakurada); US published applications US2009/0246875 (Yamanaka et al.); US2008/0233610 (Thomson et al.); and granted European Pat. No. EP1040185 (Brustle et al.).

5.3. Ex Vivo Gene Therapies

The lung spheroids or lung spheroid cells described herein may be used for a variety of uses including applications such the generation of genetically engineered cells for implantation. Here the lung spheroids/cells may be generated from a patient's own cells (autologous transplantation), cells from a different donor (allogeneic transplantation), or cells from a different species, xenotransplant, such as transgenic or other modifications to reduce or eliminate transplant rejection. For example, suitable porcine lung spheroids or lung spheroid cells may be used for human transplantation. The lung spheroids/cells may be genetically modified using established ex vivo techniques. Examples of ex vivo techniques include, but are not limited to, U.S. Pat. No. 8,741,642 (Manjili et al.); U.S. Pat. No. 8,703,121 (Harris et al.); U.S. Pat. No. 8,420,380 (Fishman et al.); U.S. Pat. No. 8,080,417 (Peled and Hasson); U.S. Pat. No. 7,063,960 (Choi and Wong); U.S. Pat. No. 7,087,431 (Wu et al.); U.S. Pat. No. 6,575,898 (Smith); U.S. Pat. No. 6,251,383 (Upadhyay and Madan); U.S. Pat. No. 5,674,722 (Mulligan et al.); U.S. Pat. No. 5,665,350 (Quesenberry); and U.S. Pat. No. 5,437,994 (Emerson et al.).

5.4. Diagnostics

The lung spheroids or cells described herein may be used for a variety of uses including diagnostic and cell-based assay applications. These lung spheroids or lung spheroid cells may be used for example to culture and test respiratory irritants and microbes for diagnostic purposes. For example, the lung spheroids or cells may be used in a method of diagnosing or detecting bacterial, fungal, or viral pathogens, such as H1N1 influenza, in a sample from a subject comprising: (a) culturing an extract or aliquot of the sample from the subject on the LSCs; (b) detecting the pathogen (H1N1 influenza) in a sample from the subject, by an appropriate assay specific for a biomarker associated with the pathogen (H1N1 influenza); (c) comparing the detected levels to at least one sample from a training set(s), wherein a sample training set(s) comprises data from the levels from a reference sample, and the comparing step comprises applying a statistical algorithm which comprises determining a correlation between the detected levels in the sample from the subject and the detected levels from at least one training set(s); and (d) diagnosing or detecting the pathogen (H1N1 influenza) based on the detected levels in the sample from the subject and the results of the statistical algorithm. One of ordinary skill can select suitable assays for biomarkers associated with the pathogen (H1N1 influenza), PCR assay with primers/probes specific for the pathogen (H1N1 influenza); a nucleic acid hybridization assay, such as a microarray with nucleic acids specific for the pathogen (H1N1 influenza); or antibody assays with antibodies specific for the pathogen (H1N1 influenza).

5.5. Compositions and Kits

The invention provides compositions and kits for preparing lung spheroids or lung spheroid cells prepared by the methods described herein. The compositions may be suitable for therapeutic uses, e.g., an injectable formulation prepared by methods know to those skilled in the art.

Drug Screens

The lung spheroids or lung spheroid cells may also be used for drug screening or the measurement of "functional effects" in the context of assays for testing means compounds that modulate a phenotype or a gene associated with a lung disorder. This may also be a chemical or phenotypic effect such as altered expression profiles of genes in the lung spheroids or lung spheroid cells; altered expression of genes associated with a lung disorder; altered transcriptional activity of a gene associated with a lung disorder; altered translational activity of an mRNA encoding a gene associated with a lung disorder; or altered activities and the downstream effects of proteins encoded by these genes. A functional effect may include transcriptional activation or repression, the ability of cells to proliferate, expression in cells during lung disorder progression, and other cellular characteristics. By "determining the functional effect" is meant assaying for a compound that increases or decreases the transcription of genes or the translation of proteins that are indirectly or directly associated with a lung disorder. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker; measuring changes in enzymatic activity; the ability to increase or decrease cellular proliferation, apoptosis, cell cycle arrest, measuring changes in cell surface markers. Validation of the functional effect of a compound on a lung disorder occurrence or progression can also be performed using assays known to those of skill in the art such as studies using mouse models. The functional effects can be evaluated by many means known to those skilled in the art, e.g., microscopy for quantitative or qualitative measures of alterations in morphological features, measurement of changes in RNA or protein levels for other genes associated with a lung disorder, measurement of RNA stability, identification of downstream or reporter gene expression (CAT, luciferase, β-gal, GFP, and the like), e.g., via chemiluminescence, fluorescence, colorimetric reactions, antibody binding, inducible markers, etc.

"Inhibitors," "activators," and "modulators" of the markers are used to refer to activating, inhibitory, or modulating molecules identified using in vitro and in vivo assays of the expression of genes associated with a lung disorder, mutations associated with a lung disorder, or the translation proteins encoded thereby. Inhibitors, activators, or modulators also include naturally occurring and synthetic ligands, antagonists, agonists, antibodies, peptides, cyclic peptides, nucleic acids, antisense molecules, ribozymes, shRNAs, RNAi molecules, small organic molecules and the like. Such assays for inhibitors and activators include, e.g., (1) (a) the mRNA expression, or (b) proteins expressed by genes associated with a lung disorder; (2) applying putative modulator compounds; and (3) determining the functional effects on activity, as described above.

Statistical Methods

The data may be ranked for its ability to distinguish biomarkers in both the 1 versus all (i.e., disease versus normal) and the all-pairwise (i.e., normal versus specific disease) cases. One statistic used for the ranking is the area under the receiver operator characteristic (ROC) curve (a plot of sensitivity versus (1-specificity)). Although biomarkers are evaluated for reliability across datasets, the independent sample sets are not combined for the purposes of the ROC ranking. As a result, multiple independent analyses are performed and multiple independent rankings are obtained for each biomarker's ability to distinguish groups of interest.

It is to be understood that other genes and/or diagnostic criteria may be used in this invention. For example, patient characteristics, standard blood workups, the results of imaging tests, and/or histological evaluation may optionally be combined with biomarkers disclosed herein.

Such analysis methods may be used to form a predictive model, and then use that model to classify test data. For example, one convenient and particularly effective method of classification employs multivariate statistical analysis modeling, first to form a model (a "predictive mathematical model") using data ("modeling data") from samples of known class (e.g., from subjects known to have, or not have, a particular class, subclass or grade of lung cancer), and second to classify an unknown sample (e.g., "test data"), according to lung cancer status.

Pattern recognition (PR) methods have been used widely to characterize many different types of problems ranging for example over linguistics, fingerprinting, chemistry and psychology. In the context of the methods described herein, pattern recognition is the use of multivariate statistics, both parametric and non-parametric, to analyze spectroscopic data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. The other approach is termed "supervised" whereby a training set of samples with known class or outcome is used to produce a mathematical model and is then evaluated with independent validation data sets.

Unsupervised PR methods are used to analyze data without reference to any other independent knowledge. Examples of unsupervised pattern recognition methods include principal component analysis (PCA), hierarchical cluster analysis (HCA), and non-linear mapping (NLM).

Alternatively, and in order to develop automatic classification methods, it has proved efficient to use a "supervised" approach to data analysis. Here, a "training set" of biomarker expression data is used to construct a statistical model that predicts correctly the "class" of each sample. This training set is then tested with independent data (referred to as a test or validation set) to determine the robustness of the computer-based model. These models are sometimes termed "expert systems," but may be based on a range of different mathematical procedures. Supervised methods can use a data set with reduced dimensionality (for example, the first few principal components), but typically use unreduced data, with all dimensionality. In all cases the methods allow the quantitative description of the multivariate boundaries that characterize and separate each class, for example, each class of lung cancer in terms of its biomarker expression profile. It is also possible to obtain confidence limits on any predictions, for example, a level of probability to be placed on the goodness of fit (see, for example, Sharaf; Illman; Kowalski, eds. (1986). Chemometrics. New York: Wiley). The robustness of the predictive models can also be checked using cross-validation, by leaving out selected samples from the analysis.

Examples of supervised pattern recognition methods include the following nearest centroid methods (Dabney 2005 *Bioinformatics* 21 (22): 4148-4154 and Tibshirani et al. 2002 *Proc. Natl. Acad. Sci. USA* 99 (10): 6576-6572); soft independent modeling of class analysis (SIMCA) (see, for example, Wold, (1977) Chemometrics: theory and application 52:243-282.); partial least squares analysis (PLS) (see, for example, Wold (1966) Multivariate analysis 1:391-420; Joreskog (1982) Causality, structure, prediction 1:263-270); linear discriminant analysis (LDA) (see, for example, Nillson (1965). Learning machines. New York.); K-nearest neighbor analysis (KNN) (see, for example, Brown and Martin 1996 *J Chem Info Computer Sci* 36 (3): 572-584); artificial neural networks (ANN) (see, for example, Wasserman (1993). Advanced methods in neural computing. John Wiley & Sons, Inc; O'Hare & Jennings (Eds.). (1996). Foundations of distributed artificial intelligence (Vol. 9). Wiley); probabilistic neural networks (PNNs) (see, for example, Bishop & Nasrabadi (2006). Pattern recognition and machine learning (Vol. 1, p. 740). New York: Springer; Specht, (1990). Probabilistic neural networks. Neural networks, 3 (1), 109-118); rule induction (RI) (see, for example, Quinlan (1986) Machine learning, 1 (1), 81-106); and, Bayesian methods (see, for example, Bretthorst (1990). An introduction to parameter estimation using Bayesian probability theory. In Maximum entropy and Bayesian methods (pp. 53-79). Springer Netherlands; Bretthorst, G. L. (1988). Bayesian spectrum analysis and parameter estimation (Vol. 48). New York: Springer-Verlag); unsupervised hierarchical clustering (see for example Herrero 2001 *Bioinformatics* 17 (2) 126-136). In one embodiment, the classifier is the centroid based method described in Mullins et al. 2007 *Clin Chem* 53 (7): 1273-9, which is herein incorporated by reference in its entirety for its teachings regarding disease classification.

It is often useful to pre-process data, for example, by addressing missing data, translation, scaling, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

If possible, missing data, for example gaps in column values, should be avoided. However, if necessary, such missing data may replaced or "filled" with, for example, the mean value of a column ("mean fill"); a random value ("random fill"); or a value based on a principal component analysis ("principal component fill"). Each of these different approaches will have a different effect on subsequent PR analysis.

"Translation" of the descriptor coordinate axes can be useful. Examples of such translation include normalization and mean centering. "Normalization" may be used to remove sample-to-sample variation. Many normalization approaches are possible, and they can often be applied at any of several points in the analysis. "Mean centering" may be used to simplify interpretation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt (StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centred and unit variance scaled. This technique is a very useful because each descriptor is then weighted equally and large and small values are treated with equal emphasis. This can be important for analytes present at very low, but still detectable, levels.

Several supervised methods of scaling data are also known. Some of these can provide a measure of the ability of a parameter (e.g., a descriptor) to discriminate between classes, and can be used to improve classification by stretching a separation. For example, in "variance weighting," the variance weight of a single parameter (e.g., a descriptor) is calculated as the ratio of the inter-class variances to the sum of the intra-class variances. A large value means that this variable is discriminating between the classes. For example, if the samples are known to fall into two classes (e.g., a training set), it is possible to examine the mean and variance of each descriptor. If a descriptor has very different mean values and a small variance, then it will be good at separating the classes. "Feature weighting" is a more general description of variance weighting, where not only the mean and standard deviation of each descriptor is calculated, but other well-known weighting factors, such as the Fisher weight, are used.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

The process of comparing a measured value and a reference value can be carried out in any convenient manner appropriate to the type of measured value and reference value for the discriminative gene at issue. "Measuring" can be performed using quantitative or qualitative measurement techniques, and the mode of comparing a measured value and a reference value can vary depending on the measurement technology employed. For example, when a qualitative colorimetric assay is used to measure expression levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values. In other examples, measured values are qualitative. As with qualitative measurements, the comparison can be made by inspecting the numerical data, or by inspecting representations of the data (e.g., inspecting graphical representations such as bar or line graphs).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a biomarker protein. Alternately, a separate device (e.g., a digital computer) may be used to compare the measured value(s) and the reference value(s). Automated devices for comparison may include stored reference values for the biomarker protein(s) being measured, or they may compare the measured value(s) with reference values that are derived from contemporaneously measured reference samples (e.g., samples from control subjects).

As will be apparent to those of skill in the art, when replicate measurements are taken, the measured value that is compared with the reference value is a value that takes into account the replicate measurements. The replicate measurements may be taken into account by using either the mean or median of the measured values as the "measured value."

The invention also includes methods of identifying patients for particular treatments or selecting patients for which a particular treatment would be desirable or contraindicated.

The methods above may be performed by a reference laboratory, a hospital pathology laboratory or a doctor. The methods above may further comprise an algorithm and/or statistical analysis.

Pharmaceutically Acceptable Compositions

Any of the above-described lung spheroids or lung spheroid cells can be administered in the form of a composition, that is, with one or more additional components such as a physiologically acceptable carrier, excipient, or diluent. For example, a composition may comprise a lung spheroids or lung spheroid cells as described herein plus a buffer, an antioxidant such as ascorbic acid, a low molecular weight polypeptide (such as those having less than 10 amino acids), a protein, amino acids, carbohydrates such as glucose, sucrose, or dextrin, chelating agent such as EDTA, glutathione, and/or other stabilizers, excipients, and/or preservatives. The composition may be formulated as a liquid or a lyophilizate. Further examples of components that may be employed in pharmaceutical formulations are presented in

*Remington's Pharmaceutical Sciences,* $16^{th}$ Ed., Mack Publishing Company, Easton, Pa., (1980), the relevant portions of which are incorporated herein by reference.

Compositions comprising lung spheroids or lung spheroid cells described above can be administered by any appropriate means including, but not limited to, parenteral, topical, oral, nasal, vaginal, rectal, or pulmonary (by inhalation) administration. If injected, the composition(s) can be administered intra-articularly, intravenously, intraarterially, intramuscularly, intraperitoneally or subcutaneously by bolus injection or continuous infusion. Localized administration, that is, at the site of disease, is contemplated, as are transdermal delivery and sustained release from implants, skin patches, or suppositories. Delivery by inhalation includes, for example, nasal or oral inhalation, use of a nebulizer, inhalation in aerosol form, and the like. Administration via a suppository inserted into a body cavity can be accomplished, for example, by inserting a solid form of the composition in a chosen body cavity and allowing it to dissolve. Other alternatives include eye drops, oral preparations such as pills, lozenges, syrups, and chewing gum, and topical preparations such as lotions, gels, sprays, and ointments. In most cases, lung spheroids or lung spheroid cells can be administered topically or by injection or inhalation.

The lung spheroids or lung spheroid cells described above can be administered at any dosage, frequency, and duration that can be effective to treat the condition being treated. The dosage depends on the molecular nature of the therapeutic molecule and the nature of the disorder being treated. Treatment may be continued as long as necessary to achieve the desired results. The periodicity of treatment may or may not be constant throughout the duration of the treatment. For example, treatment may initially occur at weekly intervals and later occur every other week. Treatments having durations of days, weeks, months, or years are encompassed by the invention. Treatment may be discontinued and then restarted.

Maintenance doses may be administered after an initial treatment. Dosage may be measured as numbers of cells per kilogram of body weight (n/kg) or as numbers of cells per square meter of skin surface ($n/m^2$) or as a fixed dose, irrespective of height or weight. These are standard dosage units in the art. A person's skin surface area is calculated from her height and weight using a standard formula. For example, therapeutic lung spheroids or lung spheroid cells can be administered at a dose of from about $1.0\times10^4$ cells/kg to about $1.0\times10^{10}$ cells/kg or from about $1.0\times10^5$ cells/kg to about $1.0\times10^8$ cells/kg. Alternatively, a dose of from about $1.0\times10^6$ cells to about $1.0\times10^{11}$ cells can be administered. Or a dose of about $2.0\times10^6$ cells, $5.0\times10^6$ cells, $1.0\times10^7$ cells, $2.0\times10^7$ cells, $5.0\times10^7$ cells, $1.0\times10^8$ cells, $5.0\times10^8$ cells, $1.0\times10^9$ cells, $5.0\times10^9$ cells, $1.0\times10^{10}$ cells, or $5.0\times10^{10}$ cells may be administered.

Unless defined otherwise, all technical and scientific terms used herein have the same meaning as commonly understood by one of ordinary skill in the art to which this invention belongs. The article "a" and "an" are used herein to refer to one or more than one (i.e., to at least one) of the grammatical object(s) of the article. By way of example, "an element" means one or more elements.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The following Examples further illustrate the invention and are not intended to limit the scope of the invention. In particular, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

6. EXAMPLES

We sought to develop a streamlined method to generate clinically-applicable amounts of resident lung progenitors. Multicellular spheroid represents a three-dimensional cell culture method frequently used in cancer biology [17, 18]. The spheroid method has also been used to generate neural stem cells [19] and cardiac stem cells [20]. It has also been reported that the spheroid environment mimics the in vivo stem cell niche and is able to reprogram somatic cells into neural progenitor-like cells [21, 22]. We hypothesize that lung spheroids can be generated from healthy lung tissues and they may contain lung progenitor cells suitable for therapeutic applications. Outgrowth cells from adult human lung tissues self-aggregated into three-dimensional multicellular lung spheroids. These spheroids resemble the stem niche. When re-plated onto fibronectin-coated surfaces, lung spheroids dissociated into single cells which we termed lung spheroid cells (LSCs). Lung spheroids and LSCs represent selective mixtures of both lung progenitors and supporting stromal cells. Intravenous infusion of human LSCs ameliorated bleomycin-induced pulmonary fibrosis in immunodeficiency mice. In a rat model of pulmonary fibrosis, a head-to-head comparison revealed the therapeutic superiority of LSCs over adipose-derived mesenchymal stem cells with the same genetic background.

Methods

Generation of Lung Spheroids and Lung Spheroid Cells

Rat Lung Spheroids and Lung Spheroid Cells

We derived lung spheroids and lung spheroid cells from rat lungs, see the procedure below. Lungs from Wistar-Kyoto rats were explanted and minced into small fragments. Cells outgrowing from the lung explants were collected and forced to form lung spheroids in suspension culture. The lung spheroids were re-plated onto adherence culture to generate lung spheroid cells. The morphologies of rat lung spheroids and lung spheroid cells resemble their human counterparts.

Healthy human lung tissues were acquired from the Cystic Fibrosis and Pulmonary Diseases Research and Treatment Center at the University of North Carolina-Chapel Hill. Donor comorbidity is shown in Table 1.

TABLE 1

| | Sex | age | race | cause of death | smoking |
|---|---|---|---|---|---|
| Lung Donor 1 | Female | 50 | Hispanic | Anoxia 2nd Cardiovascular | No |
| Lung Donor 2 | Female | 52 | Black | Cerebrovascular Accident | No |
| Lung Donor 3 | Male | 18 | Hispanic | Head Trauma 2nd Self-Inflicted Gunshot Wound | No |

An approximately 6 mm×6 mm piece distal lung tissue was separated and washed with phosphate buffered saline (PBS) (Life Technologies). The tissue sample was then cut into smaller biopsy-sized pieces, and washed three times with PBS, followed by enzymatic digestion at 37° C. in collagenase IV solution (5 mg/ml) (Sigma-Aldrich) for 5 minutes. Iscove's Modified Dulbecco's Media (IMDM; Life Technologies) containing 20% fetal bovine serum (FBS; Corning) is then added to the sample to inactivate the collagenase. After that the tissue samples were further minced into smaller tissue explants (~0.5×0.5 mm) before plating. Approximately 50 pieces of tissue explants were then placed onto a fibronectin-coated plate with approximately 1.5 cm between each explant and covered with 2 mL of IMDM with 20% FBS overnight to aid their attachment onto the plate. The cultures were maintained in IMDM with 20% FBS and media change was performed every other day. In about one week, cells started to outgrow from the tissue explants. Once these outgrowth cells were about 70-80% confluent, they were harvested by 5-10 minute of incubation with TryPLE Select™ (Life Technologies). The cells were then seeded into an Ultra-Low attachment flask (Corning) at a density of 100,000 cells/cm$^2$ and cultured in IMDM with 10% FBS for spheroid formation. Phase-bright lung spheroids (LSs) started to form in 3-7 days. LSs were then collected from the suspension culture flasks and re-plated onto fibronectin-coated surface to produce adherent lung spheroid cells (LSCs). LSCs were cultured in IMDM with 20% FBS media, 50 μg/mL gentamicin, 2 mmol/L L-Glutamine (Life Technologies), and 0.1 mmol/L 2-mercaptoethanol (Life Technologies). A cohort of LSCs were cultured in FBS-free media and containing 25 ng/ml epidermal growth factor (EGF; from Shenandoah Biotechnology, PA) to test the effects of EGF on cell growth. The cells were passaged every 3-5 days. We used Passage 2-3 LSCs for all in vitro and in vivo testing. Human pulmonary alveolar epithelial cells (HPAEpiC; from ScienCell Research Laboratories) and normal human dermal fibroblast cells (NHDF; from ATCC) were cultured in the same media as control cells to human LSCs. Rat LSCs were generated from 6-week-old syngeneic Wistar-Kyoto rats using a similar protocol as human LSCs. Rat adipose-derived mesenchymal stem cells (AD-MSCs) were derived from the same strain of rats as previously described. Li et al. 2012 J Amer Coll Cardiol 59 942-953. Mouse PF-LSCs were generated from 6-week-old CD1 mice (Charles River Labs) 14 days after bleomycin instillation. Lung biopsy tissues from IPF patients were obtained from the IPF Clinic of University of North Carolina—Chapel Hill.

Flow Cytometry Analysis

To characterize the antigenic phenotypes of LSCs, flow cytometry was performed using a FACSCalibur or an LSR II flow cytometer (BD) and analyzed using FLOWJO™ software (TreeStar). Cells were incubated with antibodies against CD31, CD34, CD45, CD49f, CD90, CD105, c-Kit, EpCAM, p75 NGF, CCSP, Pro-SPC, pan cytokeratin and aquaporin 5 for 60 min. Isotype-identical antibodies served as negative control. Human bone marrow-derived mesenchymal stem cells (BM-MSCs) were obtained from Lonza as control cells for flow cytometry and the BM-MSCs were cultured in the same LSC media. To reveal the change of cell phenotype from spheroids to adherent cells, lung spheroids were dissociated into single cells by 10-15 min incubation with TryPEL Select™ (Life Technologies, CA) and the dissociated cells were subjected to flow cytometry analysis.

Immunocytochemistry on Lung Spheroids and LSCs

LSCs were plated onto fibronectin-coated chamber slides (BD Biosciences) and subsequently fixed with 4% paraformaldehyde (PFA) before immunocytochemistry (ICC) for aforementioned antigens. Lung spheroids were mounted in OCT (TISSUE-TEK®) and cryo-sectioned (5 μm) for immunostaining. Images were taken with a epi-fluorescent microscope (Olympus IX81). LSCs or lung spheroid sections were stained with the antibodies against CD31, CD34, CD45, CD49f, CD90, CD105, c-Kit, EpCAM, p75 NGF, CCSP, Pro-SPC, pan cytokeratin, KRT5, p63 and aquaporin 5 and detected by FITC- or Texas Red-conjugated secondary antibodies.

In Vitro Alveoli-Like Structure Formation, Differentiation and Paracrine Assays

LSCs were plated onto Matrigel™ (BD Biosciences) for observation of the formation of alveoli-like structures in vitro. LSCs were transduced with viral particles of enhanced green fluorescent protein (EGFP, Vector Biolabs). Furthermore, LSCs on Matrigel™ were fixed with 4% PFA, followed by immunostaining on EGFP and aquaporin 5. Nuclei were counter-stained with DAPI. To reveal the effects of LSC-secreted factors on lung epithelial cell survival, (HPAEpiC) were cultured in control media (plain IMDM) or LSC-conditioned media (LSC-CM). After 3 days, live and dead HPAEpiCs were stained with Calcein-AM and ethidium homodimer-1 (EthD) respectively (Live/Dead Assay Kit, Life Technologies). The pro-angiogenic effects of LSC-conditioned media were studied by endothelial cell tube formation assay. Human umbilical vein endothelial cells (HUVECs; from ATCC) were seeded onto growth factor-reduced Matrigel™ in 96-well plates at a density of 2×10$^4$ cells per well. 100 μL of plain IMDM or conditioned media from human LSCs were added into the wells. After 4 hours, the wells were imaged with a Nikon TE-200 white light microscope. The average tube length was then measured with NIH Image J Software. The cytokines and growth factors secreted by LSCs were determined by a protein dot array (RayBiotech Inc). Conditioned media from normal human dermal fibroblasts (NHDFs) was used as the control for protein array.

Animal Procedures

All animal work is compliant with the Institutional Animal Care and Use Committee at North Carolina State University. 6 to 8-week old female severe combined immunodeficiency (SCID) mice (Charles River Laboratories) were randomized into the following three treatment groups (n=6-7 mice for each group): 1) Sham control: mice receiving 50 μl PBS instilled intratracheally into the lungs; 2) Bleo+saline: mice receiving 0.7 U/kg body weight bleomycin in 50 μl PBS (EMD Biosciences) instilled intratracheally into the lungs, followed by tail vein injection of 200 μl PBS 24 hrs later. 3) Bleo+LSC: mice receiving 0.7 U/kg body weight bleomycin in 50 μl PBS instilled intratracheally into the lungs, followed by tail vein injection of $1\times10^6$ human LSCs in 200 μl PBS 24 hrs later. A subset of animals in the Bleo+LSC group received LSCs labeled with green fluorescent cell tracker DiO (Life Technologies) or transduced with viral particles of EGFP (Vector Biolabs), which facilitates histological detection of infused cells in the mouse lungs. At Day 14, all mice were sacrificed and their lungs were harvested for histological analysis, including hematoxylin and eosin (H & E) staining for alveolar thickening and infiltration, Masson's Trichrome staining for fibrosis, terminal deoxynucleotidyl transferase dUTP nick end labeling (TUNEL) staining for cell apoptosis and other immunohistochemistry (IHC) staining for angiogenesis and differentiation of LSCs. To perform a head-to-head comparison of LSCs and another stem cell type in lung regeneration, $5\times10^6$ syngeneic rat LSCs or AD-MSCs were injected into 6-week-old female Wistar-Kyoto rats (Charles River Laboratories) with bleomycin-induced pulmonary fibrosis. Animals were euthanized 14 days later. The same H&E staining was performed to measure the degree of lung injury.

Histology

All animals were sacrificed 14 days after treatment. Mouse lungs were harvested and frozen in OCT compound. Cryosections (5 μm thick) were prepared. For H&E staining, lung cryosections were stained for 2 minutes in Hematoxylin and 30 seconds in Eosin, Masson's trichrome staining was performed as per manufacturer's instructions (HT15 Trichrome Staining (Masson) Kit; Sigma-Aldrich). For immunofluorescence staining, lung cryosections were fixed with 4% PFA, blocked/permeabilized with Protein Block Solution (DAKO, Carpinteria, CA) containing 1% saponin (Sigma-Aldrich), and then stained with the following antibodies: rabbit anti-von Willebrand factor (Abcam), rabbit anti-Aquaporin 5 (Abcam), and chicken anti-GFP (Abcam). FITC or Texas-Red secondary antibodies were obtained from Abcam as well. Images were taken by a Zeiss LSM 710 laser scanning confocal microscopy system. Apoptotic cells were detected by terminal deoxynucleotidyl transferase dUTP nick end labeling (TUNEL) assay using the In Situ Cell Death Detection Kit (Roche Diagnostics, Mannheim, Germany), according to the manufacturer's instructions.

PCR Array

Using the $RT^2$ Profiler™ PCR Array System (Qiagen), we compared the expressions of stem cell-related genes in human LSCs and HPAEpiCs. Briefly, total RNA was extracted from explanted lungs and cDNA was prepared from the total RNA mixture of three independent lungs using the $RT^2$ First Strand Kit (Qiagen). Experimental cocktail was prepared by adding cDNA to $RT^2$ qPCR Master Mix (Qiagen) within the 96-well PCR array. Quantitative real time PCR was performed with a Roche Light Cycler Real Time PCR System. A similar fibrosis-related gene PCR array was employed to compare the expressions of key genes involved in dysregulated tissue remodeling during the repair and fibrosis in "Bleo+saline" and "Bleo+LSC" lungs.

Statistical Analysis

Results are presented as mean±SD unless specified otherwise. Comparisons between any 2 groups were performed using 2-tailed unpaired Student's t test. Comparisons among more than 2 groups were performed using one way ANOVA followed by post-hoc Bonferroni correction. Differences were considered statistically significant when $p<0.05$.

Results

Generation of Lung Spheroids and LSCs

Using a three-stage "adhesion-suspension-adhesion" culture process (FIG. 1A), we derived lung spheroids and LSCs from healthy adult human lung tissues. Both phase-bright and stromal-like cells started to outgrow from the lung tissue explants in a week after plating onto fibronectin-coated surfaces. Those outgrowth cells become confluent in ~2-3 weeks (FIG. 1C panel I). When seeded on Ultra-Low Attachment Surface (to discourage cell attachment), the outgrowth cells spontaneously aggregate into three-dimensional lung spheroids (FIG. 1B-ii). When re-plated onto a fibronectin-coated surface, lung spheroids dissociated into single cells we termed lung spheroid cells (LSC; FIG. 1C panel II). One biopsy-sized lung tissue can generate up to 50-200 million, more typically 10-20 million Passage 0 LSCs. When maintained and passaged in IMDM with 20% FBS (FIG. 1C panel IV), LSCs can further undergo 5-15 doublings in 15-50 days (FIG. 1B). Such cell yield and growth potential should suffice the requirement for clinical cell manufacturing.

Cell Phenotypes in Lung Spheroids and LSCs

Immunocytochemistry revealed an organized structure of each lung spheroid (FIG. 1D). Clusters of lung stem cells/progenitor cells (e.g. Pro-SPC-, p63-positive cells, KRT5-positive cells and/or CCSP-positive cells) reside in the spheroid core surrounded by CD105- or CD90-positive supporting (stromal-like) cells. These architectural features of lung spheroids resemble previously reported stem cell niches found in cardiac stem cell formed spheroids [23]. Lung spheroids did not contain cells expressing hematopoetic markers such as CD45, CD31, and CD34, nor did they contain cells expressing mature lung epithelial marker pan cytokeratin or aquaporin. Lung spheroids also contain a small fraction of cells expressing p75 NGF, EpCAM, and CD49f, but not c-kit. As derivatives of lung spheroids, LSCs displayed a similar phenotypic profile. Flow cytometry analysis (FIGS. 2A & 2B) revealed that LSCs were highly positive for CD105, CD90, Pro-SPC, CCSP and weekly positive for p75 NGF, EpCAM, and CD49f. Double staining confirmed that a subpopulation of LSCs is positive for both Pro-SPC and CCSP (FIG. 2C). LSCs are negative for hematopoietic cell markers CD45, CD31, and CD34 or mature lung epithelial cell marker pan cytokeratin or aquaporin. These compound data suggest LSC represent a selective mixture of lung progenitor cells and supporting cells. The phenotype of LSCs were distinct from BM-MSCs as the latter did not express Pro-SPC or CCSP (FIG. 7A(1)-7B(4)). To reveal the changes of cell phenotype from spheroids to adherent cells, we dissociated lung spheroids into single cells and then performed flow cytometry analysis. The results indicated a similar phenotype, except for slightly higher Pro-SPC expression at the spheroid stage (FIG. 8B-8C). Immunocytochemistry on LSCs confirmed the flow cytometry results (FIG. 2B). To enable histological detection, a cohort of LSCs were transduced with EGFP viral particles. We confirmed that EGFP transduction did not affect the phenotype of LSCs (FIG. 9). Using a stemness-related gene PCR array, we compared the gene expressions of human LSCs and (HP AEpiC) (data not shown). Multiple genes were upregulated in LSCs as compared to HPAEpiCs, such as bone morphogenetic protein 2 (BMP2), stromal cell-derived factor 1 (SDF-1; also known as C-X-C motif chemokine 12 [CXCL12]) and fibroblast growth factors 2 (FGF2).

Ability of LSCs to Form Alveoli-Like Structures and Promote Angiogenesis

When cultured on Matrigel™, LSCs self-assembled into alveoli-like structures (FIG. 3A). Immuno-staining revealed that LSCs expressed aquaporin 5 (open arrowheads, FIG. 3B) and acquire mature lung epithelial cell morphology. Non-differentiated LSCs are shown with solid arrowheads, (FIG. 3B). These non-differentiated cells remain positive for Pro-SPC (white arrow, FIG. 10). Conditioned media from LSCs promote survival/proliferation of human lung epithelial cells (FIG. 3C) and tube formation of human endothelial cells on Matrigel™ (FIG. 3D; LSC-conditioned media vs. control media: 237.8±32.7 μm vs. 108.7±81.1 μm; $p<0.05$), suggesting a pro-survival and pro-angiogenic role of LSC-secreted factors. A cytokine array (FIG. 3E) revealed that as compared to control cells (NHDFs), human LSCs secrete higher concentrations of pro-angiogenic factors such as insulin-like growth factor binding protein 2 (IGFBP2), hepatocyte growth factor (HGF), and brain-derived neurotrophic factor (BDNF).

Regenerative Potential of LSCs in Mice with Pulmonary Fibrosis

Animal study design is outlined as FIG. 4A. Pulmonary fibrosis was induced in severe combined immunodeficiency (SCID) mice with intratracheal bleomycin instillation. 24 hrs later, animals received intravenous infusion of $1\times10^6$ human LSCs or saline control. The animals were followed for 14 days and then sacrificed for endpoint analysis. Macroscopic view of the explanted lungs revealed significant tissue damages (dense dark spots) in the bleomyocin-treated lungs (FIG. 4B), while LSC-treated lungs appeared similar to the lungs in the Sham group. H &E staining (FIG. 4C) revealed that LSC treatment significantly reduced fibrous thickening (by Ashcroft Score) (FIG. 4E; "Bleo+saline" vs. "Bleo+LSC": 5.7±1.0 vs. 4.3±0.7) and tissue infiltration (FIG. 4F; "Bleo+saline" vs. "Bleo+LSC": 11.6±5.7 vs. 4.3±4.8). Masson's trichrome staining confirmed the reduction of fibrosis by LSC treatment (FIG. 4D).

Mechanisms of LSC-Mediated Lung Protection and Regeneration

LSC engraftment reduced tissue apoptosis in the bleomycin-treated lungs. LSC engraftment (DiO-labeled; FIG. 5A) decreased the numbers of TUNEL-positive apoptotic cells (FIG. 5A) in the bleomycin-treated lungs (area w/o LSC vs. area w/LSC: 1.9±0.5% vs. 0.7±0.2% of total nuclei). Such protection was seen in epithelial, stromal, and endothelial cell types in the lungs (FIG. 11). In contrast, LSC treatment increased angiogenesis in the bleomycin-treated lungs: more vWF-positive vasculatures were detected in the LSC-treated lungs (FIG. 5B; "Bleo+saline" vs. "Bleo+LSC": 6.0±2.3 vs. 11.8±3.3 per HPF). Moreover, a greater number of blood vessels were formed around LSCs than in other areas without the presence of LSCs (FIG. 12). These results were consistent with the pro-survival and pro-angiogenic effects of LSCs observed in vitro (FIGS. 3C(1) and 3C(2)). While some injected human LSCs acquired mature lung epithelial cell phenotypes: EGFP-positive LSCs co-expressed differentiation lung epithelial cell marker aquaporin 5 (FIG. 5C, white arrows; FIG. 13, inset panel b), some LSCs remain positive for Pro-SPC (FIG. 13, inset b). To reveal the overall impact of LSC treatment on pulmonary fibrosis, we extracted RNA from the lungs in "Bleo+LSC" and "Bleo+saline" groups. Quantitative PCR array revealed that LSC treatment attenuated the expressions of fibrotic genes in the bleomycin-treated lungs (FIG. 5D).

Rat Lung Spheroids and Lung Spheroid Cells

Using the similar technology, we derived lung spheroids and lung spheroid cells from rat lungs. Lungs from Wistar-Kyoto rats were explanted and minced into small fragments. Cells outgrowing from the lung explants were collected and forced to form lung spheroids in suspension culture. The lung spheroids were re-plated onto adherence culture to generate lung spheroid cells. The morphologies of lung spheroids and lung spheroid cells resemble their human counterparts.

Therapeutic Superiority of LSCs Over AD-MSCs

Because most current clinical trials are using MSCs for treating IPF and COPD, we sought to compare the therapeutic potencies of LSCs and AD-MSCs. To rule out donor variability, we derived rat LSCs and AD-MSCs from the syngeneic Wistar-Kyoto (WKY) rat strains as these rats share the same genetic background. Rat LSCs share a similar antigenic phenotype with their human counterparts, with consistent expressions of CD105, CD90, Pro-SPC and CCSP (FIG. 14). 24 hours after bleomycin instillation, WKY rats were randomized to receive either saline, rat LSCs, or rat AD-MSCs (FIG. 6A). Consistent with previous reports, H&E staining indicated that AD-MSC therapy reduced infiltrates 14 days after cell therapy (FIG. 6B; FIGS. 6C & D, black bars), as compared to saline control (FIG. 6B; FIGS. 6C & D, white bars). There was also a trend in the reduction of fibrotic thickening (by Ashcroft Score). However, the highest therapeutic effects were observed in rats that received LSCs, which expressed the smallest degree of fibrotic thickening and tissue infiltration (FIG. 6B; FIGS. 6C & D). These data suggest that LSCs are superior to AD-MSCs in treating rats with PF.

Discussion

The last decade witnessed a burst of studies on identifying endogenous lung stem cells [24]. Many cell types in the lung, including basal cells, club cells, alveolar type II cells, have been proposed as stem/progenitor cells. However, mesenchymal cells (from bone marrow, adipose tissues, umbilical cord) are still the major players in on-going cell-based therapy trials for treating lung diseases because of the ease of isolating and propagating these cells. Compared to resident lung progenitor cells, mesenchymal cells are easy to isolate and expand.

Multicellular spheroid has been used as a method to generate neural and cardiac stem cells. A recent report indicates infusion of cardiosphere-derived cells in mild-to-moderate heart attack patients reduces scar and increases viable tissue [25]. So far lung spheroid has been used as a method to grow and test lung cancer cells [26]. In the present study, we show lung spheroid as a straightforward method to generate therapeutic lung progenitor cells. The cell yield and growth potential of lung spheroid cells (LSCs) make them suitable for both autologous and allogeneic applications (FIG. 1). No antigenic sorting is required as LSCs represent an selective mixture containing both lung progenitor cells as well as supporting cells (FIG. 2). The origin of LSCs is yet to be determined. Expressions of CD105, CD90, Pro-SPC, and CCSP identify human LSCs, suggesting they may contain lung mesenchymal stem cells, alveolar progenitors, and airway progenitors. LSCs are distinct from MSCs: human MSCs express CD105 and CD90, but not Pro-SPC or CCSP (FIG. 7). A sub-fraction of LSCs is dual positive for Pro-SPC and CSSP, representing the bronchioalveolar stem cells (BASCs). In addition, a small fraction of LSCs also express CD49f (Itga6), p75 NGF, and EpCAM, previously reported as markers for multipotent lung stem cells [27, 28]. The positive percentages for these lung stem cell markers in LSCs are higher than what naturally occurs in the adult lungs. We speculate the spheroid culture may artificially enrich these stem cells. This natural mixture of lung progenitor cells may be a result of the ex vivo cell culture process. The three-dimensional spheroid culture may enrich the stem cell populations. Alternatively, the ex vivo cell culture process may revert mature lung epithelial cells into progenitor cells, a process resembling the dedifferention of lung cells into stem cells in vivo [29]. LSCs could form alveoli-like structures in vitro, suggesting their differentiation potential into mature lung cells (FIG. 2E). The conditioned media from LSCs contains various pro-angiogenic factors (FIG. 4F) and promotes tube formation of endothelial cells (FIG. 2F), suggesting LSC may promote lung regeneration through paracrine mechanisms.

To test the regenerative potential of LSCs in vivo, we created a pulmonary fibrosis model in mice by intratracheal instillation of bleomycin. The use of immunodeficiency (SCID) mice makes it possible to test human LSCs without the fear of rejection. No complications were observed in mice received LSC infusion. No tumors or ectopic tissues were observed in the animals treated with LSCs. Treatment with LSCs inhibited fibrosis (FIG. 3B), infiltration (FIG. 3C), and cell apoptosis (FIG. 4A), but promoted angiogenesis (FIG. 4B). LSCs engraft and acquire mature lung phenotypes in the recipient lungs (FIGS. 4C & D), although such small engraftment and differentiation incidents stem insufficient to explain the observed benefits. Mounting lines of evidence suggest injected stem cells regenerate damaged tissues through indirect paracrine mechanism [30]. We speculate LSCs secrete beneficial factors to modulate the environment and recruit endogenous repair mechanisms (FIGS. 4F & G).

LSCs where able to form alveoli-like structures and acquired mature lung epithelial phenotypes/morphologies in vitro, suggesting their differentiation potential (FIGS. 3A & B). The conditioned media from LSCs promotes lung epithelial cell survival (FIG. 3C) and endothelial cell tube formation (FIG. 3D). Cytokine array data suggested that LSCs may promote lung regeneration through the secretion of anti-apoptotic and pro-angiogenic factors and cytokines (FIG. 3E).

To test the regenerative potential of LSCs in vivo, we created a pulmonary fibrosis model in mice via intratracheal instillation of bleomycin. The use of immunodeficiency (SCID) mice makes it possible to test human LSCs without the fear of rejection. No complications were observed in mice that received LSC infusion. No tumors or ectopic tissues were observed in any animals treated with LSCs. Treatment with LSCs inhibited fibrosis (FIG. 4E), infiltration (FIG. 4F), and cell apoptosis (FIG. 5A), but promoted angiogenesis (FIG. 5B). LSCs engraft and acquire mature lung phenotypes in the recipient lungs (FIG. 5C), although such small engraftment and differentiation incidents seem insufficient to explain the overall benefits. Mounting lines of evidence suggest injected stem cells regenerate damaged tissues through indirect paracrine mechanisms [28]. We speculate LSCs secrete beneficial factors that modulate the environment and recruit endogenous repair mechanisms (FIG. 5E).

Since mesenchymal stem cells (MSCs) are the most popular cells in clinical trials for lung diseases, we performed a head-to-head comparison of rat LSCs and AD-MSCs in the same rat model of PF (FIG. 6). Strikingly, LSCs outperformed AD-MSCs in reducing fibrotic thickening and tissue infiltration in PF lungs. The underlying mechanisms need to be further elucidated. As derived from adult lungs instead of fat tissues, we speculate that LSCs are predesignated to differentiate into lung cells and promote endogenous lung regeneration.

In summary, we identified lung spheroids from healthy human lungs as a new source of lung progenitor cells that can be used for therapeutic lung regeneration. Lung spheroid represents a simple and highly-reproducible method to generate therapeutic lung cells without antigenic sorting. Normally FBS-free media containing EGF is used for lung epithelial stem cell culture. We compare LSCs cultured in two conditions: 1) 25 ng/ml EGF and no FBS; 2) 20% FBS, no EGF. The morphologies of LSCs were similar in those two conditions, albeit the cells cultured in 20% FBS media grew faster (FIG. 15). These yet-to-be elucidated questions will be the effort of our future directions in this line of research. As an autologous product, we anticipate an IPF patient will come to the clinic, after which a lung biopsy will be performed to generate the tissues required for LSC culture. These autologous cells will then be re-introduced into the same patient by intravenous injection. To this end, we confirmed that LSCs can be derived from mouse (FIG. 16 & FIG. 17) and human (FIG. 18) lungs with PF.

Future studies are warranted to elucidate the origin of LSCs and the mechanisms underlying their therapeutic benefits, and to translate these findings to a clinically-relevant large animal model of lung disease.

7. REFERENCES

[1] Cottin V. Interstitial lung disease. European Respiratory Review. 2013; 22:26-32.

[2] Yang J, Jia Z. Cell-based therapy in lung regenerative medicine. Regenerative Medicine Research. 2014; 2:7.

[3] Moodley Y, Atienza D, Manuelpillai U, Samuel C, Tchongue J, Ilancheran S, et al. Human umbilical cord mesenchymal stem cells reduce fibrosis of bleomycin-induced lung injury. Am J Pathol. 2009; 175:303-13.

[4] Ortiz L, Dutreil M, Fattman C, Pandey A, Torres G, Go K, et al. Interleukin 1 receptor antagonist mediates the antiinflammatory and antifibrotic effect of mesenchymal stem cells during lung injury. Proc Natl Acad Sci USA. 2007; 104: 11002-7.

[5] Ortiz L, Gambelli F, McBride C, Gaupp D, Baddoo M, Kaminski N, et al. Mesenchymal stem cell engraftment in lung is enhanced in response to bleomycin exposure and ameliorates its fibrotic effects. Proc Natl Acad Sci USA. 2003; 100:8407-11.

[6] Rojas M, Xu J, Woods C, Mora A, Spears W, Roman J, et al. Bone marrow-derived mesenchymal stem cells in repair of the injured lung. Am J Respir Cell Mol Biol. 2005; 33:145-52.

[7] Tzouvelekis A, Paspaliaris V, Koliakos G, Ntolios P, Bouros E, Oikonomou A, et al. A prospective, non-randomized, no placebo-controlled, phase Ib clinical trial to study the safety of the adipose derived stromal cells-stromal vascular fraction in idiopathic pulmonary fibrosis. J Transl Med. 2013; 11:171.

[8] Takahashi K, Tanabe K, Ohnuki M, Narita M, Ichisaka T, Tomoda K, et al. Induction of Pluripotent Stem Cells from Adult Human Fibroblasts by Defined Factors. Cell. 2007; 131:861-72.

[9] Takahashi K, Yamanaka S. Induction of pluripotent stem cells from mouse embryonic and adult fibroblast cultures by defined factors. Cell. 2006; 126:663-76.

[10] Thomson J A, Itskovitz-Eldor J, Shapiro S S, Waknitz M A, Swiergiel J J, Marshall V S, et al. Embryonic Stem Cell Lines Derived from Human Blastocysts. Science. 1998; 282:1145-7.
[11] Desai T J, Brownfield D G, Krasnow M A. Alveolar progenitor and stem cells in lung development, renewal and cancer. Nature. 2014; 507:190-4.
[12] Kajstura J, Rota M, Hall S R, Hosoda T, D'Amario D, Sanada F, et al. Evidence for Human Lung Stem Cells. New England Journal of Medicine. 2011; 364:1795-806.
[13] Kim C, Jackson E, Woolfenden A, Lawrence S, Babar I, Vogel S, et al. Identification of bronchioalveolar stem cells in normal lung and lung cancer. Cell. 2005; 121: 823-35.
[14] Wansleeben C, Barkauskas C, Rock J, Hogan B. Stem cells of the adult lung: their development and role in homeostasis, regeneration, and disease. Wiley Interdiscip Rev Dev Biol. 2013; 2:131-48.
[15] Barkauskas C E, Cronce M J, Rackley C R, Bowie E J, Keene D R, Stripp B R, et al. Type 2 alveolar cells are stem cells in adult lung. The Journal of Clinical Investigation. 2013; 123:3025-36.
[16] Hogan Brigid L M, Barkauskas Christina E, Chapman Harold A, Epstein Jonathan A, Jain R, Hsia Connie C W, et al. Repair and Regeneration of the Respiratory System: Complexity, Plasticity, and Mechanisms of Lung Stem Cell Function. Cell Stem Cell. 2014; 15:123-38.
[17] Fennema E, Rivron N, Rouwkema J, van Blitterswijk C, de Boer J. Spheroid culture as a tool for creating 3D complex tissues. Trends in Biotechnology. 2013; 31:108-15.
[18] LaBarbera D V, Reid B G, Yoo B H. The multicellular tumor spheroid model for high-throughput cancer drug discovery. Expert Opinion on Drug Discovery. 2012; 7:819-30.
[19] Deleyrolle L, Reynolds B. Isolation, Expansion, and Differentiation of Adult Mammalian Neural Stem and Progenitor Cells Using the Neurosphere Assay. In: Gordon D, Scolding N J, editors. Neural Cell Transplantation: Humana Press; 2009. p. 91-101.
[20] Marbán E. Breakthroughs in Cell Therapy for Heart Disease: Focus on Cardiosphere-Derived Cells. Mayo Clinic Proceedings. 2014; 89:850-8.
[21] Su G, Zhao Y, Wei J, Han J, Chen L, Xiao Z, et al. The effect of forced growth of cells into 3D spheres using low attachment surfaces on the acquisition of stemness properties. Biomaterials. 2013; 34:3215-22.
[22] Su G, Zhao Y, Wei J, Xiao Z, Chen B, Han J, et al. Direct conversion of fibroblasts into neural progenitor-like cells by forced growth into 3D spheres on low attachment surfaces. Biomaterials. 2013; 34:5897-906.
[23] Li T-S, Cheng K, Lee S-T, Matsushita S, Davis D, Malliaras K, et al. Cardiospheres Recapitulate a Niche-Like Microenvironment Rich in Stemness and Cell-Matrix Interactions, Rationalizing Their Enhanced Functional Potency for Myocardial Repair. STEM CELLS. 2010; 28:2088-98.
[24] Kotton D N, Morrisey E E. Lung regeneration: mechanisms, applications and emerging stem cell populations. Nat Med. 2014; 20:822-32.
[25] Makkar R R, Smith R R, Cheng K, Malliaras K, Thomson L E J, Berman D, et al. Intracoronary cardiosphere-derived cells for heart regeneration after myocardial infarction (CADUCEUS): a prospective, randomised phase 1 trial. The Lancet. 2012; 379:895-904.
[26] Amann A, Zwierzina M, Gamerith G, Bitsche M, Huber J M, Vogel G F, et al. Development of an Innovative 3D Cell Culture System to Study Tumour-Stroma Interactions in Non-Small Cell Lung Cancer Cells. PLOS ONE. 2014; 9: e92511.
[27] Chapman H, Li X, Alexander J, Brumwell A, Lorizio W, Tan K, et al. Integrin alpha6beta4 identifies an adult distal lung epithelial population with regenerative potential in mice. J Clin Investig. 2011; 121:2855-62.
[28] Kumar Pooja A, Hu Y, Yamamoto Y, Hoe Neo B, Wei Tay S, Mu D, et al. Distal Airway Stem Cells Yield Alveoli In Vitro and during Lung Regeneration following H1N1 Influenza Infection. Cell. 2011; 147:525-38.
[29] Tata P R, Mou H, Pardo-Saganta A, Zhao R, Prabhu M, Law B M, et al. Dedifferentiation of committed epithelial cells into stem cells in vivo. Nature. 2013; 503:218-23.
[30] Chimenti I, Smith R R, Li T-S, Gerstenblith G, Messina E, Giacomello A, et al. Relative Roles of Direct Regeneration Versus Paracrine Effects of Human Cardiosphere-Derived Cells Transplanted Into Infarcted Mice. Circulation Research. 2010; 106:971-80.

It is to be understood that, while the invention has been described in conjunction with the detailed description, thereof, the foregoing description is intended to illustrate and not limit the scope of the invention. Other aspects, advantages, and modifications of the invention are within the scope of the claims set forth below. All publications, patents, and patent applications cited in this specification are herein incorporated by reference as if each individual publication or patent application were specifically and individually indicated to be incorporated by reference.

What is claimed is:

1. A method of treating a lung disease or lung condition, the method comprising:

administering a composition comprising a plurality of lung spheroids derived from a lung tissue explant to a subject in need thereof, wherein the plurality of lung spheroids comprise:

(i) at least one lung progenitor cell;

(ii) at least one supporting stroma-like cell; and (iii) at least one lung spheroid cell (LSC) that co-expresses at least one supporting stroma-like cell marker and at least one lung progenitor cell marker; wherein the at least one progenitor cell, the at least one supporting stroma-like cell, and the at least one LSC are derived from the same lung tissue explant; and wherein administering the composition alleviates at least one characteristic of the lung disease or lung condition in the subject.

2. The method of claim 1, wherein the lung disease or lung condition is selected from the group consisting of acute lung injury (ALI), acute respiratory distress syndrome (ARDS), asthma, bacterial pneumonia, bronchiolitis obliterans organizing pneumonia (BOOP), chemical pneumonia, chronic bronchitis, chronic obstructive pulmonary diseases (COPD), cystic fibrosis, emphysema, an interstitial lung disease lung cancer, pulmonary edema, pulmonary hypertension, tuberculosis, viral pneumonia, or any combination thereof.

3. The method of claim 2, wherein the interstitial lung disease is sarcoidosis, idiopathic pulmonary fibrosis (IPF), pneumoconiosis, or a pneumonia.

4. The method of claim 1, wherein the alleviation of the at least one characteristic of the lung disease or condition comprises one or more of increasing angiogenesis, regrowing healthy lung epithelium, attenuating expression of a fibrotic gene, attenuating inflammation, and attenuating fibrosis.

5. The method of claim 1, wherein the composition is administered to the subject intra-articularly, intravenously, intraarterially, intramuscularly, intraperitoneally, subcutaneously, intranasally, by inhalation, by bolus injection, or by continuous infusion.

6. The method of claim 1, wherein the composition is administered to the subject at a dose of from about $1.0\times10^4$ cells/kg to about $1.0\times10^{10}$ cells/kg.

7. The method of claim 1, wherein the subject is a human.

8. The method of claim 1, wherein the lung tissue explant is obtained from the subject.

9. The method of claim 1, wherein the lung tissue explant is obtained from a donor subject of the same species as the subject.

10. The method of claim 1, wherein the lung tissue explant is obtained from a donor subject of a different species as the subject.

11. The method of claim 1, wherein the composition is administered to the subject daily, weekly, or annually.

12. The method of claim 1, wherein the at least one lung progenitor cell marker comprises Pro-Surfactant Protein C (SPC), Clara Cell Secretory Protein (CCSP), Integrin Subunit Alpha 6 (ITGA6 or CD49f), p75 Nerve Growth Factor (NGF), Epithelial Cell Adhesion Molecule (EpCAM), p63, Keratin 5 (KRT5), and Aquaporin 5 (Aq5), or any combination thereof.

13. The method of claim 1, wherein the at least one supporting stroma-like cell marker comprises CD105 and/or CD90.

14. The method of claim 1, wherein the at least one LSC does not express one or more of CD45, CD31, CD34, c-kit or any combination thereof.

15. The method of claim 1, wherein the lung spheroids comprise diameters ranging from about 25 μm to about 500 μm.

16. A pharmaceutical composition comprising:

a plurality of lung spheroids derived from a lung tissue explant, wherein the plurality of lung spheroids comprise:

(i) at least one lung progenitor cell;

(ii) at least one supporting stroma-like cell; and (iii) at least one lung spheroid cell (LSC) that co-expresses at least one supporting stroma-like cell marker and at least one lung progenitor marker, wherein the at least one progenitor cell, the at least one supporting stroma-like cell, and the at least one LSC are derived from the same lung tissue explant; and a pharmaceutically acceptable adjuvant, carrier, excipient, or diluent.

17. The pharmaceutical composition of claim 16, wherein the composition is administered to a subject at a dose of from about $1.0\times10^4$ cells/kg to about $1.0\times10^{10}$ cells/kg.

18. The pharmaceutical composition of claim 16, wherein the lung spheroids comprise diameters ranging from about 25 μm to about 500 μm.

19. The pharmaceutical composition of claim 16, wherein the composition comprises from about $90\times10^3$ cells/ml to about $250\times10^3$ cells/ml.

20. The pharmaceutical composition of claim 16, wherein the lung tissue explant is obtained from the subject, or from a donor subject.

21. The pharmaceutical composition of claim 16, wherein:

the at least one lung progenitor cell marker comprises Pro-Surfactant Protein C (SPC), Clara Cell Secretory Protein (CCSP), Integrin Subunit Alpha 6 (ITGA6 or CD49f), p75 Nerve Growth Factor (NGF), Epithelial Cell Adhesion Molecule (EpCAM), p63, Keratin 5 (KRT5), and Aquaporin 5 (Aq5), or any combination thereof, the at least one supporting stroma-like cell marker comprises CD105 and/or CD90; and/or the at least one LSC does not express one or more of CD45, CD31, CD34, c-kit or any combination thereof.

* * * * *